United States Patent
Bura et al.

(10) Patent No.: US 10,566,551 B2
(45) Date of Patent: Feb. 18, 2020

(54) FLUORESCENT COMPOUNDS OF THE BORON THIENYLDIPYRROMETHENE TYPE, AND THEIR USE

(71) Applicants: CENTRE NATIONAL DE LA RECHERCHE SCIENTIFIQUE, Paris (FR); UNIVERSITE DE STRASBOURG, Strasbourg (FR)

(72) Inventors: Thomas Bura, Strasbourg (FR); Nicolas Leclerc, Strasbourg (FR); Sandra Rihn, Saverne (FR); Raymond Ziessel, Souffelweyersheim (FR); Antoine Mirloup, Strasbourg (FR); Thomas Heiser, Hochfelden (FR); Patrick Leveque, Saverne (FR); Sadiara Fall, Strasbourg (FR)

(73) Assignees: CENTRE NATIONAL DE LA RECHERCHE SCIENTIFIQUE, Paris (FR); UNIVERSITE DE STRASBOURG, Strasbourg (FR)

( * ) Notice: Subject to any disclaimer, the term of this patent is extended or adjusted under 35 U.S.C. 154(b) by 189 days.

(21) Appl. No.: 14/414,481

(22) PCT Filed: Jul. 18, 2013

(86) PCT No.: PCT/FR2013/051743
§ 371 (c)(1),
(2) Date: Jan. 13, 2015

(87) PCT Pub. No.: WO2014/013205
PCT Pub. Date: Jan. 23, 2014

(65) Prior Publication Data
US 2015/0171328 A1 Jun. 18, 2015

(30) Foreign Application Priority Data
Jul. 19, 2012 (FR) .................................. 12 57017

(51) Int. Cl.
| | | |
|---|---|---|
| H01L 31/00 | (2006.01) | |
| H01L 51/00 | (2006.01) | |
| C07F 5/02 | (2006.01) | |
| H01L 51/44 | (2006.01) | |
| H01L 51/05 | (2006.01) | |
| H01L 51/42 | (2006.01) | |

(52) U.S. Cl.
CPC ............ H01L 51/008 (2013.01); C07F 5/022 (2013.01); C07F 5/027 (2013.01); H01L 51/448 (2013.01); H01L 51/0558 (2013.01); H01L 51/424 (2013.01)

(58) Field of Classification Search
USPC ....................................... 136/263
See application file for complete search history.

(56) References Cited

U.S. PATENT DOCUMENTS

| | | | |
|---|---|---|---|
| 5,433,896 A | 7/1995 | Kang et al. | |
| 2006/0076050 A1* | 4/2006 | Williams ............... | B82Y 10/00 136/263 |
| 2008/0019921 A1 | 1/2008 | Zhang | |
| 2013/0244251 A1 | 9/2013 | Chang et al. | |

FOREIGN PATENT DOCUMENTS

| | | |
|---|---|---|
| JP | 2008109097 | 5/2008 |
| WO | 2002100975 | 12/2002 |
| WO | 2006087458 | 8/2006 |
| WO | 2010075512 | 7/2010 |
| WO | 2010125907 | 11/2010 |

OTHER PUBLICATIONS

Rihn et al., "Versatile synthetic methods for the engineering of thiophene-substituted Bodipy dyes", Tetrahedron Letters 50, 2009, pp. 7008-7013.*
Bura et al., "High-Performance Solution-Processed Solar Cells and Ambipolar Behavior in Organic Field-Effect Transistors with Thienyl-BODIPY Scaffoldings", J. Am. Chem. Soc. 2012, 134, Oct. 5, 2012, pp. 17404-17407.*
Machine translation of WO 2010/125907, Nov. 4, 2010, pp. 1-24.*
Erten-Ela et al: "A panchromatic boradiazaindacene (Bodipy) sensitizer for dye-sensitized solar cells" dated Aug. 1, 2008.
Rousseau et al: "Bodipy derivatives as donor materials for bulk heterojunction solar cells" dated Jan. 1, 2009.
Cortizo-Lacalle et al: "Bodipy-based conjugated polymers for broadband light sensing and harvesting applications" dated Jan. 1, 2012.
Bura et al: "Absorption tuning of monosubstituted triazatruxenes for bulk heterojunction solar cells" dated Nov. 18, 2011.
Rousseau et al: "Multi-donor molecular bulk heterojunction solar cells: improving conversion efficiency by synergistic dye combinations" dated Jan. 1, 2009.
International Search Report dated 2013.
Loudet et al., "BODIPY Dyes and Their Derivatives: Syntheses and Spectroscopic Properties," Chem. Rev., 107, pp. 4891-4932 (2007).
Development of dual functional SPECT/Fluorescent probes for imaging cerebral p-amyloid plaques dated Apr. 20, 2010.

\* cited by examiner

*Primary Examiner* — Thanh Truc Trinh
(74) *Attorney, Agent, or Firm* — Venable LLP; Keith G. Haddaway; Henry J. Daley

(57) ABSTRACT

The present invention concerns fluorescent boron thienyldipyrromethene type compounds, their preparation process, as well as their use as an electron donor in the field of organic electronics, in particular for the production of a photoactive layer in photovoltaic cells of the bulk heterojunction type or for the production of field effect transistors.

18 Claims, 2 Drawing Sheets

FLUORESCENT COMPOUNDS OF THE BORON THIENYLDIPYRROMETHENE TYPE, AND THEIR USE

RELATED APPLICATIONS

Figure 1:
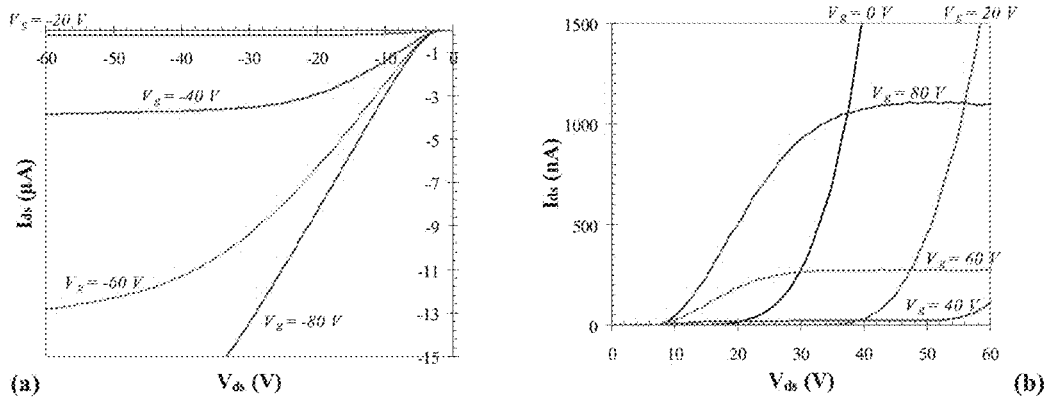

This application is a National Phase Application of PCT/FR2013/051743, filed on Jul. 18, 2013, which in turn claims the benefit of priority from French Patent Application No. 12 57017 filed on Jul. 19, 2012, the entirety of which are incorporated herein by reference.

BACKGROUND

Field of the Invention

The present invention relates to fluorescent compounds of the boron thienyldipyrromethene type, to their preparation processes, and to their use as an electron donor in the field of organic electronics, in particular for the production of a photoactive layer in photovoltaic cells of the bulk heterojunction type or for the production of field effect transistors.

DESCRIPTION OF RELATED ART

The most widely used photovoltaic cells are constituted by semiconductors, principally based on amorphous, polycrystalline or monocrystalline silicon (Si). They are generally in the form of thin plates with sides of about ten centimetres sandwiched between two metal contacts with a thickness of the order of a millimetre. The best performing silicon-based cells comprise an active layer of monocrystalline silicon with a conversion yield which can reach 25% in the laboratory.

Although they perform well, photovoltaic cells based on silicon, in particular on monocrystalline silicon, suffer from the major disadvantage of being expensive because of the high price of this raw material and the thermal budgets involved during production of the photovoltaic cells. For this reason, part of the research has been directed to cells based on thin layer semiconductors.

Cells based on organic semiconductors and organometallic compounds, which have a lower cost price than that of silicon, have already been proposed. Their use in the photovoltaics field is based on the capacity of certain π-conjugated polymers and oligomers or certain small π-conjugated molecules to convert light energy into electrical energy. When a junction is constituted, composed of two semiconductors of different natures, respectively with an electron donor and electron acceptor nature and of which at least one is an organic compound, a heterojunction is thus formed.

For this reason, heterojunctions comprising an organic electron donor type semiconductor and an organic or inorganic electron acceptor type semiconductor have been used for a number of years in many applications in the field of organic electronics, and in particular in the particular field of photovoltaic cells. In general, in such cells, a n-conjugated polymer, a n-conjugated oligomer or a small n-conjugated molecule acts as the electron donor and is brought into the presence of an electron acceptor such as fullerene, for example, or a derivative thereof. Under light irradiation, a bound electron-hole (exciton) pair is created on the electron donor. This exciton is dissociated when the electron jumps from the LUMO level of the donor to the LUMO level of the acceptor, the hole remaining at the HOMO level of the donor. The charges, which have thus been separated, are then collected at the electrodes and generated an electric current.

Particular examples of the many organic compounds which are known in the prior art and which can be used as electron donors to produce active layers and which may be cited include oligothiophenes (Fitzner, R et al., Adv. Funct. Mater., 2011, 21, 897-910), diketopyrrolopyrrole (DPP) as described, for example, by Walker, B et al. (Adv. Funct. Mater., 2009, 19, 3063-3069), squaraines (Wei, G. et al., Adv. Eng. Mater., 2011, 2, 184-187 and Ajayaghosh, A. Acc. Chem. Res., 2005, 38, 449-459), hexabenzocoronenes (Wong, W. W. H. et al., Adv. Funct. Mater., 2010, 20, 927-938), merocyanines (Kronenberg, N. M. et al., Chem. Commun., 2008, 6489-6491), oxoindane donor-acceptors (Bürckstümmer, H. et al., Angew. Chem. Int. Ed., 2011, 4506, 11628-11632), and thiadiazolo-bithiophenes (Sun, Y. et al., Nature Mater., 2011, 11, 44-48).

However, photovoltaic cells employing these compounds do not provide complete satisfaction because their performances in terms of the conversion of light energy into electrical energy are poorer than that of cells based on silicon.

Objects and Summary

Thus, there is a need for compounds with a cost price which is lower than that of silicon and which could in particular be used effectively as an electron donor for the preparation of an active layer in a photovoltaic conversion cell or for the production of field effect transistors.

This aim is achieved with compounds with formula (I) which will be described below. In fact, the inventors have now discovered that certain boron thienyldipyrromethene (thio-BODIPY) type derivatives, the formula for which will be defined below, exhibit excellent electron donor properties, which means that they can advantageously be used, in combination with an electron acceptor, for the preparation of an active layer (bulk heterojunction) in a photovoltaic cell or for the production of field effect transistors.

A compound in accordance with the present invention is a boron dipyrromethene derivative (BODIPY) which has the following formula (I):

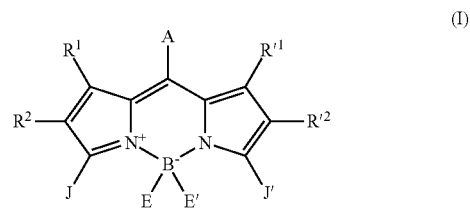

in which:
A represents a hydrogen atom; a $C_1$-$C_6$ alkyl chain and preferably a methyl group; a phenyl ring; a phenyl ring substituted with one or more W groups selected from a halogen atom, preferably iodine or bromine, a linear or branched $C_2$-$C_{20}$ carbon chain which may contain one or more heteroatoms selected from S, O and N, a formyl, carboxyl, thiophene, bis-thiophene or ter-thiophene group, a phenyl ring, a phenyl ring substituted with a linear or branched $C_2$-$C_{20}$ carbon chain, which may contain one or more heteroatoms selected from S, O, Si and N, the or said W groups being in the 3, 4 and/or 5 position of said phenyl ring; an aromatic ring containing a heteroatom selected from S, O, N and Si, said aromatic ring optionally being substituted with a halogen atom (preferably I or Br) or a linear or branched $C_2$-$C_{20}$ carbon chain which may contain one or more heteroatoms selected from S, O and N;

$R^1$, $R^2$, $R'^1$, $R'^2$, which may be identical or different, represent a hydrogen atom, a halogen atom (preferably I or Br), a $C_1$-$C_6$ alkyl radical (preferably methyl or ethyl); the substituents $R^1$ and $R^2$ together, and $R'^1$ and $R'^2$ together may also form a saturated or unsaturated carbon cycle containing 5 or 6 atoms, said cycle optionally containing a heteroatom selected from S, Si, O, N and P;

E and E', which may be identical or different, represent a fluorine atom or a group with the following formula (II): —C≡C-L, in which L is selected from a single bond; a $C_1$-$C_{10}$ alkenylene and a saturated, linear or branched, $C_1$-$C_{20}$ carbon chain interrupted by 1 to 10 oxygen atoms and in which case L is terminated by a group selected from a $C_1$-$C_4$ alkyl radical (preferably methyl), a phosphate group or a silyl group; L may also represent a polyaromatic motif which may be substituted or comprising the heteroatoms S, O or N such as a thiophene, polythiophene, pyrene, perylene, arylene, triazatruxene or truxene group;

J represents a group with the following formula (II):

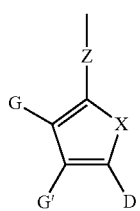

(III)

in which:
Z is a linker providing the connection with the boron dipyrromethene group with formula (I) and is selected from a vinyl function, an acetylene function and a C—C bond connected directly to the boron dipyrromethene group with formula (I);
X is selected from the heteroatoms N, O, Si and S, S being preferred,
D represents a group selected from the groups arylene, heteroarylene, benzothiadiazole, and $C_2$-$C_{20}$ carbon chains, which may be linear or branched,
G and G', which may be identical or different, represent a hydrogen atom, a linear or branched $C_2$-$C_{20}$ carbon chain which may contain one or more heteroatoms selected from S, O, Si and N, it being understood that G and G' together, as well as G' and D together, may also form, together with the atoms of the carbon cycle to which they are connected, a fused cycle selected from thienothiophenes and thienopyrroles;
J' represents a methyl group or a group identical to the group J with formula (III) as defined above.

The above compounds with formula (I) have the following advantages:
a very high absorption in the visible between 450 and 950 nm;
energy levels which are suitably positioned to ensure effective electron transfer from the electron donor to the electron acceptor so as to produce an active layer of a photovoltaic cell;
a relatively deep, low energy HOMO orbital such that high open circuit voltages can be obtained,
a relatively flat molecular structure, which means that organisation into thin layers is favoured so that charge transport is facilitated and high mobilities of these charges can be obtained in order to obtain high current densities;
functions which ensure that they have good solubility and film-forming abilities on flat substrates;
high chemical, electrical and photochemical stabilities; and finally
ease of synthesis, which means that large quantities of compounds with formula (I) can be prepared.

The compounds with formula (I) of the invention in fact have thiophene, oligothiophene, furan, oligofuran or benzothiadiazole motifs directly involved in the delocalization system at the 3, 5 positions, which means that the absorption properties and the optical gap can be varied at will from 1.70 (compound with formula B11 defined below) and 1.40 (compound with formula B19 defined below). This situation is favourable to the production of tandem photovoltaic cells.

In addition, the presence of thiophene, oligothiophene, furan, oligofuran or benzothiadiazole motifs substituted with flexible chains favours the solubility and film-forming capability of the compounds with formula (I).

In accordance with a preferred embodiment of the invention, A is selected from a hydrogen atom, an unsubstituted phenyl group, a substituted phenyl group, a thiophene group or a substituted thiophene group. In accordance with a more particularly preferred embodiment, A is selected from methylphenyl, iodophenyl and iodothiophene groups.

In accordance with another preferred embodiment, $R^1$ and $R'^1$ are identical and represent a methyl radical and $R^2$ and $R'^2$ are identical and represent a hydrogen atom.

In accordance with yet another preferred embodiment of the invention, D is preferably a thiophene, furan, pyridine, naphthalene, anthracene, pyrene, perylene, or a benzothiadiazole group substituted with one or more thiophene or furan groups carrying one or more chains which may be linear or branched containing 2 to 20 carbon atoms which may contain one or more heteroatoms selected from S, O, Si and N.

Particular compounds with formula (I) above which may be mentioned are the compounds B2, B3, B4, B5, B6, B7, B8, B9, B10, B11, B12, B13, B15, B16, B17, B19, B20, B21, B22, B24, B25, B26, B27, B28, B29, B30, B31, B32, B33, B34, B35, B36 and B39 with the following formulae:

B2
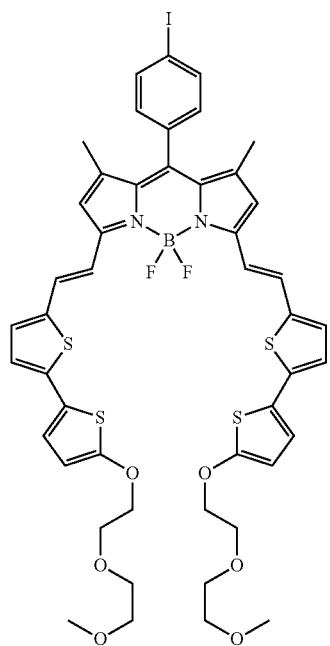
B3
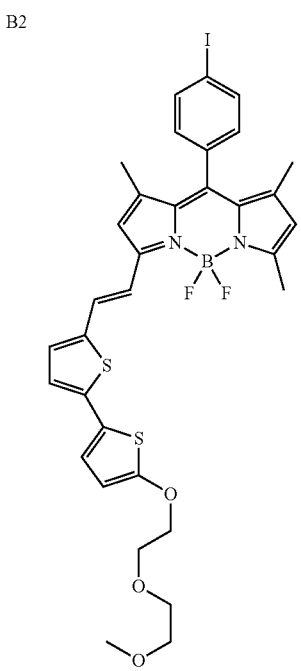
B4
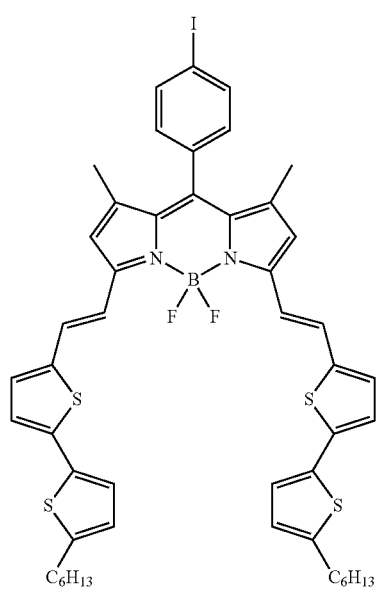
B5
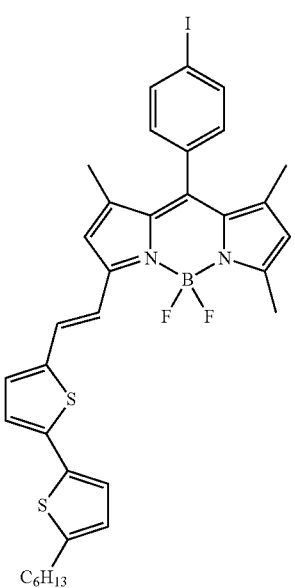

-continued
B6
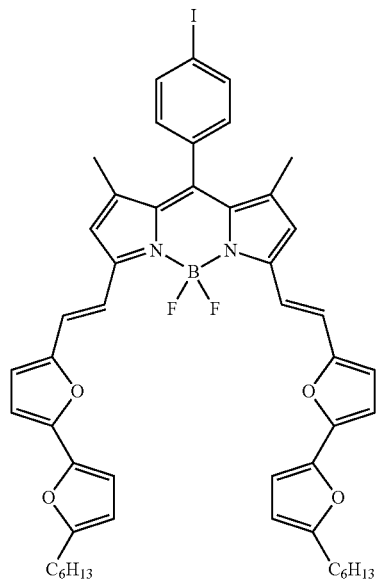
B7
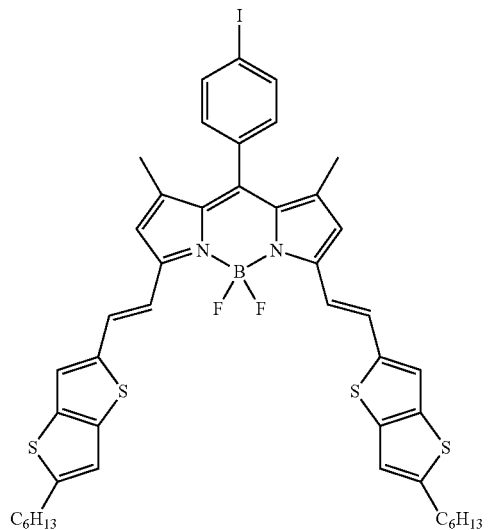
B8
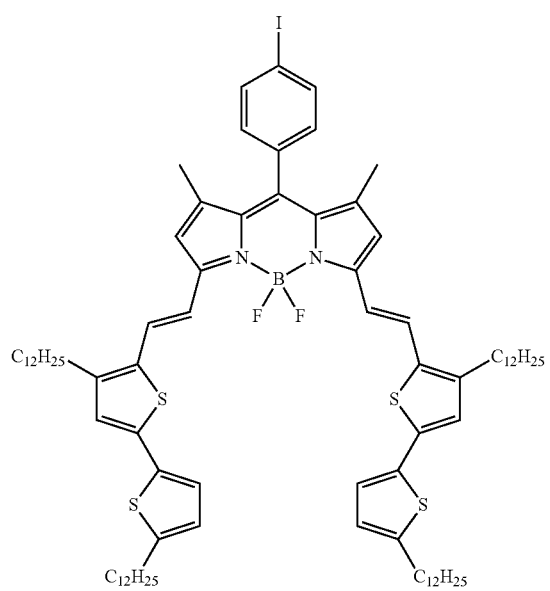
B9
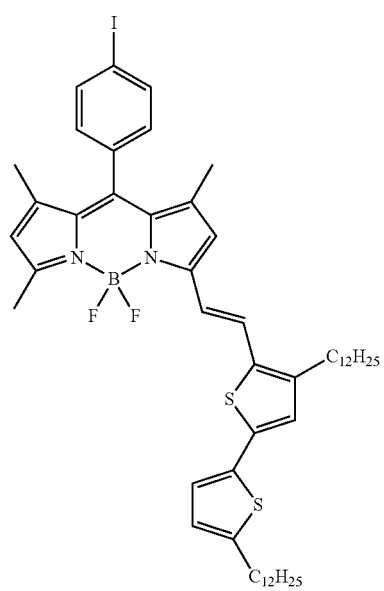
B10
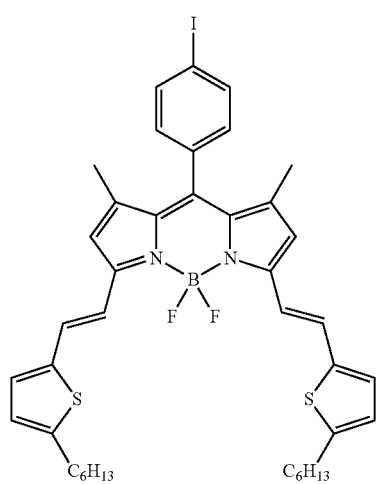
B11
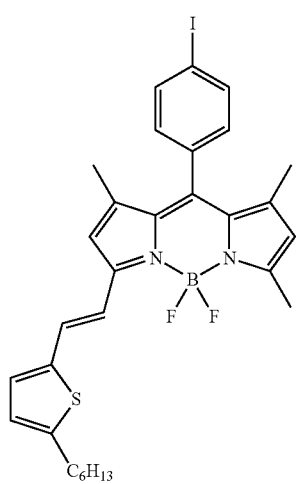

-continued
B12
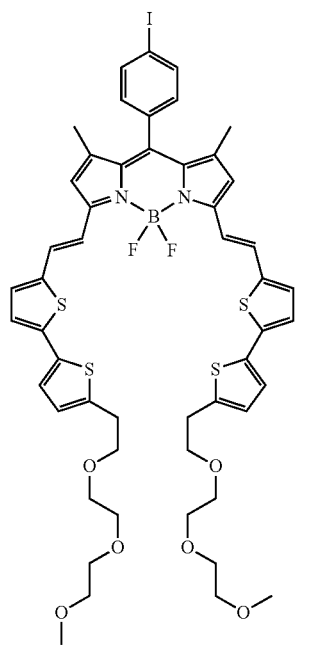
B13
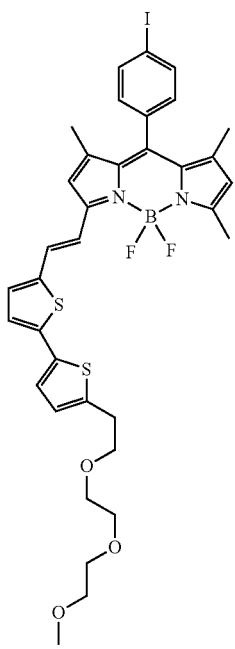
B15
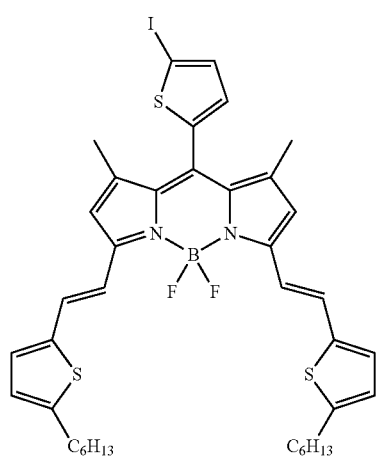
B16
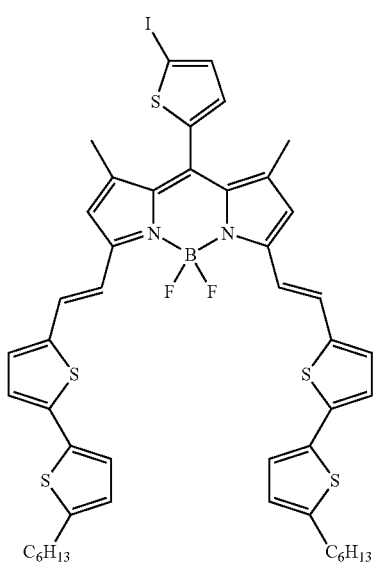

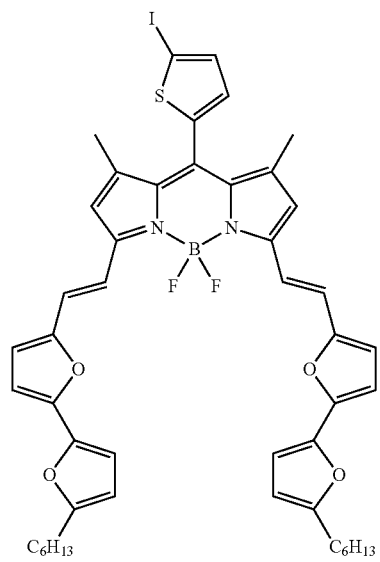
B17
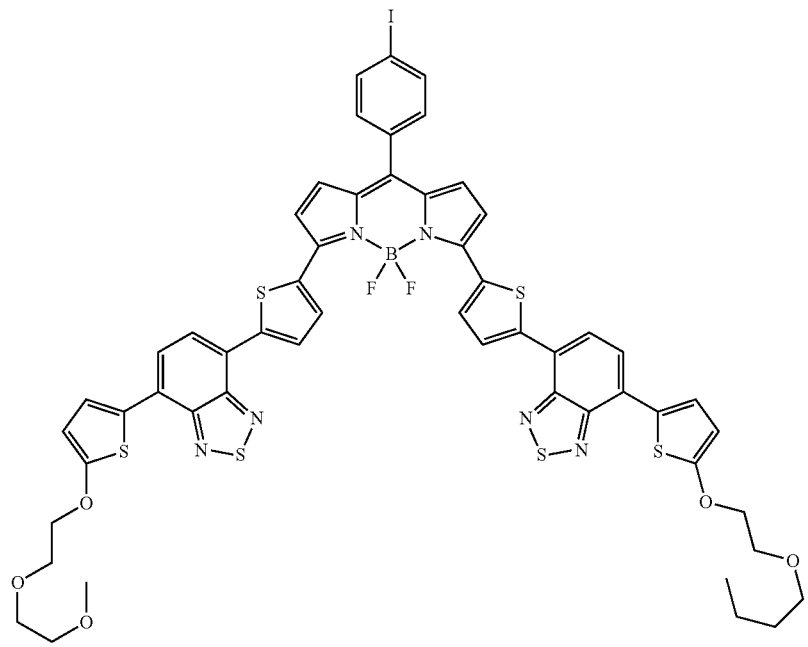
B19

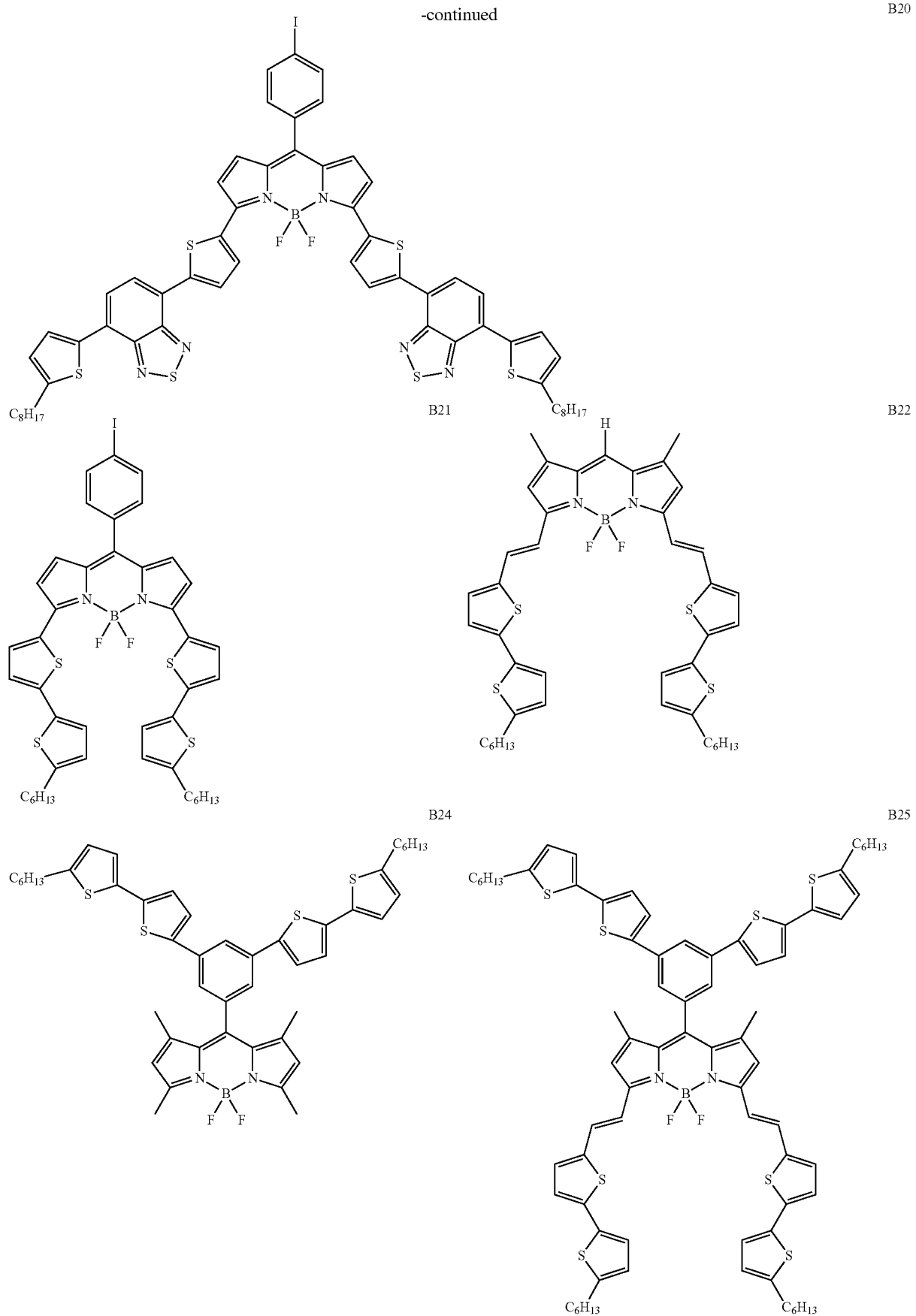

-continued
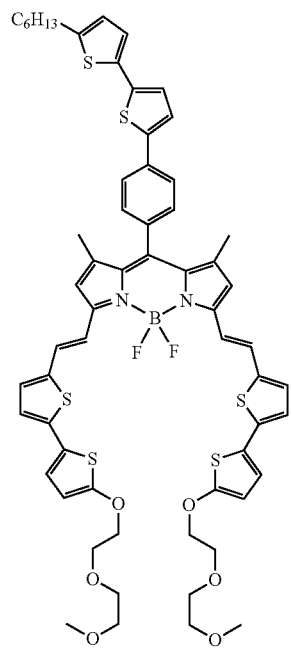
B26
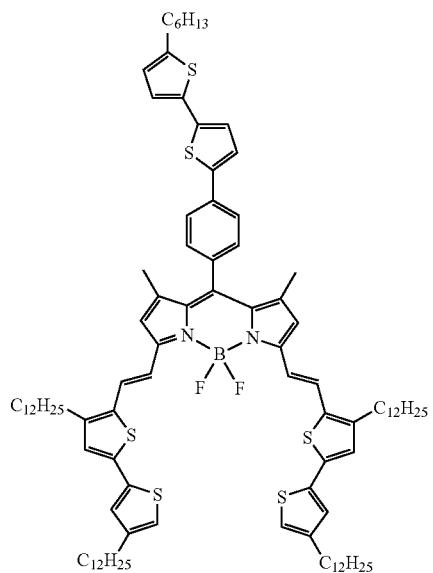
B27
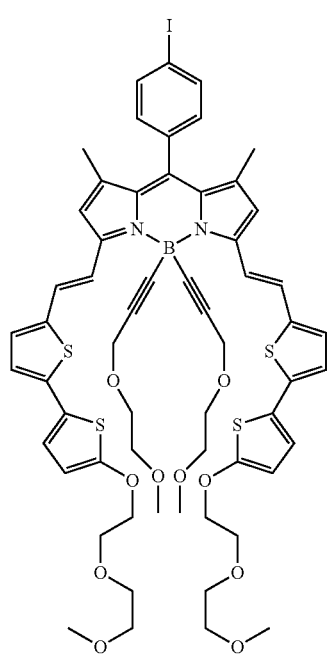
B28
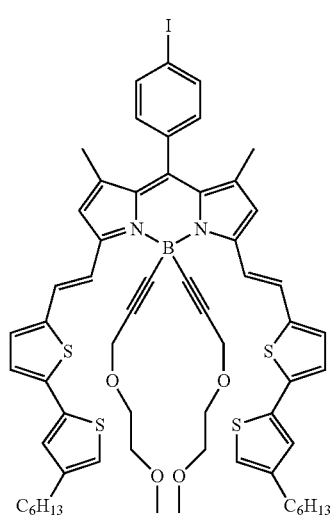
B29

-continued
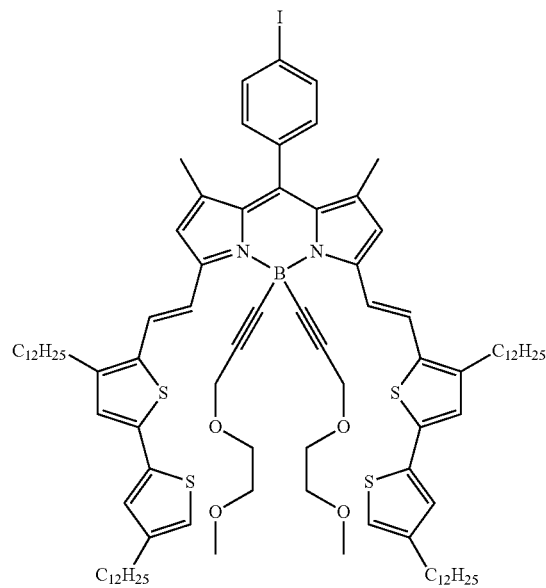
B30
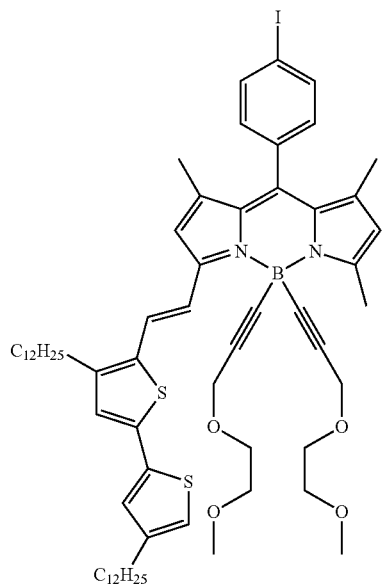
B31
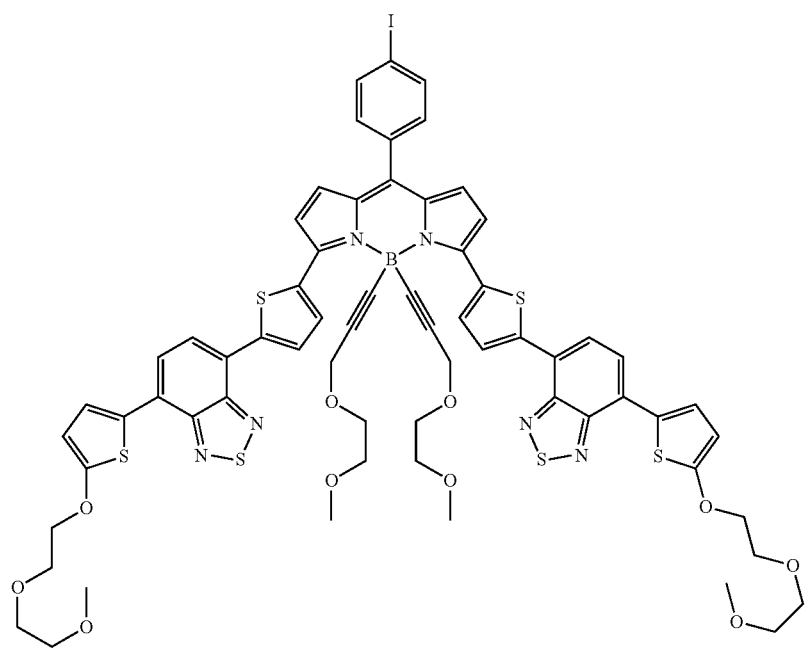
B32

-continued
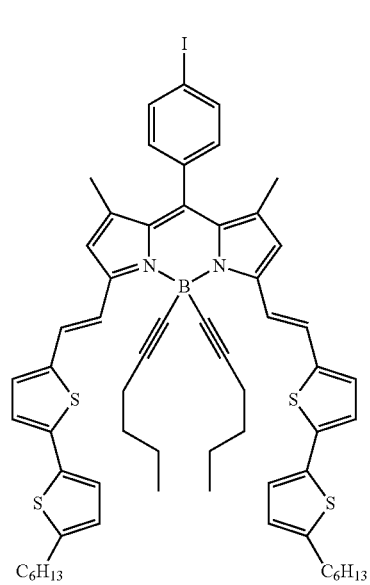
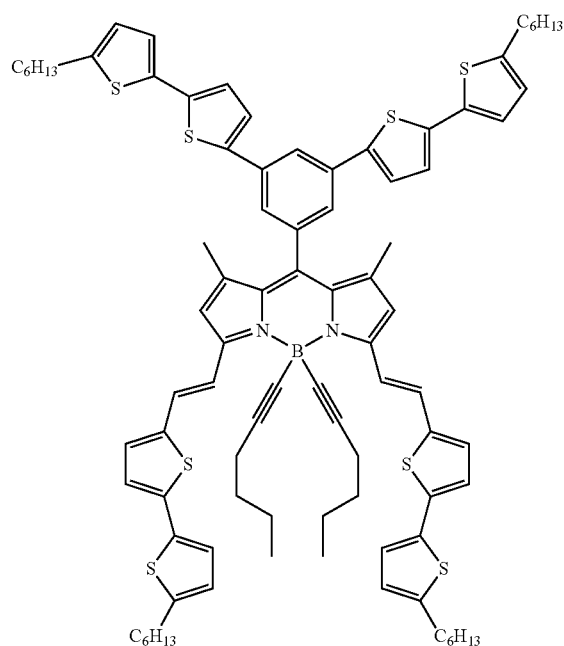
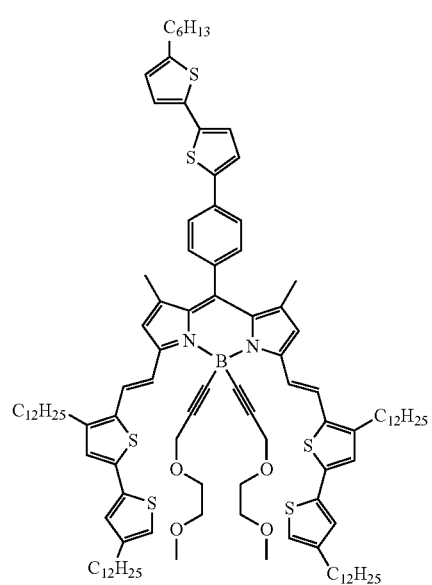
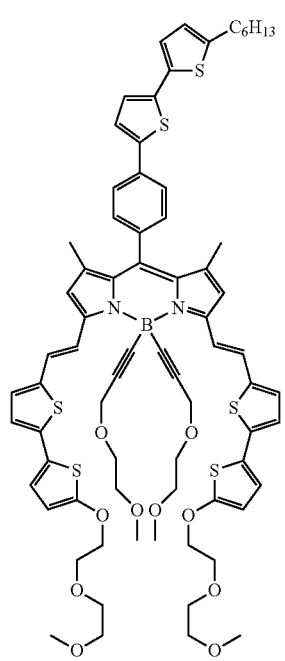

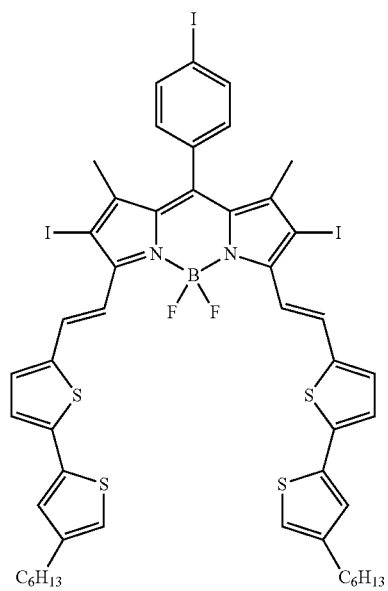

It should be noted that in the above compounds, for the sake of simplicity the positive and negative charges respectively present on the nitrogen atom and the boron atom of the boron dipyrromethene group are not shown.

Particularly preferred compounds from these are the compounds B2, B4, B19, B28 and B32. In the particular case of the compound B4, the presence of thiophene in the delocalisation system favours the mobility of the charges and an ambipolar character. This mobility is important as regards charge extraction.

A compound with formula (I) in accordance with the present invention may be prepared in accordance with the following reaction scheme:

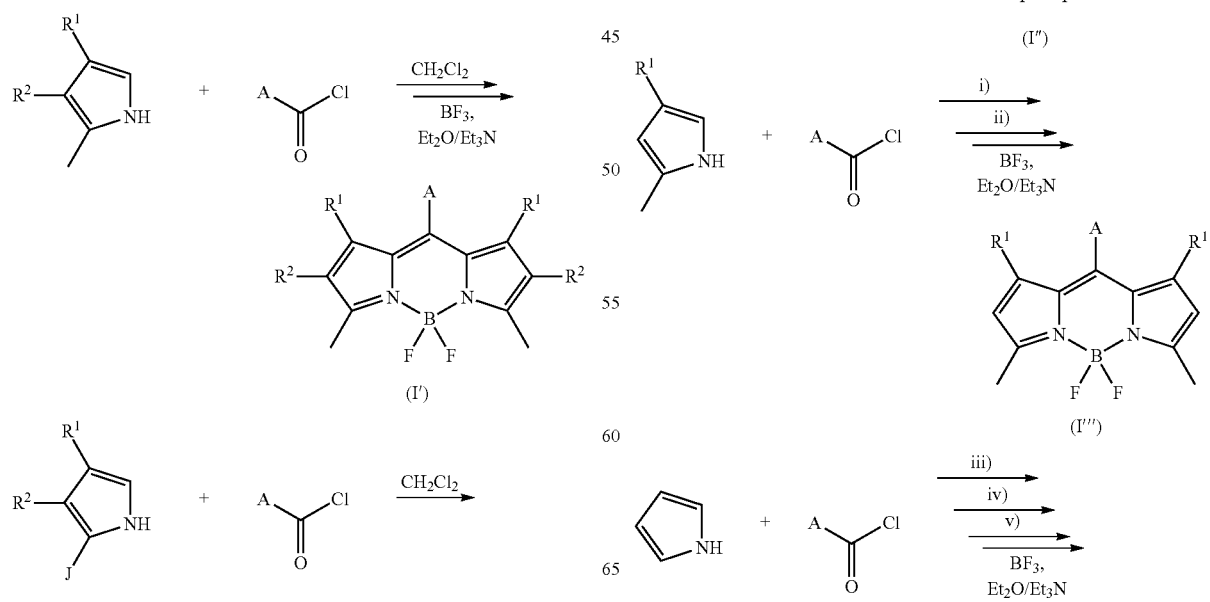

-continued

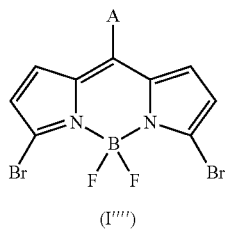

(I'''')

i) CH$_2$Cl$_2$; ii) DDQ or chloranil; iii) pyrrole as the solvent; iv) NBS/THF; v) DDQ in accordance with which a pyrrole derivative is condensed with an acid chloride or aldehyde derivative carrying a group A as defined above for the compounds with formula (I) under anhydrous conditions to obtain a compound with formula (I'), (I'), (I''') or (I'''') depending on the case, in which formula A, R$^1$, R$'^1$, R$^2$, R$'^2$, J and J' have the meanings given for those indicated above for the compounds with formula (I). In the case of acid chlorides, the dipyrromethene derivatives may be complexed in a basic medium with BF$_3$ etherate. In the case of aldehyde derivatives, the intermediate dipyrromethane is oxidized to dipyrromethene and complexed in a basic medium with BF$_3$ etherate. For the disymmetrical compounds, condensation is carried out in two steps starting from the corresponding acid chlorides.

The compounds with formula (I) of the invention are electron donors compared with the compounds conventionally used as electron acceptors in photovoltaic conversion cells such as, for example, fullerene derivatives. This property means that they can be used for the preparation of a heterojunction of a photovoltaic conversion cell. Certain compounds with formula (I) such as the compound with formula B4 also constitute good semiconductors, which also means that they can be used for the production of ambipolar field effect transistors.

Thus, the invention also pertains to the use of at least one compound with formula (I) as defined above, as electron donors, for the preparation of a bulk heterojunction in a photovoltaic cell.

In a further aspect, the invention concerns the use of at least one compound with formula B4 as defined above, as a semiconductor material for the production of an ambipolar field effect transistor, i.e. capable of producing both electrons and holes.

The invention also concerns a photovoltaic cell comprising at least one support, an anode (positive electrode), an active layer (heterojunction) comprising at least one electron donor and at least one electron acceptor, and a cathode (negative electrode), said cell being characterized in that the electron donor is selected from compounds with formula (I) as defined above.

The electron acceptor is preferably selected from fullerene (C60, C70) derivatives such as [6,6]-phenyl-C$_{61}$-methyl butyrate (PC$_{61}$BM), carbon nanotubes, perylene derivatives and tetracyanoquinodimethane (TCNQ) derivatives In a preferred embodiment, the compound with formula (I)/electron acceptor weight ratio varies from 10/1 to 1/3.

In accordance with the invention, the substrate is preferably a transparent substrate formed from a material which may be flexible or rigid, for example glass, and onto which a positive electron is deposited which is constituted by oxides of metals, for example indium tin oxide (ITO).

The negative electron is preferably an aluminium electrode or a calcium/aluminium bi-layer electrode.

A buffer layer may be interposed between the active layer and the positive electrode in order to improve the interface between these two layers. A buffer layer of this type may in particular be constituted by a layer of a blend of two polymers: poly(3,4-ethylenedioxythiophene) (PEDOT) and sodium poly(styrene sulphonate) (PSS):a PEDOT:PSS layer.

Another buffer layer may also be interposed between the active layer and the negative electrode in order, here again, to improve the interface between these two layers. A buffer layer of this type may in particular be constituted by a layer of lithium fluoride (LiF).

The positive electrode (cathode) may also be a metallic oxide of the MoO$_3$, MoO$_x$, WO$_x$, ZnO etc. or other type, which is useful for extracting positive charges from the device.

The photovoltaic cell of the invention may be prepared using techniques which are known to the skilled person, in particular by means of a process consisting of depositing, onto a positive electrode which has already been covered with a buffer layer, a solution of at least one compound with formula (I) and at least one electron acceptor in an appropriate solvent such as chloroform or chlorobenzene, for example. The active layer may be deposited using any appropriate technique, preferably by spin-coating.

A second buffer layer may also be deposited onto the active layer, followed by the negative electrode using any appropriate technique which is known to the skilled person, in particular by gas phase deposition.

The invention also concerns an ambipolar field effect transistor produced from a compound with formula B4. Said field effect transistor comprises a source, a drain, a gate to which a control voltage is applied and a channel constituted by an organic semiconductor, said channel being in contact with the insulator or the gate oxide. It is characterized in that the organic semiconductor is a compound with formula B4 as defined above.

Several field effect transistor configurations are possible. Either the three contacts are present below the channel constituted by a compound with formula (I) (bottom contact/bottom gate configuration), or the drain and the source are below the channel and the gate is above (bottom contact/top gate configuration), or the drain and the source are above the channel and the gate is below it (top contact/bottom gate configuration). By way of a particular exemplary embodiment and in accordance with the first type of configuration (bottom contact/bottom gate), the gate is constituted by a highly doped semiconductor substrate (in this case an n-type silicon substrate with n=3×10$^{17}$/cm$^3$) on which a gate oxide (such as, for example, silicon oxide, SiO$_2$) is deposited with a typical thickness of close to 100 µm (230 µm here). The drain and the source are pre-lithographed contacts which may, for example, be constituted by an indium-tin oxide (ITO) (10 nm)/Au (30 nm) bi-layer. The surface of the silicon oxide which will act as the gate oxide between the interdigital source and drain contacts has to be passivated in order to avoid the presence of too many electron traps at its surface. Passivation may be carried out in various manners which are well known to the skilled person such as, for example, by depositing a hexamethyldisilazane (HMDS) monolayer by means of spin-coating. The transistor is finished by depositing the channel, one of the compounds with formula (I) diluted in a solvent such as chloroform or chlorobenzene, by means of spin-coating. The field effect transistor is characterized by its array of output characteristics, i.e. the measurement of the intensity between the drain and the source (Ids) as a function of the potential difference between the drain and the source (Vds) for different gate voltages (Vg) as well as by its transfer characteristics (Ids as a function of Vg with a fixed Vds). The output characteristics obtained from the compound B4 are clear indications to a skilled person of ambipolar transport, i.e. a capacity to transport holes and electrons at the same time. In this compound B4, the mobilities of the two types of carriers (extracted from the transfer characteristics using the usual formulae) are high (more than $10^{-3}$ cm$^2$Ns) and the like.

The present invention is illustrated by the following examples but is not limited thereto.

EXAMPLES

In the following examples, the compounds listed below were synthesized in accordance with their respective protocols given in the literature:

Compounds B1 and B40: A. Birghart et al., J. Org. Chem., 1999, 64, 7813;
Compounds 5 and 8: K. H. Kim et al., Chem. Mater., 2007, 19, 4925-4932;
Compound 6: O Gidron et al., Chem. Commun., 2011, 47, 1976-1978;
Compound 10: N. Leclerc et al., Chem. Mater., 2005, 17(3), 502-513;
Compound 11: T. Rousseau et al., Chem Commun., 2009, 1673-1675;
Compound 15: S. U. Ku et al., Macromolecules, 2011, 44, 9533-9538;
Compound 22: D. W. Chang et al., Journal of Polymer Science, Part A: Polymer Chemistry, 2012, 50, 271-279;
Compound 30: International application WO 2010076516;
Compound B18: M. R. Rao et al., Journal of Organometallic Chemistry, 2010, 695, 863-869;
Compound B23: M. Benstead et al., New Journal of Chemistry, 2011, (35) 7, 1410-1417.
Compound B37: A Cui et al., Journal of Photochemistry and Photobiology A: Chemistry, 2007, 186, 85-92.

In the following examples, the following general procedures were employed:

General Procedure n°1 for Knoevenagel Type Condensation:

The boron dipyrromethene derivative (the molecular structure of which is represented by formulae (I' or I''') and corresponding to the compound with formula (I)) which is to be obtained (1 equivalent) and the aldehyde derivative (1 to 2.3 equivalents) are dissolved in a toluene/piperidine mixture (10/1, v/v) in a single-necked 100 mL flask, then a catalytic quantity of para-toluenesulphonic acid (p-TsOH) is added. The mixture, with stirring, is heated to its boiling point (temperature of oil bath: 140° C.) until all of the solvent has evaporated off. The progress of the reaction was monitored by thin layer chromatography (TLC). The impure reaction mixture is then dissolved in dichloromethane.

The organic phase is then washed with water (3×20 mL) then with a saturated solution of NaCl (1×20 mL), dried over Na$_2$SO$_4$, MgSO$_4$ or filtered over hydrophilic cotton. After evaporation, the organic residue is purified by silica gel column chromatography with suitable solvents.

General Procedure n°2 for Substitution of Fluorine Atoms with Acetylene Derivatives (Case in which E and/or E' is a Group with Formula (II)):

Ethylmagnesium bromide (1.0 M in THF, 2.5 to 3.5 equivalents) under argon is added to a solution of an acetylenic derivative of the group with formula E/E' (3 to 4 equivalents) in anhydrous THF at ambient temperature. The mixture is stirred for 2 hours at 60° C. then cooled to ambient temperature. The solution obtained is transferred using a cannula into a solution of a boron dipyrromethene derivative with formulae (I') or (I''') or (1'''') corresponding to the compound with formula (I) which is to be obtained (1 equivalent) in anhydrous THF. The solution is stirred overnight at 60° C., then water is added. This solution is extracted with dichloromethane. The organic phase is then washed with water (3×20 mL) then with a saturated NaCl solution (1×20 mL). After evaporation, the organic residue is purified by silica gel column chromatography with suitable solvents.

General Procedure n°3 for Suzuki Type Coupling:

A solution of 2 mol/L of K$_2$CO$_3$ (2 to 4 equivalents) and a boronate derivative (1 to 3 equivalents) is added at ambient temperature to a solution of the boron dipyrromethene derivative with formula (I') or (I'''') in toluene. The mixture is degassed in argon for 45 minutes. After degassing the catalyst, tetrakis(triphenylphosphine)palladium ([Pd(PPh$_3$)$_4$], 10% molar) is added under argon. The mixture is stirred for 12 to 18 hours at 110° C. At the end of the reaction, dichloromethane is added, then the solution is washed with water (3×20 mL) then with a saturated NaCl solution (1×20 mL), and finally dried over Na$_2$SO$_4$, MgSO$_4$ or filtered over hydrophilic cotton. After evaporation, the organic residue is purified by silica gel column chromatography with suitable solvents.

General Procedure n°4 for the Preparation of Aldehydes (Vilsmeier Type Formylation):

1.5 equivalents of POCl$_3$ is added to a solution of anhydrous DMF at 0° C. The mixture is stirred for 1 hour at ambient temperature. The reaction medium is then brought to 0° C. and the aromatic derivative is added under argon. The mixture is then heated to 60° C. for 12 to 18 hours. At the end of the reaction, ether (or ethyl acetate) is added and the solution is washed with water (3×20 mL) then with a saturated NaCl solution (1×20 mL), and finally dried over Na$_2$SO$_4$. After evaporation, the organic residue is purified by silica gel column chromatography with suitable solvents.

Example 1

Synthesis of Compounds B2 and B3

The compounds B2 and B3 were synthesized in accordance with the following synthesis scheme:

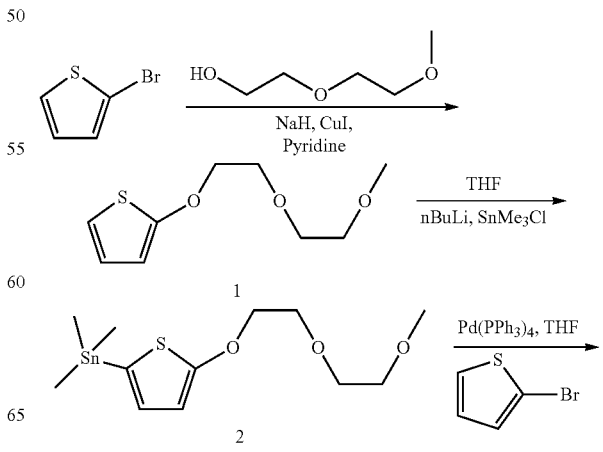

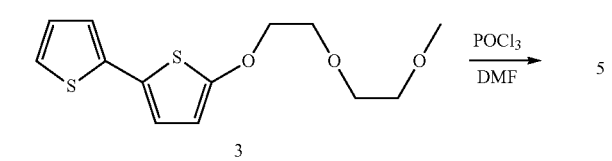

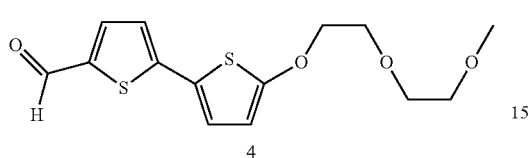

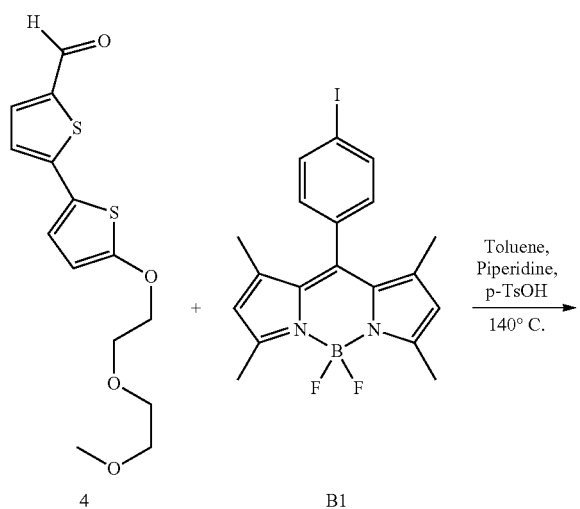

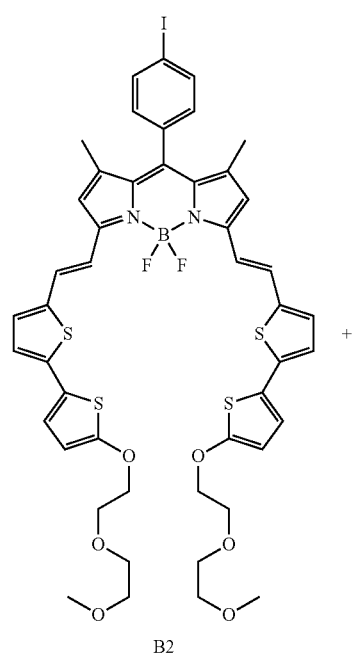

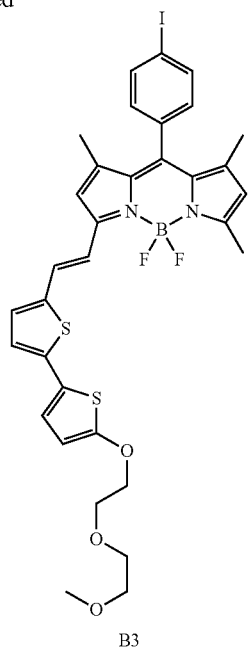

1) First Step: Synthesis of 2-(2-(2-methoxyethoxy)-ethoxy)thiophene (Compound 1)

12.2 mmole of copper iodide (CuI) and 92 mmole of sodium hydroxide (NaOH) were added to a solution of 0.3 mole of 2-(2-methoxyethoxyl)ethanol in 20 mL of dry pyridine, with stirring at ambient temperature for 30 min. 61 mmole of 2-bromothiophene was then added and the solution was heated to 100° C. for 7 days. The mixture was then cooled to ambient temperature and poured into a mixture of water and dichloromethane. Next, the organic solution was extracted 3 times with a 10%/HCl solution to remove the pyridine, then with water. The organic phase was then dried over $Na_2SO_4$ and the dichloromethane was evaporated off under vacuum. The impure product was purified on a chromatographic column with a cyclohexane/ethyl acetate (80/20) mixture as the eluent in order to obtain the compound 1 in the form of a colourless oil (Yield=34%).

$^1$H NMR ($CDCl_3$, 300 MHz): 3.39 (s, 3H); 3.58 (dd; $^3J=5.0$ Hz, $^3J=6.4$ Hz, 2H); 3.71 (dd, $^3J=5.0$ Hz, $^3J=6.4$ Hz, 2H); 3.84 (t, $^3J=4.7$ Hz, 2H); 4.2 (t, $^3J=4.7$ Hz, 2H); 6.24 (dd, $^3J=5.8$ Hz, $^4J=1.3$ Hz, 1H); 6.55 (dd, $^3J=3.7$ Hz, $^4J=1.3$ Hz, 1H); 6.70 (q, $^3J=5.8$ Hz, $^3J=3.7$ Hz, 1H).

$^{13}$C NMR ($CDCl_3$, 50 MHz): 59.1; 69.4; 70.8; 71.9; 73.1; 105.2; 112.2; 124.6; 165.3.

ESI-MS: 202.1 ([M], 100).

Elemental analysis for $C_9H_{14}O_3S$:

|  | C | H |
|---|---|---|
| Calculated | 53.44 | 6.98 |
| Found | 53.25 | 6.84 |

2) Second Step: Synthesis of 2-trimethyltin-5-(2-(2-methoxyethoxy)-ethoxy)thiophene (Compound 2)

A solution of 2.5M of n-butyl-lithium (nBuLi) in hexane (15.2 mmol) was slowly added to a solution of 13.8 mmol of compound 1 obtained as above in the preceding step in 40 mL of dry THF at −78° C. The solution was stirred for 1 hour at −78° C. and a solution of trimethyltin chloride (1.0 M in THF, 18 mmol) was then added. The solution was heated up to ambient temperature and stirred for 12 hours. Next, the solution was poured into water and the product was extracted with ethyl acetate. The organic phase was washed 3 times with water then dried over $Na_2SO_4$. The ethyl acetate was evaporated off under vacuum. The impure product (Compound 2) was used in the next step without further purification.

$^1$H NMR ($CDCl_3$, 300 MHz): 0.32 (s, 9H); 3.39 (s, 3H); 3.58 (dd, $^3J$=4.9 Hz, $^3J$=6.4 Hz, 2H); 3.71 (dd, $^3J$=4.9 Hz, $^3J$=6.4 Hz, 2H); 3.84 (t, $^3J$=5.0 Hz, 2H); 4.21 (t, $^3J$=4.7 Hz, 2H); 6.37 (d, $^3J$=3.5 Hz, 1H); 6.79 (d, $^3J$=3.5 Hz, 1H).

$^{13}$C NMR ($CDCl_3$, 50 MHz): −8.3; 59.1; 69.5; 70.8; 72.0; 73.2; 107.1; 123.0; 133.2; 170.7.

3) Third Step: Synthesis of 5-(2-(2-methoxy-ethoxy)-ethoxy)-2,2'-bithiophene (Compound 3)

6.7 mmol of compound 2 obtained as above in the preceding step and 6.1 mmol of 2-bromothiophene were dissolved in 25 mL of dry THF and the solution was degassed with argon. Tetrakis(triphenylphosphine)palladium $[Pd(PPh_3)_4]$ was added in a catalytic quantity and the mixture was heated to 80° C. for 48 hours, with stirring and under argon. The solution was then cooled to ambient temperature and filtered over celite. The organic phase was washed 3 times with water then dried over $Na_2SO_4$. The ethyl acetate was evaporated off under vacuum. The impure product was purified on a chromatographic column with a cyclohexane/ethyl acetate mixture (80/20) to obtain the expected compound 3 in the form of a pale yellow oil (yield=65%).

$^1$H NMR (Acetone d6, 300 MHz): 3.31 (s, 3H); 3.52 (dd, $^3J$=5.5 Hz, $^3J$=6.7 Hz, 2H); 3.64 (dd, $^3J$=5.5 Hz, $^3J$=6.7 Hz, 2H); 3.81 (m, 2H); 4.24 (m, 2H); 6.28 (d, $^3J$=3.9 Hz, 1H); 6.89 (d, $^3J$=3.9 Hz, 1H); 7.03 (q, $^3J$=5.1 Hz, $^3J$=5.1 Hz, 1H); 7.09 (dd, $^3J$=3.5 Hz, $^4J$=1.1 Hz, 1H); 7.31 (dd, $^3J$=5.1 Hz, $^4J$=1.1 Hz, 1H).

$^{13}$C NMR (Acetone d6, 50 MHz): 58.8; 69.9; 71.2; 72.7; 74.1; 106.6; 122.4; 123.2; 124.4; 124.5; 128.7; 138.6; 165.3.

ESI-MS: 248.4 ([M], 100).

Elemental analysis for $C_{13}H_{16}O_3S_2$:

|  | C | H |
|---|---|---|
| Calculated | 54.90 | 5.67 |
| Found | 54.68 | 5.74 |

4) Fourth Step: Synthesis of Compound 4

Compound 4 was synthesised following general procedure n°4, starting from 600 mg (2.1 mmol, 1 eq) of compound 3 obtained as above in the preceding step and 300 μL of phosphorus oxychloride ($POCl_3$) (3.15 mmol, 1.5 eq). An 80/20 petroleum ether/ethyl acetate mixture was used to purify the desired compound. 480 mg (1.53 mmol, yield: 73%) of compound 4 was obtained.

$^1$H NMR (200 MHz, $CDCl_3$): 3.39 (s, 3H); 3.55-3.60 (m, 2H); 3.67-3.72 (m, 2H); 3.83-3.87 (m, 2H); 4.22-4.26 (m, 2H); 6.21 (d, 1H, $^3J$=4.1 Hz); 7.01-7.05 (m, 2H); 7.61 (d, 1H, $^3J$=4.1 Hz); 9.80 s, 1H).

$^{13}$C NMR ($CDCl_3$, 50 MHz): 59.2; 69.4; 71.0; 72.1; 73.3; 106.6; 122.6; 122.8; 124.6; 137.7; 140.5; 148.4; 166.9; 182.4.

ESI-MS: 312.1 ([M], 100).

Elemental analysis for $C_{14}H_{16}O_4S_2$:

|  | C | H |
|---|---|---|
| Calculated | 53.82 | 5.16 |
| Found | 53.69 | 5.04 |

5) Fifth Step: Synthesis of Compounds B2 and B3

Compounds B2 and B3 were synthesized by following general procedure n°1, starting from 360 mg (0.8 mmol, 1 eq) of compound B1 and 250 mg (0.8 mmol, 1 eq) of compound 4 as obtained as above in the preceding step in a volume of 20 mL of toluene. A 70/30 mixture of petroleum ether/ethyl acetate (v/v) was used to purify the desired compounds. 78 mg of compound B3 (0.1 mmol, yield 13%) and 510 mg (0.49 mmol, yield 61%) of compound B2 were obtained.

Compound B3: $^1$H NMR (300 MHz, $CDCl_3$): 1.43 (s, 3H); 1.46 (s, 3H); 2.6 (s, 3H); 3.41 (s, 3H); 3.58-3.61 (m, 2H); 3.71-3.74 (m, 2H); 3.85-3.88 (m, 2H); 4.23-4.26 (m, 2H); 6.01 (s, 1H); 6.19 (d, 1H, $^3J$=4.0 Hz); 6.56 (s, 1H); 6.88 (d, 1H, $^3J$=4.0 Hz): 6.92 (d, 1H, J=4.0 Hz); 7.05 (d, 1H, $^3J$=4.0 Hz), 7.07 (d, 2H, $^3J$=8.2 Hz); 7.27 (d, 1H, $^3J$=16.0 Hz); 7.35 (d, 1H, $^3J$=16.0 Hz); 7.86 (d, 2H, $^3J$=8.2 Hz).

$^{13}$C NMR (50 MHz, $CDCl_3$): 14.8; 15.1; 59.2; 69.5; 70.9; 72.1; 73.3; 94.9; 106.4; 117.7; 118.1; 121.5; 122.4; 122.9; 124.2; 129.2; 129.9; 130.4; 134.8; 138.1; 138.4; 140.1; 140.2; 142.2; 152.8; 155.5; 165.1; 196.1.

ESI-MS: 744.1 ([M], 100).

Elemental analysis for $C_{33}H_{32}BF_2IN_2O_3S_2$:

|  | C | H | N |
|---|---|---|---|
| Calculated | 53.24 | 4.33 | 3.76 |
| Found | 53.04 | 4.17 | 3.54 |

Compound B2: $^1$H NMR (300 MHz, $CDCl_3$): 1.47 (s, 6H); 3.41 (s, 6H); 3.58-3.61 (m, 4H); 3.71-3.74 (m, 4H); 3.86-3.89 (m, 4H); 4.24-4.27 (m, 4H); 6.22 (d, 2H, $^3J$=4.0 Hz); 6.59 (s, 2H); 6.93 (d, 2H, $^3J$=2.7 Hz); 6.95 (d, 2H, $^3J$=2.7 Hz); 7.07-7.10 (m, 4H); 7.29 (superimposed with the solvent, d, 2H, $^3J$=16.0 Hz); 7.43 (d, 2H, $^3J$=16.0 Hz); 7.85 (d, 2H, $^3J$=8.2 Hz).

$^{13}$C NMR (50 MHz, $CDCl_3$): 15.1; 59.2; 69.5; 70.9; 72.1; 73.2; 94.8; 106.4; 117.9; 118.3; 122.5; 123.1; 124.2; 129.1; 129.8; 130.7; 135.0; 138.4; 140.2; 141.4; 152.2; 165.1.

ESI-MS: 1038.1 ([M], 100).

Elemental analysis for $C_{47}H_4BF_2IN_2O_6S_4$:

|  | C | H | N |
|---|---|---|---|
| Calculated | 54.34 | 4.46 | 2.70 |
| Found | 54.47 | 4.38 | 2.52 |

Example 2

Synthesis of Compounds B4 and B5

Compounds B4 and B5 were synthesized in accordance with the following synthesis scheme:

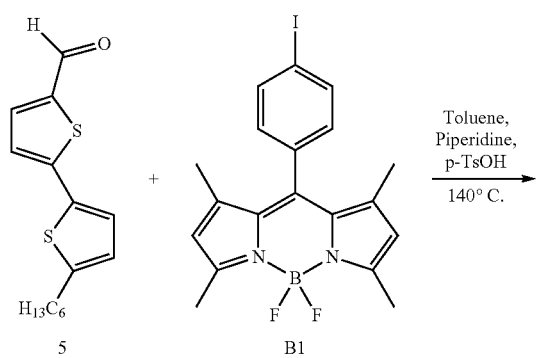

Compounds B4 and B5 were synthesized by following general procedure n°1, starting from 310 mg (0.69 mmol, 1 eq) of compound B1, 287 mg (1.05 mmol, 1.5 eq) of compound 5 in a volume of 20 mL of toluene. A 70/10/20 (v/v/v) petroleum ether/$CH_2Cl_2$/toluene mixture was used to purify the desired compounds. 402 mg of compound B4 (0.41 mmol, yield: 60%) and 74 mg (0.1 mmol, yield 15%) of compound B5 were obtained.

Compound B4: $^1$H NMR (300 MHz, $CDCl_3$): 0.91 (t, 6H, $^3J$=6.6 Hz); 1.26-1.43 (m, 12H); 1.47 (s, 6H); 1.69 (m, 4H); 2.82 (t, 4H, $^3J$=7.4 Hz); 6.60 (s, 2H); 6.73 (d, 2H, $^3J$=3.3 Hz); 7.04-7.12 (m, 8H); 7.30 (superimposed with the solvent d, 2H, $^3J$=16.0 Hz); 7.45 (d, 2H, $^3J$=16.0 Hz); 7.85 (d, 2H, 3J=8.1 Hz).

$^{13}$C NMR (50 MHz, $CDCl_3$): 14.2; 15.1; 22.7; 28.9; 30.4; 31.7; 31.8; 94.8; 118.0; 118.3; 123.9; 124.4; 125.2; 129.1; 129.8; 130.8; 133.6; 134.8; 135.0; 135.8; 138.4; 140.1; 140.7; 141.5; 146.6; 152.3.

ESI-MS: 970.1 ([M], 100).

Elemental analysis for $C_{49}H_{50}BF_2IN_2S_4$:

|  | C | H | N |
| --- | --- | --- | --- |
| Calculated | 60.62 | 5.19 | 2.89 |
| Found | 60.52 | 4.97 | 2.70 |

Compound B5: $^1$H NMR (200 MHz, $CDCl_3$): 0.87-0.93 (m, 3H); 1.26-1.34 m, 6H); 1.43 (s, 3H); 1.46 (s, 3H); 1.59-1.69 (m, 2H); 2.60 (s, 3H); 2.81 (t, 2H, $^3J$=6.9 Hz); 6.02 (s, 1H); 6.56 (s, 1H): 6.70 (d, 1H, $^3J$=3.3 Hz); 7.01-7.09 (m, 5H); 7.23-7.43 (superimposed with the solvent, m, 2H): 7.85 (d, 2H, $^3J$=8.4 Hz).

$^{13}$C NMR (50 MHz, $CDCl_3$): 14.2; 14.8; 15.1; 22.7; 28.9; 29.8; 30.4; 31.6; 31.7; 94.8; 117.8; 117.9; 118.0; 118.1; 121.5; 1216; 123.7; 124.3; 125.2; 129.2; 129.8; 130.4; 134.7; 134.9; 138.4; 140.0; 140.5; 142.2; 142.4; 146.6; 152.7; 152.8; 155.6; 155.7.

ESI-MS: 710.1 ([M], 100).

Elemental analysis for $C_{34}H_{34}BF_2N_2S_2$:

|  | C | H | N |
| --- | --- | --- | --- |
| Calculated | 57.48 | 4.82 | 3.94 |
| Found | 57.31 | 4.62 | 3.72 |

Example 3

Synthesis of Compound B6

Compound B6 was synthesized in accordance with the following synthesis scheme:

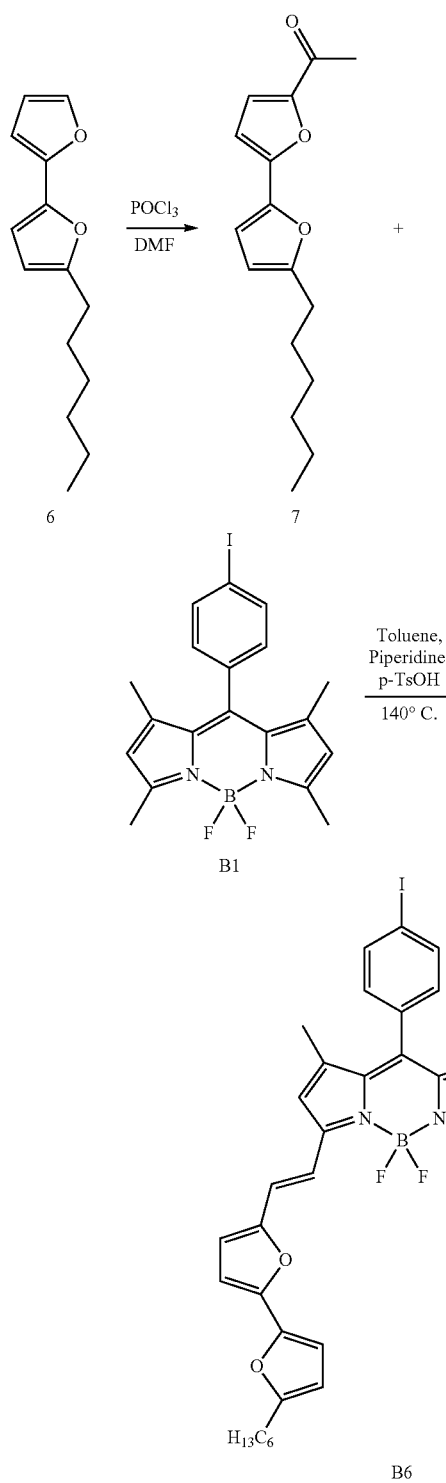

1) First Step: Synthesis of Compound 7

The compound 7 was synthesized by following general procedure n°4, starting from 900 mg (2.1 mmol, 1 eq) of compound 6 and 575 μL of POCl$_3$ (3.15 mmol, 1.5 eq). A 50/50 (v/v) petroleum ether/CH$_2$Cl$_2$ mixture was used to purify the desired compound. 600 mg (2.43 mmol, 60%) of the expected compound 7 was obtained.

$^1$H NMR (300 MHz, CDCl$_3$): 0.90 (t, 3H, $^3$J=6.6 Hz); 1.29-1.40 (m, 6H); 1.66-1.71 (m, 2H); 2.68 (t, 2H, J=7.6 Hz); 6.14 (d, 1H, $^3$J=3.3 Hz); 6.66 (d, 1H, $^3$J=3.6 Hz); 6.82 (d, 1H, $^3$J=3.3 Hz); 7.29 (d, 1H, $^3$J=3.6 Hz); 9.59 (s, 1H).

$^{13}$C NMR (50 MHz, CDCl$_3$): 14.2; 22.7; 28.0; 28.3; 28.9; 31.6; 106.6; 107.7; 110.9; 123.9; 143.3; 151.4; 152.1; 159.3; 176.9; 195.8.

ESI-MS: 246.1 ([M], 100).

Elemental analysis for C$_{15}$H$_{18}$O$_3$:

|  | C | H |
|---|---|---|
| Calculated | 73.15 | 7.37 |
| Found | 73.01 | 7.21 |

2) Second Step: Synthesis of Compound B6

Compound B6 was synthesized by following general procedure n°1, starting from 200 mg (0.46 mmol, 1 eq) of B1, 260 mg (1.05 mmol; 2.3 eq) of compound 7 obtained as above in the preceding step in a volume of 20 mL of toluene. A 10/40/50 CH$_2$Cl$_2$/toluene/petroleum ether (v/v/v) mixture was used to purify the desired compound. 250 mg of compound B6 (0.27 mmol, yield: 60%) was obtained.

$^1$H NMR (300 MHz, CDCl$_3$): 0.91 (t, 6H, $^3$J=6.6 Hz); 1.30-1.42 (m, 12H); 1.48 (s, 6H); 1.65-1.73 (m, 4H): 2.70 (t, 4H, $^3$J=7.3 Hz); 6.09 (d, 2H, $^3$=3.3 Hz); 6.59-6.71 (m, 8H); 7.02 (d, 2H, $^3$J=16.2 Hz); 7.10 (d, 2H, $^3$J=8.2 Hz); 7.60 (d, 2H, $^3$J=16.2 Hz); 7.85 (d, 2H, $^3$J=8.2 Hz).

$^{13}$C NMR (50 MHz, CDCl$_3$): 14.2; 15.1; 22.7; 28.1; 28.3; 29.0; 31.7; 94.8; 107.3; 108.1; 114.5; 116.8; 118.2; 122.7; 130.8; 135.1; 138.3; 141.3; 144.6; 148.4; 152.2; 157.5.

ESI-MS: 906.2 ([M], 100).

Elemental analysis for C$_{49}$H$_{50}$BF$_2$IN$_2$O$_4$:

|  | C | H | N |
|---|---|---|---|
| Calculated | 64.91 | 5.56 | 3.09 |
| Found | 64.71 | 5.34 | 2.78 |

Example 4

Synthesis of Compound B7

Compound B7 was synthesized in accordance with the following synthesis scheme:

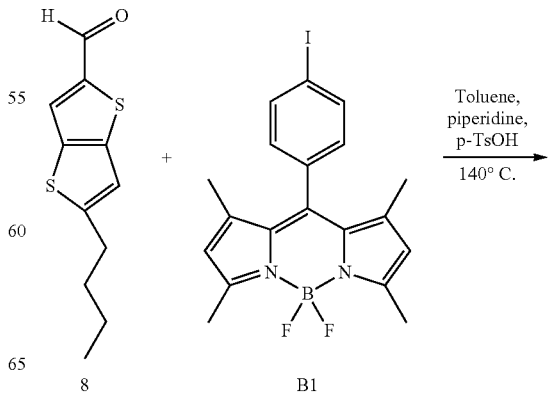

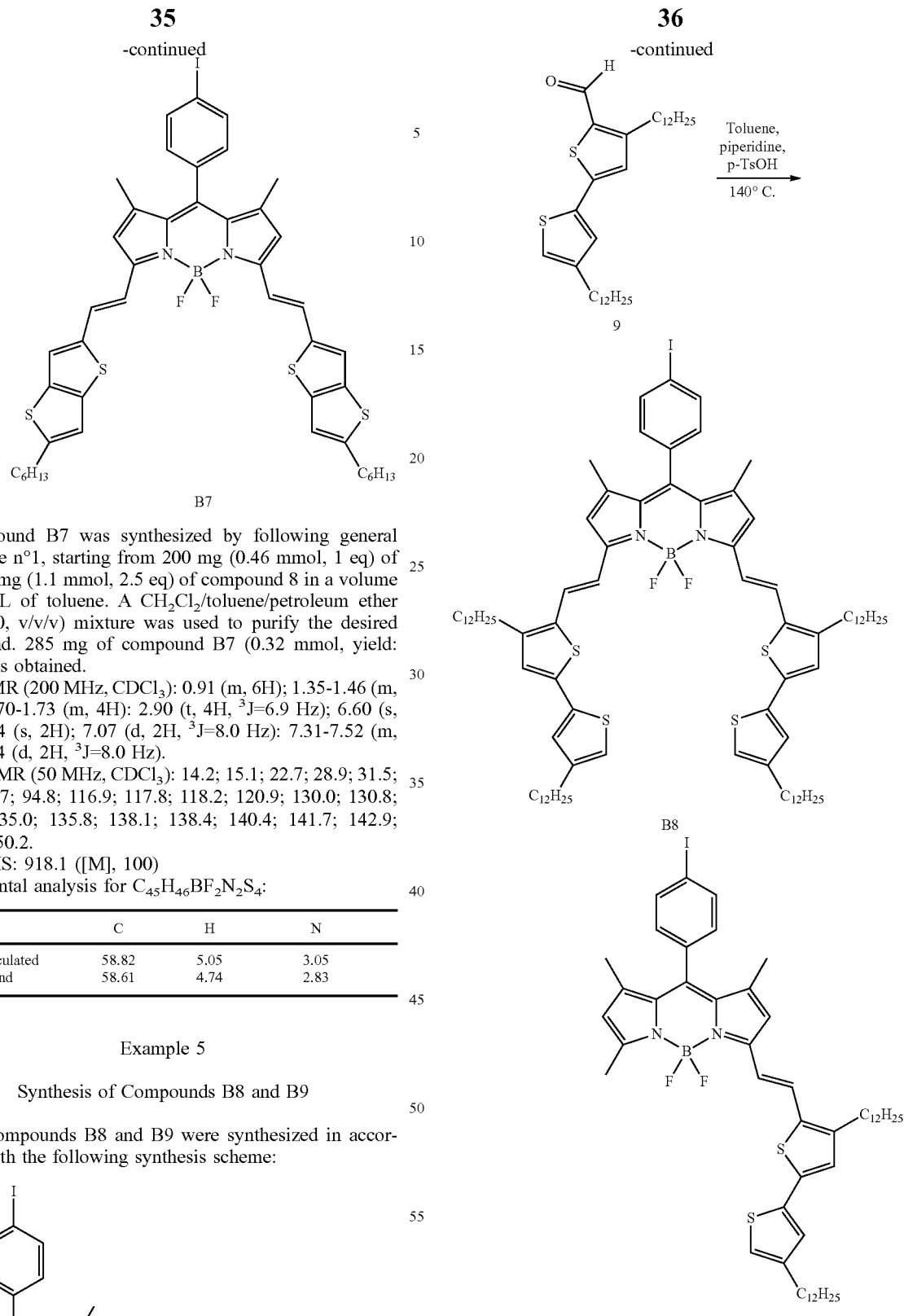

B7

Compound B7 was synthesized by following general procedure n°1, starting from 200 mg (0.46 mmol, 1 eq) of B1, 280 mg (1.1 mmol, 2.5 eq) of compound 8 in a volume of 20 mL of toluene. A CH$_2$Cl$_2$/toluene/petroleum ether (10/40/50, v/v/v) mixture was used to purify the desired compound. 285 mg of compound B7 (0.32 mmol, yield: 70%) was obtained.

$^1$H NMR (200 MHz, CDCl$_3$): 0.91 (m, 6H); 1.35-1.46 (m, 18H); 1.70-1.73 (m, 4H); 2.90 (t, 4H, $^3$J=6.9 Hz); 6.60 (s, 2H); 6.94 (s, 2H); 7.07 (d, 2H, $^3$J=8.0 Hz): 7.31-7.52 (m, 6H); 7.84 (d, 2H, $^3$J=8.0 Hz).

$^{13}$C NMR (50 MHz, CDCl$_3$): 14.2; 15.1; 22.7; 28.9; 31.5; 31.6; 31.7; 94.8; 116.9; 117.8; 118.2; 120.9; 130.0; 130.8; 133.5; 135.0; 135.8; 138.1; 138.4; 140.4; 141.7; 142.9; 151.0; 150.2.

ESI-MS: 918.1 ([M], 100)

Elemental analysis for C$_{45}$H$_{46}$BF$_2$N$_2$S$_4$:

|  | C | H | N |
|---|---|---|---|
| Calculated | 58.82 | 5.05 | 3.05 |
| Found | 58.61 | 4.74 | 2.83 |

Example 5

Synthesis of Compounds B8 and B9

The compounds B8 and B9 were synthesized in accordance with the following synthesis scheme:

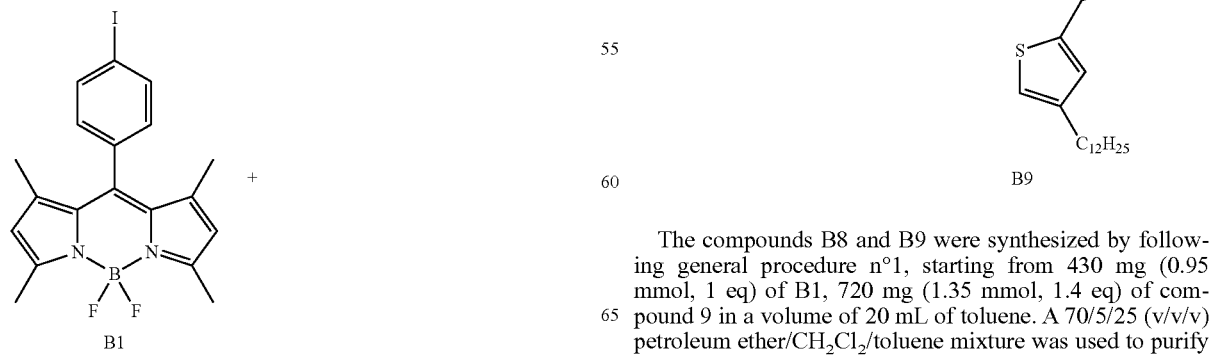

The compounds B8 and B9 were synthesized by following general procedure n°1, starting from 430 mg (0.95 mmol, 1 eq) of B1, 720 mg (1.35 mmol, 1.4 eq) of compound 9 in a volume of 20 mL of toluene. A 70/5/25 (v/v/v) petroleum ether/CH$_2$Cl$_2$/toluene mixture was used to purify the desired compounds. 260 mg of compound B8 (0.176 mmol, yield 18%) and 140 mg (0.145 mmol, yield 15%) of compound B9 were obtained.

Compound B8: $^1$H NMR (300 MHz, CDCl$_3$): 0.88 (t, 12H, $^3$J=6.35 Hz); 1.26 (m, 72H); 1.49 (s, 6H); 1.60-1.65 (m, 8H); 2.60 (t, 4H, $^3$J=7.5 Hz); 2.68 (t, 4H, $^3$J=7.5 Hz); 6.61 (s, 2H); 6.83 (s, 2H); 6.97 (s, 2H); 7.10 (d, 2H, $^3$J=8.3 Hz); 7.15 (s, 2H); 7.40 (s, 4H); 7.85 (d, 2H, $^3$J=8.3 Hz).

$^{13}$C NMR (50 MHz, CDCl$_3$): 14.3, 15.1, 22.8, 28.8, 29.5, 29.6, 29.7, 29.8, 30.5, 30.6, 31.1, 32.1, 94.8, 117.4, 118.3, 119.9, 126.0, 127.3, 130, 119.9, 126.0, 127.3, 130.9, 133.6, 135.1, 135.5, 137.1, 138.4, 141.2, 144.5, 145.4, 152.5.

ESI-MS: 1474.7 ([M], 100).

Elemental analysis for C$_{85}$H$_{122}$BF$_2$IN$_2$S$_4$:

|  | C | H | N |
|---|---|---|---|
| Calculated | 69.17 | 8.33 | 1.90 |
| Found | 69.04 | 8.17 | 1.74 |

Compound B9: $^1$H NMR (300 MHz, CDCl$_3$): 0.88 (m, 6H); 1.26-1.34 (m, 36H); 1.44 (s, 3H); 1.48 (s, 3H); 1.55-1.65 (m, 4H); 2.56-2.66 (m, 7H); 6.01 (s, 1H); 6.58 (s, 1H); 6.83 (s, 1H); 7.06-7.09 (m, 3H); 7.36 (s, 2H); 7.85 (d, 2H, $^3$J=8.2 Hz);

$^{13}$C NMR (50 MHz, CDCl$_3$): 14.3; 14.8; 15.1; 22.8; 28.8; 29.4; 29.5; 29.6; 29.7; 29.8; 30.5; 30.6; 31.1; 32.1; 94.8; 117.2; 118.0; 119.9; 121.4; 125.9; 126.1; 127.5; 128.9; 130.4; 131.1; 131.6; 134.9; 135.2; 137.0; 138.3; 138.4; 142.0; 142.2; 144.5; 145.4; 153.2; 155.2.

ESI-MS: 962.4 ([M], 100)

Elemental analysis for C$_{52}$H$_{70}$BF$_2$IN$_2$S$_2$:

|  | C | H | N |
|---|---|---|---|
| Calculated | 64.86 | 7.33 | 2.91 |
| Found | 64.97 | 7.52 | 3.05 |

Example 6

Synthesis of Compounds B10 and B11

The compounds B10 and B11 were synthesized in accordance with the following synthesis scheme:

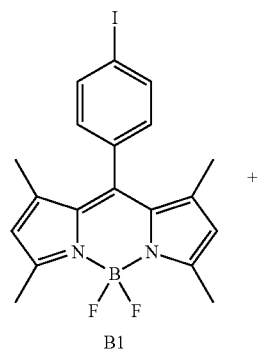

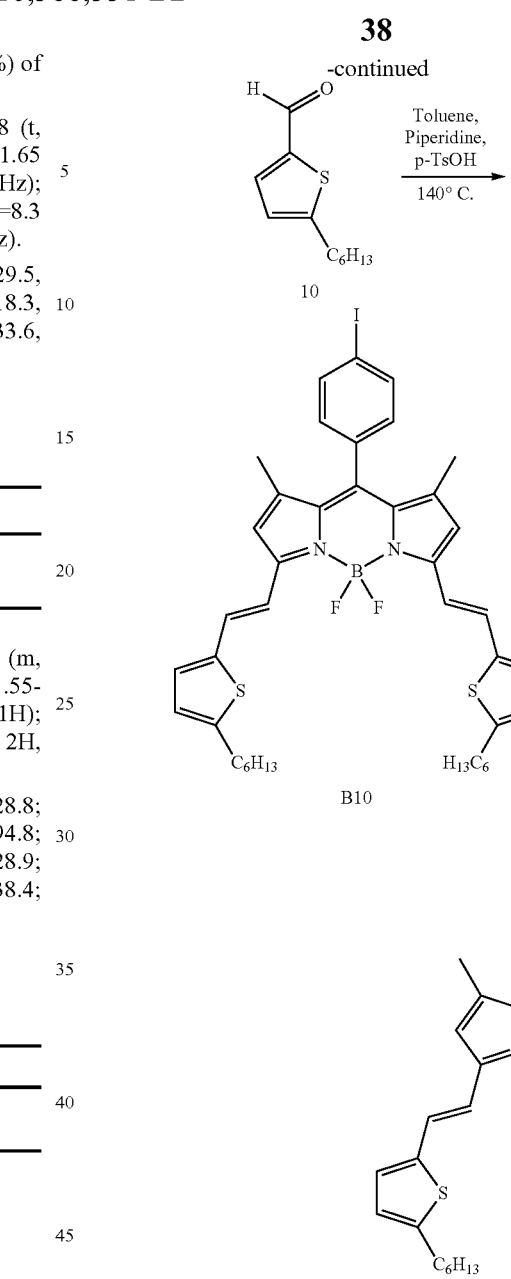

The compounds B10 and B11 were synthesized by following general procedure n°1, starting from 434 mg (0.97 mmol, 1 eq) of B1, 223 mg (1.44 mmol, 1.5 eq) of compound 10 in a volume of 20 mL of toluene. A 70/5/25 (v/v/v) petroleum ether/CH$_2$Cl$_2$/toluene mixture was used to purify the desired compounds. 196 mg of compound B10 (0.243 mmol, yield: 25%) and 55 mg (0.088 mmol, yield 9%) of compound B11 were obtained.

Compound B10: $^1$H NMR (300 MHz, CDCl$_3$): 0.88-0.93 (m, 6H); 1.33-1.42 (m, 12H); 1.45 (s, 6H); 1.67-1.74 (m, 4H); 2.83 (t, 4H, $^3$J=7.6 Hz); 6.56 (s, 2H); 6.72 (d, 2H, $^3$J=3.8 Hz); 7.04 (d, 2H, $^3$J=3.8 Hz); 7.08 (d, 2H, $^3$J=8.1 Hz); 7.27-7.42 (m, 4H); 7.84 (d, 2H, $^3$J=8.1 Hz).

$^{13}$C NMR (50 MHz, CDCl$_3$): 14.0; 14.9; 22.8; 28.8; 30.7; 31.5; 31.6; 94.6; 117.3; 117.9; 125.1; 125.3; 128.6; 129.5; 130.6; 134.9; 138.2; 140.1; 141.2; 149.0; 152.5.

ESI-MS: 806.1 ([M], 100).

Elemental analysis for $C_{41}H_{46}BF_2IN_2S_2$:

|  | C | H | N |
|---|---|---|---|
| Calculated | 61.05 | 5.75 | 3.47 |
| Found | 60.81 | 5.44 | 3.21 |

Compound B11: $^1$H NMR (300 MHz, CDCl$_3$): 0.90 (t, 3H, $^3$J=6.3 Hz); 1.33 (s, 6H): 1.42-1.45 (m, 6H): 1.65-1.72 (m, 2H): 2.58 (s, 3H); 2.81 (t, 2H, $^3$J=7.5 Hz); 6.00 (s, 1H); 6.54 (s, 1H); 6.70 (d, 1H, $^3$J=3.5 Hz); 7.01 (d, 1H, $^3$J=3.5 Hz); 7.06 (d, 2H, $^3$J=8.2 Hz); 7.31 (s, 2H); 7.84 (d, 2H, $^3$J=8.2 Hz).

$^{13}$C NMR (50 MHz CDCl$_3$) 14.2; 14.8; 15.0; 22.7; 28.9; 29.8; 30.8; 31.6; 31.7; 95.0; 117.2; 117.9; 121.4; 125.4; 129.0; 130.0; 130.4; 131.5; 132.8; 134.9; 138.1; 138.4; 140.1; 142.0; 142.4; 149.3; 153.3; 155.2.

ESI-MS: 628.0 ([M], 100).

Elemental analysis for $C_{30}H_{32}BF_2IN_2S$:

|  | C | H | N |
|---|---|---|---|
| Calculated | 57.34 | 5.13 | 4.46 |
| Found | 57.12 | 4.98 | 4.31 |

Example 7

Synthesis of Compounds B12 and B13

The compounds B12 and B13 were synthesized in accordance with the following synthesis scheme:

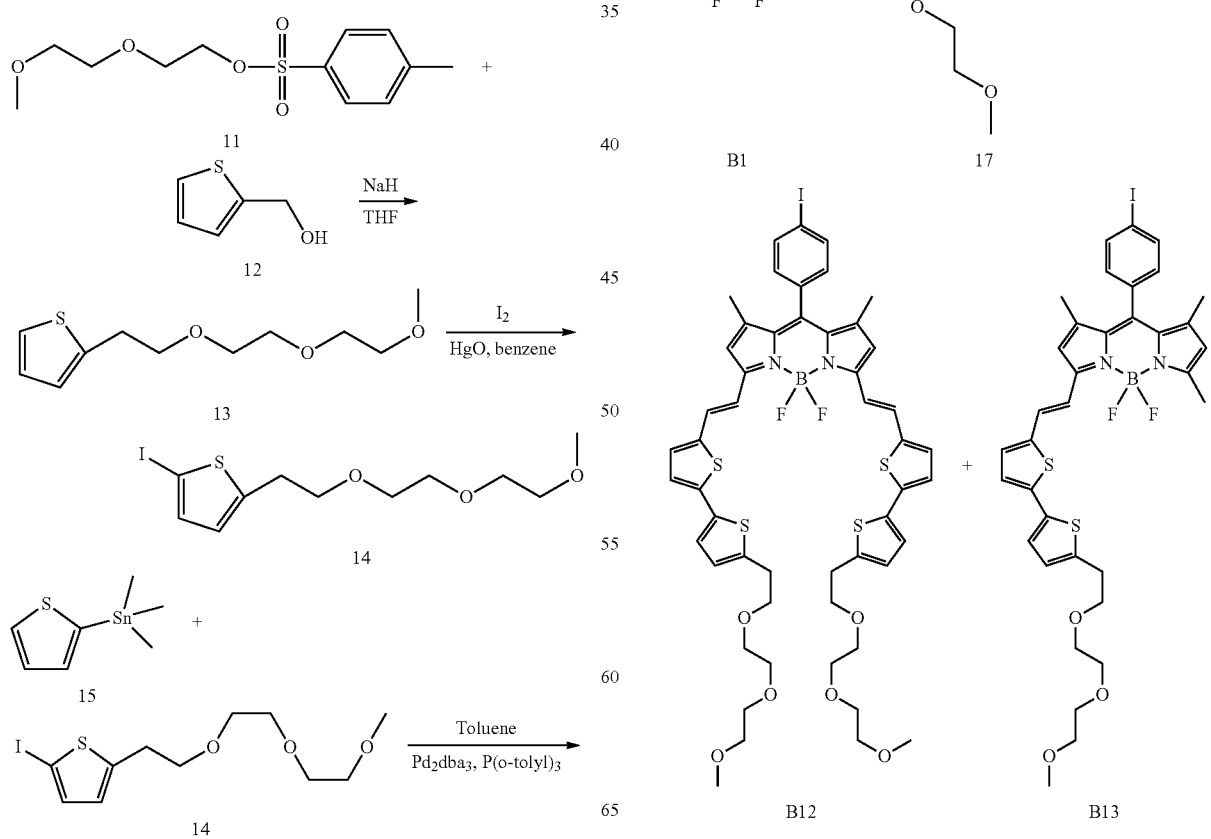

1) First Step: Synthesis of Compound 13

1.750 mmol of 2-thiophene ethanol (compound 12) under argon was added to a suspension of sodium hydride (2.044 mmol) in 5 mL of freshly distilled tetrahydrofuran. The solution was stirred for 45 min, after which 2-(2-methoxy-ethoxyl)ethyl 4-methylbenzenesulphonate (compound 11; 1.460 mmol) was added dropwise. Stirring at ambient temperature was maintained overnight. The reaction medium was acidified using a hydrochloric acid solution until the pH reached 7. The solution was then washed with water and extracted with ethyl acetate. Compound 13 was obtained in the form of a yellow oil after purification using silica gel chromatography with a mixture of solvents as the eluent (petroleum ether/ethyl acetate 8/2: v/v) in a yield of 75%.

$^1$H NMR (300 MHz, $(CD_3)_2CO$, δ (ppm): 3.06 (t, 2H, $^3J$=6.7 Hz); 3.28 (s, 3H); 3.46 (m, 2H); 3.57 (m, 6H); 3.67 (t, 2H, J=6.7 Hz), 6.91 (m, 2H); 7.23 (dd, 1H, $^3J$=8.0 Hz, $^4J$=1.4 Hz).

$^{13}$C NMR (75 MHz, $(CD_3)_2CO$, δ (ppm): 30.0; 58.8; 71.0; 71.1; 71.2; 72.4; 72.7; 124.4; 126.0; 127.4; 142.4.

ESI-MS: 230.1 (100).

Elemental analysis for $C_{11}H_{18}O_3S$:

|  | C | H |
|---|---|---|
| Calculated | 57.36 | 7.88 |
| Found | 57.01 | 7.53 |

2) Second Step: Synthesis of 2-iodo-5-(2-(2-(2-methoxyethoxy)ethoxy)ethyl)-thiophene (Compound 14)

Mercury oxide (0.456 mmol) and iodine (0.456 mmol) at 0° C. were added alternately and in small portions to a solution of 100 mg of compound 13 obtained as above in the preceding step (0.434 mmol) in a solution of benzene (10 mL). The solution was stirred at ambient temperature for 1 hour before being filtered over celite. The organic phase was washed with the aid of a solution of sodium thiosulphate and the aqueous phase was extracted with ether. The compound 14 was obtained in a yield of 87%, in the form of a yellow oil after purification by silica gel chromatography with a mixture of solvents as the eluent (6/4 petroleum ether/ethyl acetate).

$^1$H NMR (300 MHz, $(CD_3)_2CO$): 3.07 (t, 2H, $^3J$=6.5 Hz); 3.39 (s, 3H); 3.61 (m, 10H); 6.54 (d, 1H, $^3J$=3.7 Hz); 7.04 (d, 1H, $^3J$=3.7 Hz).

$^{13}$C NMR (75 MHz, $(CD_3)_2CO$): 30.1; 50.8; 71.0; 71.1; 71.2; 71.9; 72.7; 126.0; 128.1; 137.5; 149.4.

ESI-MS: 356.0 (100).

Elemental analysis for $C_{11}H_{17}IO_3S$:

|  | C | H |
|---|---|---|
| Calculated | 37.09 | 4.81 |
| Found | 36.90 | 4.62 |

3) Third Step: Synthesis of 5-(2-(2-(2-methoxy-ethoxyl)ethoxy)ethyl)-2,2'-bithiophene (Compound 16)

1.68 mmol of 2-trimethyltinthiophene, 0.9 mmol of compound 14 obtained as above in the preceding step and 6.75·10$^{-5}$ mol of tri(o-tolyl)phosphine were dissolved in 5 mL of dry toluene and the solution was degassed with the aid of argon. 1.7·10$^{-5}$ mol of tris(dibenzylideneacetone)dipalladium [$Pd_2(dba)_3$] were then added and the mixture was heated at 110° C. for 24 hours with stirring and under argon. The solution was then brought back to ambient temperature then filtered over celite. The organic phase was washed 3 times with water, then dried over $Na_2SO_4$. The ethyl acetate was evaporated off under vacuum. The impure product was purified on a flash chromatographic column with a cyclohexane/ethyl acetate mixture (80/20) to obtain the compound 16 in the form of a pale yellow oil (Yield=63%).

$^1$H NMR (CDCl$_3$, 300 MHz): 3.07 (t, 2H, $^3J$=6.8 Hz); 3.85 (s, 3H); 3.53-3.57 (m, 2H); 3.63-3.76 (m, 8H); 6.74-6.76 (m, 1H); 6.97-7.01 (m, 2H); 7.09-7.11 (m, 1H); 7.16-7.19 (m, 1H).

$^{13}$C NMR (CDCl$_3$, 50 MHz): 30.7; 59.1; 70.5; 70.7; 71.8; 72.1; 123.2; 123.5; 123.9; 126.0; 127.7; 135.7; 137.9; 140.8.

ESI-MS: 312.1 (100).

Elemental analysis for $C_{15}H_{20}O_3S_2$:

|  | C | H |
|---|---|---|
| Calculated | 57.66 | 6.45 |
| Found | 57.52 | 6.51 |

4) Fourth Step: Synthesis of Compound 17

Compound 17 was synthesized by following general procedure n°4, starting from 150 mg (0.476 mmol, 1 eq) of compound 16 obtained as above in the preceding step and 67 μL of POCl$_3$ (0.714 mmol, 1.5 eq). An 80/20 dichloromethane ether/ethyl acetate mixture was used to purify the desired compound. 91 mg (0.266 mmol, yield 56%) of compound 17 was obtained.

$^1$H NMR (200 MHz, (CDCl$_3$), δ (ppm): 3.06 (t, 3H, $^3J$=6.5 Hz): 3.35 (s, 3H); 3.61 (m, 10H); 6.78 (d, 1H, $^3J$=3.6 Hz); 7.14 (m, 2H); 7.61 (d, 1H, $^3J$=3.6 Hz); 9.79 (s, 1H).

$^{13}$C NMR (50 MHz, (CD$_3$)$_2$CO, δ (ppm): 30.8; 59.0; 70.4; 70.6; 71.3; 71.9; 123.6; 126.0; 126.6; 134.2; 137.5; 141.1; 144.2; 147.7; 182.5.

ESI-MS: 340.1 (100)

Elemental analysis for $C_{16}H_{20}O_4S_2$:

|  | C | H |
|---|---|---|
| Calculated | 56.44 | 5.92 |
| Found | 56.21 | 5.74 |

5) Fifth Step: Synthesis of Compounds B12 and B13

Compounds B12 and B13 were synthesized by following general procedure n°1, starting from 106 mg (0.23 mmol, 1 eq) of B1, 120 mg (0.35 mmol, 1.5 eq) of compound 17 obtained as above in the preceding step in a volume of 20 mL of toluene. A 70/20/10 mixture of CH$_2$Cl$_2$/toluene/ethyl acetate (v/v/v) was used to purify the desired compounds. 25 mg of compound B13 (32 μmol, yield: 18%) and 140 mg (0.145 mmol, yield: 15%) of compound B12 were obtained.

Compound B13: $^1$H NMR (200 MHz, CDCl$_3$): 1.42 (s, 3H); 1.45 (s, 3H); 2.59 (s, 3H); 3.04-3.11 (m, 2H); 3.39 (s, 3H); 3.55-3.59 (m, 2H); 3.65-3.76 (m, 8H); 6.02 (s, 1H);

6.56 (s, 1H); 6.74-6.79 (m, 2H); 6.97-7.19 (m, 4H); 7.23-7.35 (superimposed with the solvent, m, 2H); 7.85 (d, 2H, $^3J$=8.4 Hz).

$^{13}$C NMR (50 MHz, CDCl$_3$): 14.8; 29.8; 30.8; 59.1; 70.5; 70.7; 71.8; 72.1; 94.8; 117.9; 121.6; 123.2; 123.5; 123.8; 124.5; 126.0; 126.4; 126.8; 127.8; 129.1; 129.8; 130.3; 134.8; 135.5; 135.7; 137.8; 138.2; 138.4; 139.7; 140.6; 140.8; 141.9; 142.2; 142.4; 152.6; 155.6.

ESI-MS: 772.1 ([M], 100).

Elemental analysis for C$_{35}$H$_{36}$BF$_2$IN$_2$O$_3$S$_2$:

|  | C | H | N |
|---|---|---|---|
| Calculated | 54.42 | 4.70 | 3.63 |
| Found | 54.21 | 4.48 | 3.34 |

Compound B12:

$^1$H NMR (300 MHz, CDCl$_3$): 1.47 (s, 6H); 3.10 (t, 4H, $^3J$=6.7 Hz); 3.39 (s, 6H); 3.55-3.58 (m, 4H); 3.66-3.69 (m, 12H); 3.75 (t, 4H, 6.7 Hz); 6.60 (s, 2H); 6.80 (d, 2H, $^3J$=3.6 Hz); 7.05-7.14 (m, 8H); 7.30 (superimposed with the solvent d, 2H, $^3J$=16.0 Hz); 7.45 (d, 2H, $^3J$=16.0 Hz); 7.85 (d, 2H, $^3J$=8.2 Hz).

$^{13}$C NMR (50 MHz, CDCl$_3$): 15.1; 30.9; 59.2; 70.5; 70.7; 71.7; 72.1; 94.8; 118.0; 118.2; 124.1; 124.3; 126.4; 129.0; 129.7; 130.7; 133.6; 134.9; 135.6; 138.3; 139.8; 140.7; 141.5; 141.9; 152.2.

ESI-MS: 1094.1 ([M], 100).

Elemental analysis for C$_{51}$H$_{54}$BF$_2$IN$_2$O$_6$S$_4$:

|  | C | H | N |
|---|---|---|---|
| Calculated | 55.94 | 4.97 | 2.56 |
| Found | 55.78 | 4.62 | 2.40 |

Example 8

Synthesis of Compound B15

Compound B15 was synthesized in accordance with the following synthesis scheme:

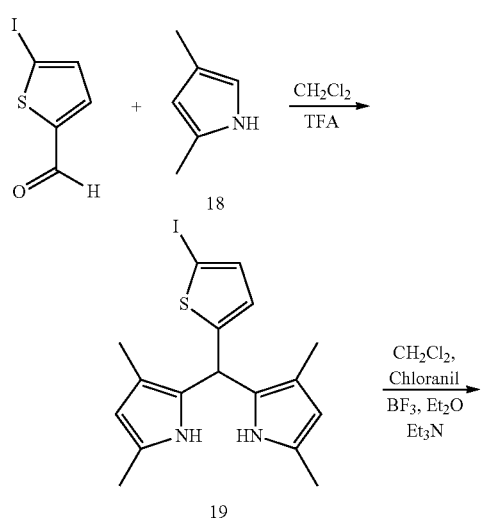

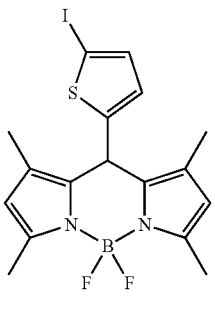

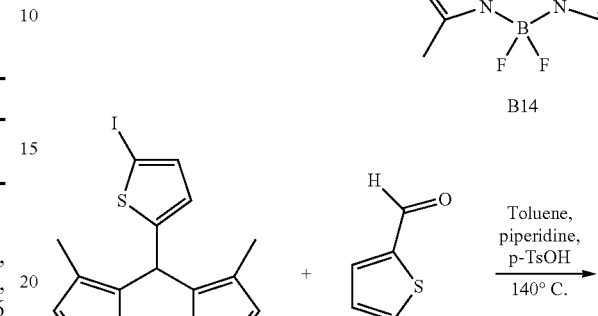

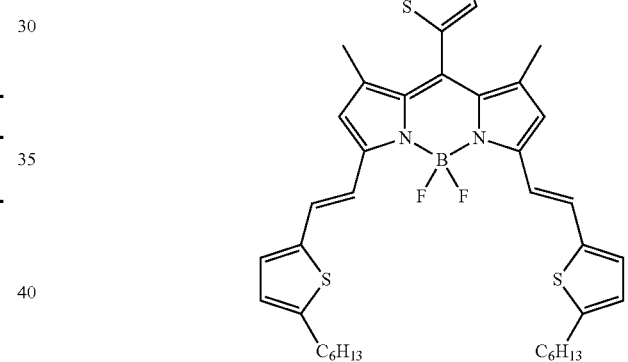

1) First Step: Synthesis of Compound 19

1.425 g (5.98 mmol, 1 eq) of 2-iodo-5-carbaldehyde thiophene, 1.257 g (12.57 mmol, 2.5 eq) of 2,4-dimethyl-pyrrole (Compound 18) and one or two drops of trifluoroacetic acid (TFA) were dissolved in a Schlenk flask containing distilled dichloromethane. The reaction mixture was stirred at ambient temperature for 2 hours. The organic phase was washed with water (3×50 mL) then dried over Na$_2$SO$_4$. A petroleum ether/CH$_2$Cl$_2$ (50/50; v/v) mixture was used to purify the desired compound. 2.138 g of compound 19 (5.20 mmol, yield: 87%) was obtained.

$^1$H NMR (300 MHz, CDCl$_3$): 1.89 (s, 6H); 2.18 (s, 6H); 5.60 (s, 1H); 5.70 (s, 2H); 6.48 (d, 1H, $^3J$=3.8 Hz); 7.09 (d, 1H, $^3J$=3.8 Hz); 7.32 (s, 2H).

$^{13}$C NMR (50 MHz CDCl$_3$): 11.1; 13.2; 14.0; 14.8; 36.1; 72.0; 108.8; 115.5; 121.8; 125.2; 126.1; 126.9; 129.8; 137.0; 137.5; 153.0; 156.6.

2) Second Step: Synthesis of Compound B14

Compound B14 was synthesized from 1.881 g (4.58 mmol, 1 eq) of compound 19 obtained as above in the preceding step which was used quickly following its purification, and 1.240 g (5.04 mmol, 1.1 eq) of 2,3,5,6-tetra-chlorocyclohexa-2,5-diene-1,4-dione (chloranil) in a volume of 60 mL of distilled dichloromethane. One hour later, 2.5 mL (27.59 mmol, 6 eq) of triethylamine then 7.16 mL (36.64 mmol, 8 eq) of etherified boron trifluoride were added. The organic phase was washed with a saturated NaHCO$_3$ solution (2×50 mL) and with water (3×50 mL), then dried over Na$_2$SO$_4$. A petroleum ether/CH$_2$Cl$_2$ (40/60; v/v) mixture was used to purify the desired compound. 0.849 g of compound B14 (1.86 mmol, yield: 41%) was obtained.

$^1$H NMR (300 MHz, CDCl$_3$): 1.67 (s, 6H); 2.55 (s, 6H); 6.01 (s, 2H); 6.69 (d, 1H, $^3$J=3.8 Hz); 7.28 (d, 1H, $^3$J=3.8 Hz).

$^{13}$C NMR (50 MHz, CDCl$_3$): 14.0; 14.8; 74.8; 121.8; 121.9; 129.8; 132.3; 132.4; 137.6; 141.1; 143.5; 156.7.

ESI-MS: 456.0 ([M], 100)

Elemental analysis for C$_{17}$H$_{16}$BF$_2$IN$_2$S:

|  | C | H | N |
|---|---|---|---|
| Calculated | 44.77 | 3.54 | 6.14 |
| Found | 44.52 | 3.24 | 5.82 |

3) Third Step: Synthesis of Compound B15

Compound B15 was synthesized by following general procedure n°1, starting from 188 mg (0.41 mmol, 1 eq) of compound B14 obtained as above in the preceding step, 208 mg (1.06 mmol, 2.6 eq) of compound 10 in a volume of 20 mL of toluene. A petroleum ether/CH$_2$Cl$_2$/toluene (70/5/25; v/v/v) mixture was used to purify the desired compound. 200 mg of compound B15 (0.246 mmol, yield: 60%) was obtained.

$^1$H NMR (300 MHz, CDCl$_3$): 0.90 (m, 6H); 1.38 (m, 12H); 1.71 (m, 10H); 2.83 (t, 4H, $^3$J=7.4 Hz); 6.59 (s, 2H); 6.72 (m, 3H); 7.04 (m, 2H); 7.28 (m, 1H); 7.33-7.40 (m, 4H).

$^{13}$C NMR (50 MHz, CDCl$_3$): 14.0; 14.1; 22.6; 28.8; 30.7; 31.5; 31.6; 117.3; 118.1; 125.3; 127.4; 128.9; 129.9; 130.2; 134.2; 137.3; 140.1; 141.5; 141.6; 149.3; 152.3.

ESI-MS: 812.1 ([M], 100).

Elemental analysis for C$_{39}$H$_{44}$BF$_2$IN$_2$S$_3$:

|  | C | H | N |
|---|---|---|---|
| Calculated | 57.64 | 5.46 | 3.45 |
| Found | 57.45 | 5.11 | 3.09 |

Example 9

Synthesis of Compound B16

Compound B16 was synthesized in accordance with the following synthesis scheme:

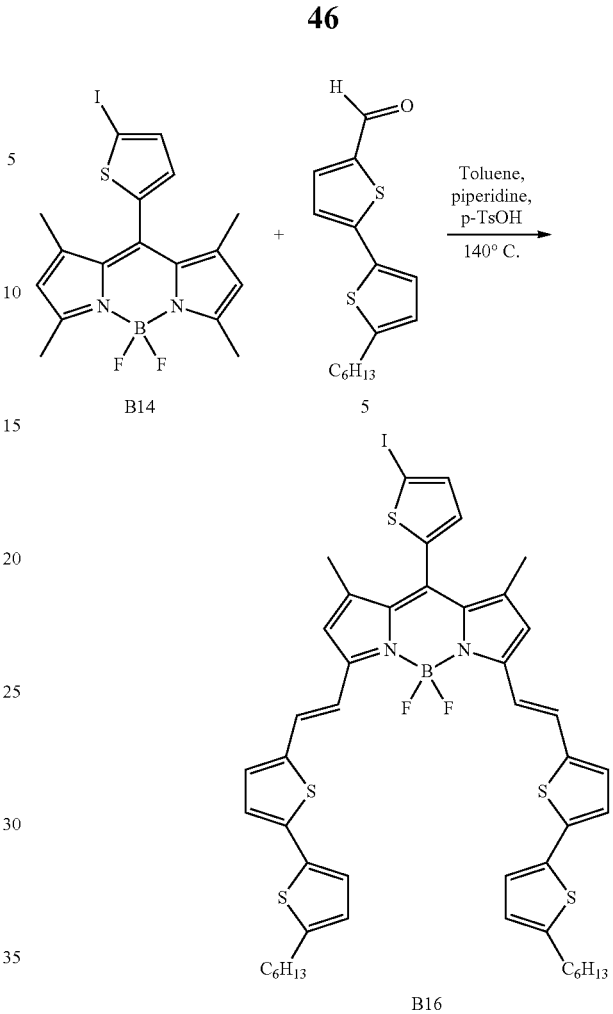

Compound B16 was synthesized by following general procedure n°1, starting from 198 mg (0.43 mmol, 1 eq) of compound B14 obtained above in the second step of example 8 and 302 mg (1.08 mmol, 2.5 eq) of compound 5 in a volume of 20 mL of toluene. A petroleum ether/CH$_2$Cl$_2$/toluene (7015/25; v/v/v) mixture was used to purify the desired compound. 135 mg of compound B16 (0.138 mmol, yield: 32%) was obtained.

$^1$H NMR (300 MHz, C$_6$D$_6$): 0.86-0.91 (m, 6H); 1.21-1.28 (m, 12H); 1.49-1.55 (m, 10H); 2.52-2.58 (m, 4H); 5.92-5.94 (m, 1H); 6.18 (s, 2H); 6.48-6.50 (m, 2H); 6.73-6.81 (m, 5H); 6.85-6.87 (m, 2H); 7.08 (s, 2H); 8.14 (s, 1H); 8.19 (s, 1H).

$^{13}$C NMR (50 MHz, C$_6$D$_6$): 14.1; 14.3; 23.0; 29.1; 30.5; 31.8; 31.9; 75.0; 118.7; 118.9; 124.2; 125.0; 125.5; 129.7; 130.0; 130.6; 135.1; 135.2; 137.5; 140.6; 141.1; 141.3; 142.2; 146.3; 153.0.

ESI-MS: 976.0 ([M], 100).

Elemental analysis for C$_{47}$H$_{48}$BF$_2$IN$_2$S$_5$:

|  | C | H | N |
|---|---|---|---|
| Calculated | 57.78 | 4.95 | 2.87 |
| Found | 57.41 | 4.70 | 2.52 |

Example 10

Synthesis of Compound B17

Compound B17 was synthesized in accordance with the following synthesis scheme:

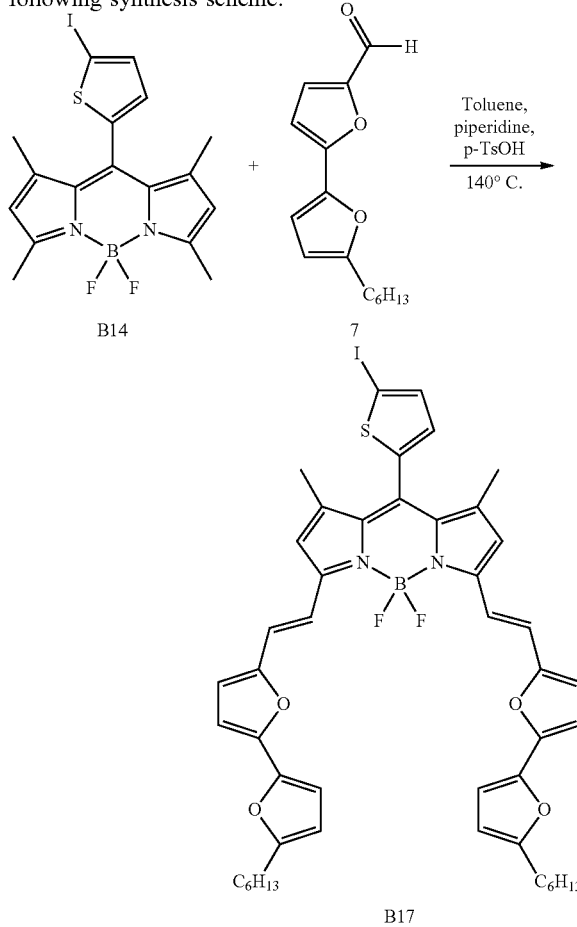

Compound B17 was synthesized by following general procedure n°1, starting from 201 mg (0.44 mmol, 1 eq) of compound B14 obtained above in the second step of example 8 and 240 mg (0.97 mmol, 2.2 eq) of compound 7 in a volume of 20 mL of toluene. A petroleum ether/$CH_2Cl_2$/toluene (70/5/25; v/v/v) mixture was used to purify the desired compound. 145 mg of compound B17 (0.159 mmol, yield: 36%) was obtained.

$^1$H NMR (300 MHz, $C_6D_6$): 0.87-0.93 (m, 6H); 1.28-1.45 (m, 12H); 1.66-1.79 (m, 10H); 2.66-2.73 (m, 4H); 6.10 (s, 2H); 6.59-6.62 (m, 4H); 6.67 (d, 2H, $^3J$=3.5 Hz); 6.70-6.73 (m, 3H); 7.03 (d, 2H, $^3J$=16.0 Hz); 7.28 (m, 1H); 7.59 (d, 2H, $^3J$=16.0 Hz).

$^{13}$C NMR (50 MHz, $C_6D_6$): 14.3; 22.8; 28.2; 28.4; 29.1; 31.8; 74.7; 107.4; 107.5; 108.3; 114.9; 117.0; 118.6; 123.0; 130.5; 137.5; 141.6; 144.7; 148.6; 152.3; 152.6; 157.6.

ESI-MS: 912.1 ([M], 100).

Elemental analysis for $C_{47}H_{48}BF_2IN_2O_4S$:

|  | C | H | N |
| --- | --- | --- | --- |
| Calculated | 61.85 | 5.31 | 3.07 |
| Found | 61.54 | 4.92 | 2.74 |

Example 11

Synthesis of Compound B19

Compound B19 was synthesized in accordance with the following synthesis scheme:

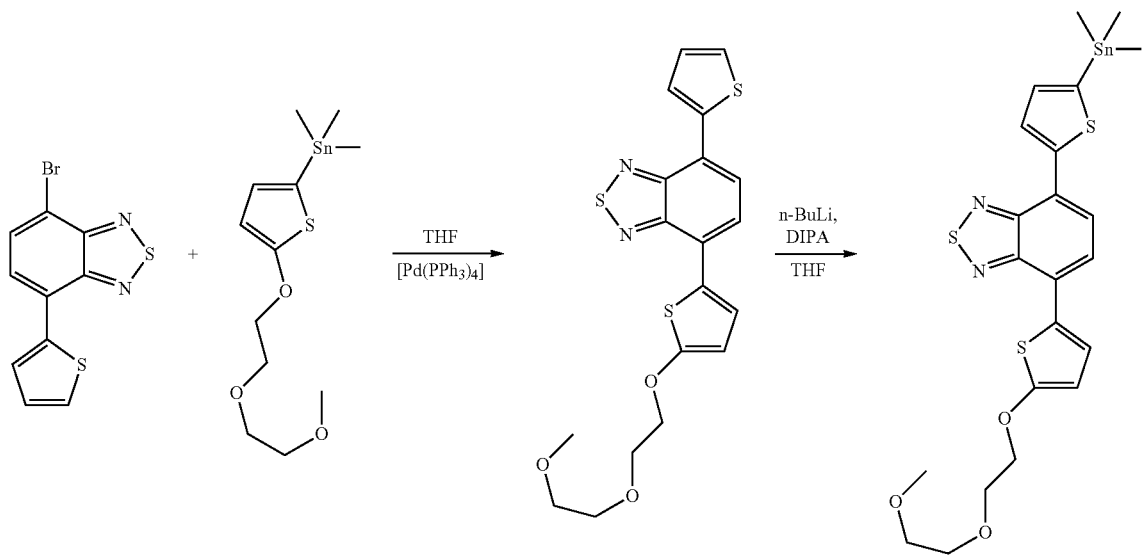

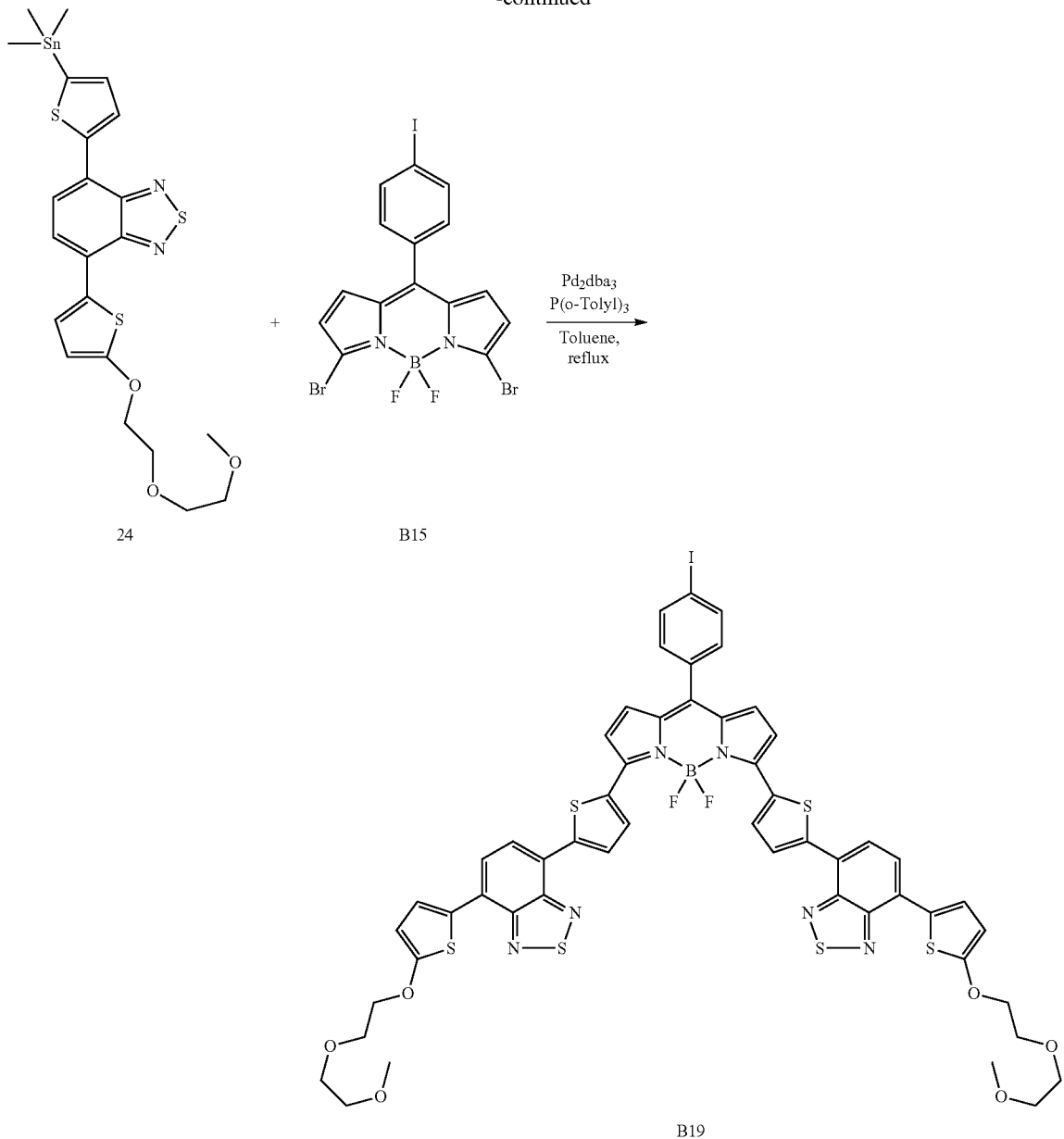

1) First Step: Synthesis of Compound 23:

3.3 g of 2-trimethylstannyl-5-PEG thiophene (compound 2, 12.8 mmol), 0.9 g of compound 22 (3.03 mmol) and 25 mL of THF were introduced into a 100 mL flask. The solution was degassed with the aid of argon for 20 minutes, then 0.35 g of [Pd(PPh$_3$)$_4$](0.3 mmol) was added and the solution was heated under reflux for 1 day. After cooling, the organic phase was extracted with ethyl acetate and the impure product was purified on a chromatographic column (eluent 80/20 (v/v), cyclohexane/AcOEt), then by recrystallization from acetone.

$^1$H NMR (Acetone d6, 300 MHz): 3.32 (s, 3H); 3.54 (t, $^3J$=5.2 Hz, 2H); 3.68 (t, $^3J$=5.2 Hz, 2H); 3.87 (t, $^3J$=4.6 Hz, 2H): 4.34 (t, $^3J$=4.6 Hz, 2H); 6.46 (d, $^3J$=4.2 Hz, 1H), 7.25 (dd, $^3J$=5.1 Hz, $^3J$=3.7 Hz, 1H); 7.63 (dd, $^3J$=5.1 Hz, $^4J$=1.0 Hz, 1H), 7.84 (d, $^3J$=7.7 Hz, 1H); 7.82 (d, $^3J$=4.2 Hz, 1H); 7.99 (d, $^3J$=7.7 Hz, 1H); 8.17 (dd, $^3J$=3.7 Hz, $^4J$=1.0 Hz, 1H).

$^{13}$C NMR (Acetone d6, 75 MHz): 59.6; 70.7; 72.0; 73.4; 74.7; 105.5; 125.3; 126.1; 126.9; 127.5; 127.7; 128.0; 128.5; 128.8; 129.4; 140.8; 153.8; 154.0; 168.9.

ESI-MS: 418.0 ([M], 100).

Elemental analysis for $C_{19}H_{18}N_2O_3S_3$:

|  | C | H | N |
|---|---|---|---|
| Calculated | 54.52 | 4.33 | 6.69 |
| Found | 54.33 | 4.47 | 6.42 |

2) Second Step: Synthesis of Compound 24:

2.5 M of nBuLi in 0.426 mL of hexane was added dropwise to 3 mL of a solution of 0.164 mL of diisopropylamine (1.17 mmol) in THF at −78° C. The solution was heated up to −40° C. for 30 min then cooled to −78° C. The compound 23 obtained as above in the preceding step (0.41 g, 0.97 mmol) was then added in solution in 5 mL of THF at −78° C. The solution was again heated up to 0° C. for 20 min, then trimethyltin chloride (1.0 M in THF, 1.17 mL) was added to the solution at −78° C. The solution was then stirred at ambient temperature for 12 hours. The organic phase was extracted with ethyl acetate and the impure product was used without purification. The conversion into the reactive stannic group was estimated to be 35% using NMR.

$^1$H NMR (CDCl$_3$, 300 MHz): 0.44 (s, 9H); 3.41 (s, 3H), 3.61 (t, $^3$J=4.92 Hz, 2H); 3.74 (t, $^3$J=4.52 Hz, 2H); 3.89 (t, $^3$J=4.86 Hz, 2H); 4.31 (t, $^3$J=4.56 Hz, 2H); 6.33 (d, $^3$J=4.24 Hz, 2H): 7.28 (d, $^3$J=3.45 Hz 1H); 7.63 (d, $^3$J=7.65 Hz, 1H); 7.81 (m, 2H): 8.14 (d, $^3$J=3.45 Hz, 1H).

3) Third Step: Synthesis of Compound B19:

160 mg of compound 24 obtained as above in the preceding step (0.275 mmol), 48 mg of compound B18 (0.11 mmol), 7 mg of tri(o-tolyl)phosphine, P(o-Tolyl)$_3$ (21 μmol) were added to a Schlenk tube containing distilled toluene, then the solution was degassed with the aid of argon for 45 min. 5 mg of [Pd$_2$(dba)$_3$](5.5 μmol) was then added, and the reaction medium was heated slowly to 110° C. for 3 hours. After cooling, the organic phase was extracted with dichloromethane and the impure product was purified on a chromatographic column (eluent 90/10 (v/v) CH$_2$Cl$_2$/AcOEt).

$^1$H NMR (200 MHz, CDCl$_3$): 2.47 (s, 3H); 3.41 (s, 6H); 3.59-3.62 (m, 4H); 3.72-3.75 (m, 4H); 3.87-3.90 (m, 4H); 4.28-4.31 (m, 4H); 6.31 (d, 2H, $^3$J=4.1 Hz); 6.80 (d, 2H, $^3$J=4.4 Hz); 6.92 (s, 2H); 7.30 (d, 2H, $^3$J=7.8 Hz); 7.41 (d, 2H, $^3$J=7.8 Hz): 7.56-7.61 (m, 2H); 7.80-7.83 (m, 4H); 8.10 (broad s, 2H): 8.37 (broad s, 2H).

ESI-MS: 1114.1 ([M], 100)

Elemental analysis for C$_{54}$H$_{45}$BF$_2$N$_6$O$_6$S$_6$:

|  | C | H | N |
|---|---|---|---|
| Calculated | 58.16 | 4.07 | 7.54 |
| Found | 57.94 | 3.82 | 7.38 |

Example 12

Synthesis of Compound B20

Compound B20 was synthesized in accordance with the following synthesis scheme:

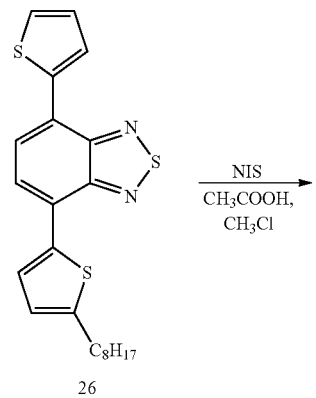

26

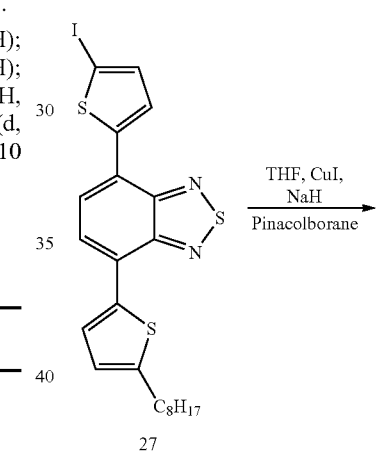

27

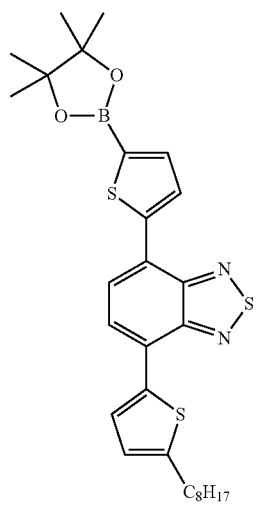

28

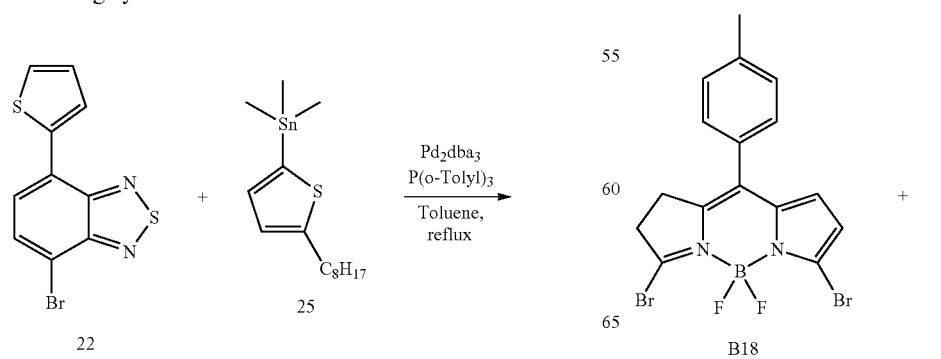

22    25    B18

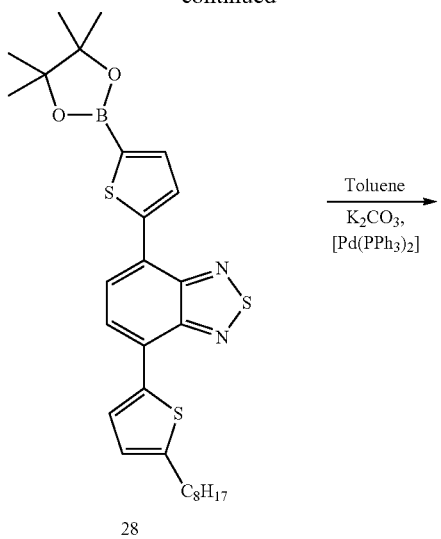

28

B20

1) First Step: Synthesis of Compound 26

0.54 g of 2-trimethylstannyl-5-octylthiophene (compound 25, 1.5 mmol), 0.37 g of compound 22 (1.23 mmol), 0.036 g of P(o-tolyl)$_3$ (0.12 mmol) and 8 mL of toluene were added to a 50 mL flask. The solution was degassed with the aid of argon for 20 minutes, then 0.027 g of [Pd$_2$(dba$_3$)] (0.03 mmol) was added and the solution was heated under reflux for 1 day. After cooling, the organic phase was extracted with ethyl acetate and the impure product was purified on a flash chromatographic column (eluent 80/20 (v/v), petroleum ether/toluene).

$^1$H NMR (CDCl$_3$, 300 MHz): 0.89 (t, $^3$J=5.2 Hz, 3H); 1.30 (m, 10H); 1.74 (t, $^3$J=7.6 Hz, 2H); 2.90 (t, $^3$J=7.6 Hz, 2H); 6.89 (d, $^3$J=3.7 Hz, 1H); 7.21 (dd, $^3$J=5.0 Hz, $^3$J=3.7 Hz, 1H); 7.45 (d, $^3$J=5.0 Hz, 1H); 7.80 (d, $^3$J=7.6 Hz, 1H); 7.86 (d, $^3$J=7.6 Hz, 1H); 7.95 (d, $^3$J=3.6 Hz, 1H); 8.10 (dd, $^3$J=3.6 Hz, $^4$J=0.6 Hz, 1H).

$^{13}$C NMR (CDCl$_3$, 75 MHz): 14.1; 22.7; 29.2; 29.2; 29.3; 30.3; 31.6; 31.8; 125.1; 125.2; 125.4; 125.9; 126.4; 126.6; 127.3; 127.6; 127.9; 136.7; 139.5; 148.1; 152.6; 152.7.

ESI-MS: 411.7 ([M], 100).

Elemental analysis for C$_{22}$H$_{24}$N$_2$S$_3$:

|  | C | H | N |
|---|---|---|---|
| Calculated | 64.04 | 5.86 | 6.79 |
| Found | 63.86 | 5.71 | 6.52 |

2) Second Step: Synthesis of Compound 27

The compound 26 (0.2 g, 0.48 mmol) obtained as above in the preceding step was dissolved in a chloroform/acetic acid mixture (15 mL/10 mL) in the dark. N-iodosuccinimide (NIS) (0.130 g, 1.2 eq) was added in portions to the solution which was then stirred for 2 hours at ambient temperature. The organic phase was then washed with water and the product was purified on a column (eluent 90/10 (v/v) cyclohexane/toluene).

$^1$H NMR (CDCl$_3$, 300 MHz): 0.89 (t, $^3$J=6.1 Hz, 3H); 1.31 (m, 10H); 1.76 (t, $^3$J=7.0 Hz, 2H); 2.89 (t, $^3$J=7.5 Hz, 2H); 6.88 (d, $^3$J=3.7 Hz, 1H); 7.34 (d, $^3$J=3.9 Hz, 1H); 7.68 (d, $^3$J=3.9 Hz, 1H); 7.77 (s, 2H); 7.95 (d, $^3$J=3.7 Hz, 1H).

$^{13}$C NMR (CDCl$_3$, 75 MHz): 14.1; 22.7; 29.1; 29.2; 29.3; 30.3; 31.6; 31.9; 124.2; 124.8; 125.3; 125.5; 126.8; 127.8; 128.0; 136.5; 137.66; 145.3; 148.3; 152.4.

ESI-MS: 537.7 ([M], 100).

Elemental analysis for C$_{22}$H$_{23}$IN$_2$S$_3$:

|  | C | H | N |
|---|---|---|---|
| Calculated | 49.07 | 4.30 | 5.20 |
| Found | 48.84 | 4.19 | 5.04 |

3) Third Step: Synthesis of Compound 28

Sodium hydride (0.685 mmol), copper iodide (0.046 mmol) and 4,4,5,5-tetramethyl-[1,3,2]dioxaborolane (pinacolborane) (0.133 mL) was added to a solution of 0.457 mmol of compound 27 obtained as above in the preceding step in 15 mL of freshly distilled tetrahydrofuran. Stirring at ambient temperature was maintained for 1 hour. The desired compound 28 was obtained in the form of an orange oil after purification by silica gel chromatography using a mixture of solvents (petroleum ether/dichloromethane 8/2 (v/v) then 0/10 (v/v) then dichloromethane/ethyl acetate 8/2 (v/v)). (Synthesis yield: 61%).

$^1$H NMR (200 MHz, CDCl$_3$): 0.88 (t, 3H, $^3$J=6.6 Hz); 1.32 (m, 10H); 1.38 (s, 12H): 1.75 (m, 2H); 2.88 (t, 2H, $^3$J=7.5 Hz); 6.88 (d, 1H, $^3$J=3.8 Hz); 7.71 (d, 1H, $^3$J=3.8 Hz); 7.85 (ABsyst, 2H, $^3$J=7.7 Hz); 7.95 (d, 1H, $^3$J=3.8 Hz); 8.17 (d, 1H, $^3$J=3.8 Hz).

$^{13}$C NMR (50 MHz, (CDCl$_3$): 14.2; 22.7; 24.9; 29.2; 29.3; 29.4; 30.4; 31.7; 32.0; 84.3; 125.1; 125.3; 125.4; 126.6; 127.0; 127.9; 128.5; 136.8; 138.0; 146.2; 148.4.

ESI-MS: 537.8 (100)

Elemental analysis for C$_{28}$H$_{35}$BN$_2$O$_2$S$_3$:

|  | C | H | N |
|---|---|---|---|
| Calculated | 62.44 | 6.55 | 5.20 |
| Found | 62.65 | 6.84 | 5.31 |

4) Fourth Step: Synthesis of Compound B20

Compound B20 was synthesized by following general procedure n°3, starting from 285 mg (0.54 mmol) of compound 28 obtained as above in the preceding step, 98 mg (0.22 mmol) of compound B18, 123 mg (0.89 mmol) of K$_2$CO$_3$ and 25 mg (22 µmol) of [Pd(PPh$_3$)$_4$]. A CH$_2$Cl$_2$/ petroleum ether (40/60, v/v) mixture was used to purify the desired compound. 130 mg of compound B20 (yield: 53%) was obtained.

$^1$H NMR (300 MHz, CDCl$_3$): 0.88-0.90 (m, 6H); 1.30-1.39 (m, 20H); 1.70-1.77 (m, 4H); 2.47 (s, 3H); 2.87 (broad s, 4H); 6.80 (d, 2H, $^3$J=4.3 Hz); 6.85 (d, 2H, $^3$J=3.4 Hz); 6.90-6.92 (m, 2H); 7.30 (d, 2H, $^3$J=7.8 Hz); 7.41 (d, 2H, $^3$J=7.8 Hz); 7.71 (d, 2H, $^3$J=7.5 Hz), 7.84-7.91 (m, 4H); 8.12-8.13 (m, 2H); 8.39 (broad s, 2H).

Elemental analysis for C$_{60}$H$_{57}$BF$_2$N$_6$S$_6$:

|  | C | H | N |
|---|---|---|---|
| Calculated | 64.23 | 4.72 | 8.03 |
| Found | 64.02 | 4.52 | 7.69 |

Example 13

Synthesis of Compound B21

Compound B21 was synthesized in accordance with the following synthesis scheme:

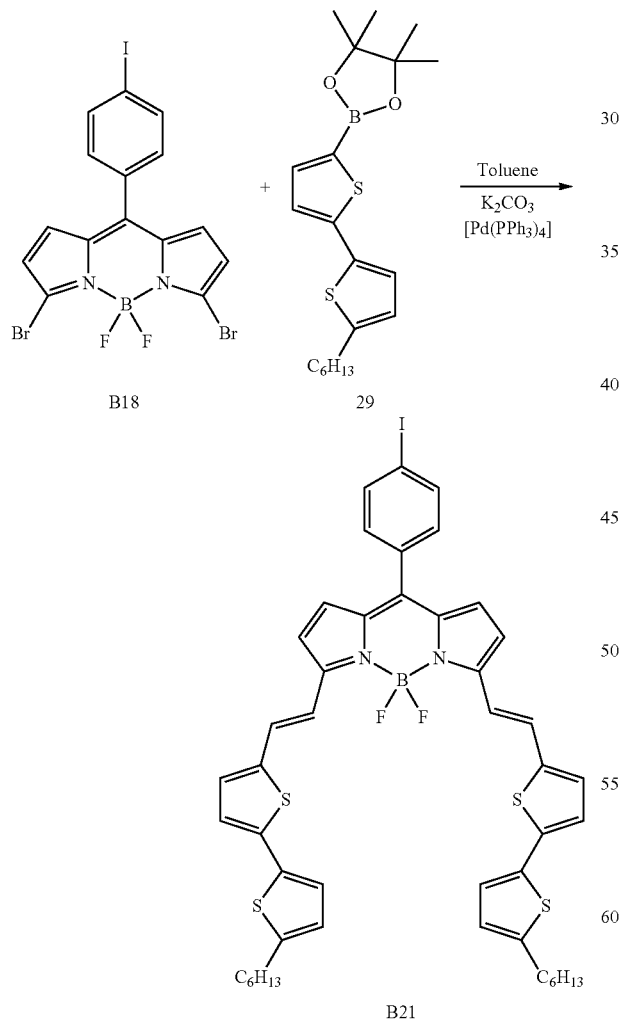

Compound B21 was synthesized by following general procedure n°3, starting from 257 mg (0.683 mmol) of compound 29, 100 mg (0.228 mmol) of compound B18, 157 mg (1.14 mmol) of K$_2$CO$_3$ and 25 mg (22 µmol) of [Pd(PPh$_3$)$_4$]. A petroleum ether/toluene (70/30, v/v) mixture was used to purify the desired compound. 130 mg of compound B21 (yield 53%) was obtained.

$^1$H NMR (300 MHz, C$_6$D$_6$), δ (ppm): 0.88 (t, 6H, $^3$J=7.0 Hz); 1.25-1.18 (m, 12H); 1.55-1.46 (m, 4H); 2.11 (s, 3H); 2.53 (t, 4H, $^3$J=7.5 Hz); 6.47 (d, 2H, $^3$J=3.6 Hz); 6.55 (d, 2H, $^3$J=4.2 Hz); 6.63 (d, 2H, $^3$J=4.2 Hz); 6.96 (d, 2H, $^3$J=3.6 Hz); 7.03 (d, 2H, $^3$J=4.2 Hz): 7.95 (AB sys, 4H, J$_{AB}$=8.0 Hz, ν$_o$δ=41.7 Hz); 8.63 (d, 2H, $^3$J=4.2 Hz).

$^{13}$C NMR (50 MHz, (CDCl$_3$): 14.1; 21.0; 22.7; 28.8; 30.2; 31.5; 31.6; 120.5; 124.6; 125.3; 125.4; 127.6; 127.7; 127.8; 128.8; 129.5; 130.6; 132.0; 132.9; 134.7; 137.4; 139.5; 139.7; 141.7; 146.5; 149.6.

ESI-MS: 778.3 (100).

Elemental analysis for C$_{44}$H$_{45}$BF$_2$N$_2$S$_4$:

|  | C | H | N |
|---|---|---|---|
| Calculated | 67.85 | 5.82 | 3.60 |
| Found | 67.64 | 5.59 | 3.44 |

Example 14

Synthesis of Compound B22

Compound B22 was synthesized in accordance with the following synthesis scheme:

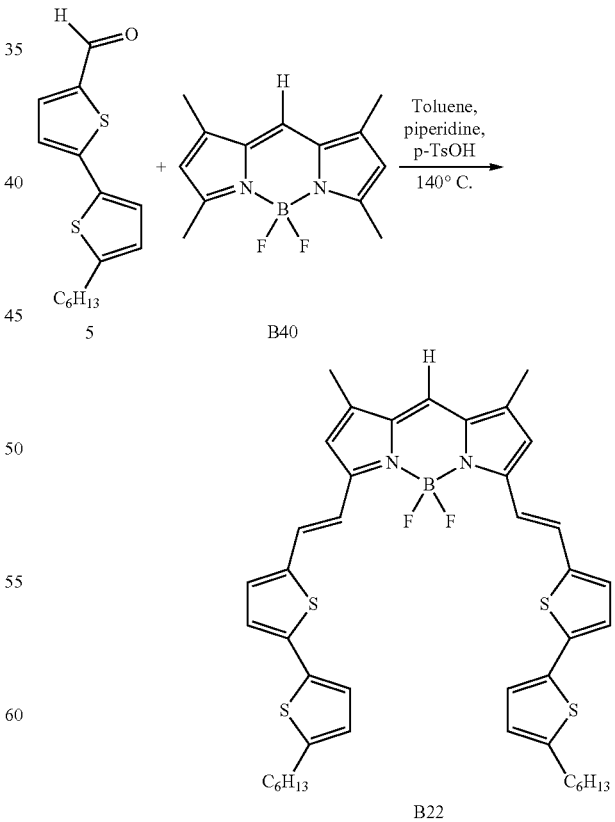

Compound B22 was synthesized by following general procedure n°1, starting from 40 mg (0.16 mmol, 1 eq) of compound B40, 100 mg (0.35 mmol, 2.2 eq) of compound 5 in a volume of 10 mL of toluene. A petroleum ether/$CH_2Cl_2$/toluene (50/10/40, v/v/v) mixture was used to purify the desired compound. 90 mg of compound B22 (0.117 mmol, yield 73%) was obtained.

$^1$H NMR (300 MHz, $CDCl_3$): 0.88 (t, 6H, $^3$J=6.7 Hz); 1.27-1.40 (m, 12H); 1.63-1.73 (m, 4H); 2.29 (s, 6H); 2.80 (t, 4H, $^3$J=7.5 Hz); 6.68 (s, 2H); 6.72 (d, 2H, $^3$J=3.3 Hz); 6.99 (s, 1H); 7.05 (d, 2H, $^3$J=3.6 Hz); 7.12 (d, 4H, $^3$J=3.3 Hz); 7.25 (d, 2H, $^3$J=15.8 Hz); 7.35 (d, 2H, $^3$J=15.8 Hz).

$^{13}$C NMR (50 MHz, $CDCl_3$): 11.4; 14.1; 28.8; 30.3; 31.6; 115.6; 115.9; 118.1; 123.7; 124.2; 125.1; 128.7; 129.6; 134.7; 139.5; 140.6; 146.4.

ESI-MS: 768.1 ([M], 100):

Elemental analysis for $C_{43}H_{47}BF_2N_2S_4$:

|  | C | H | N |
|---|---|---|---|
| Calculated | 67.17 | 6.16 | 3.64 |
| Found | 66.89 | 5.83 | 3.40 |

Example 15

Synthesis of Compound B24

Compound B24 was synthesized in accordance with the following synthesis scheme:

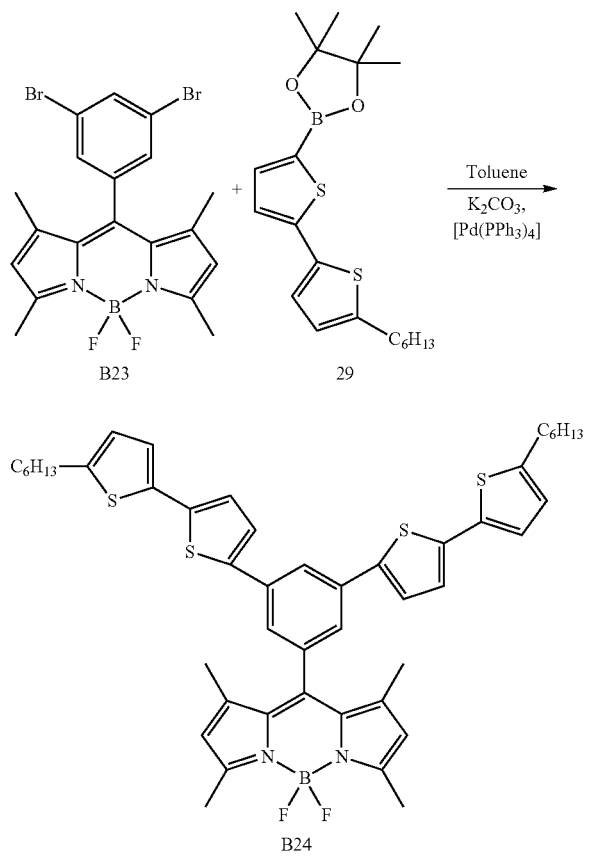

Compound B24 was synthesized by following general procedure n°3, starting from 200 mg (0.415 mmol, 1 eq) of compound B23, 350 mg (0.91 mmol, 2.2 eq) of compound 29, 0.83 mL of a 2M solution of $K_2CO_3$ and 5 mg of [$Pd(PPh_3)_4$](10% molar) in a volume of 10 mL of toluene. A petroleum ether/$CH_2Cl_2$ (80/20, v/v) mixture was used to purify the desired compound. 222 mg of compound B24 (0.270 mmol, yield: 65%) was obtained.

$^1$H NMR (200 MHz, $CDCl_3$): 0.92 (t, 6H, $^3$J=6.3 Hz); 1.35-1.48 (m, 12H); 1.58-1.74 (m, 10H); 2.61 (s, 6H); 2.81 (t, 4H, $^3$J=7.3 Hz); 6.03 (s, 2H); 6.70 (d, 2H, $^3$J=3.4 Hz); 7.02-7.09 (m, 4H); 7.29 (d, 2H, $^3$J=3.9 Hz); 7.41 (s, 2H): 7.88 (s, 1H).

$^{13}$C NMR (50 MHz, $CDCl_3$): 14.2; 14.7; 15.1; 22.7; 28.8; 30.2; 31.6; 121.5; 122.4; 123.5; 123.8; 124.0; 124.7; 125.0; 131.3; 134.4; 135.9; 136.4; 138.5; 140.4; 140.5; 143.1; 146.1; 155.9.

ESI-MS: 820.2 ([M], 100)

Elemental analysis for $C_{47}H_{51}BF_2N_2S_4$:

|  | C | H | N |
|---|---|---|---|
| Calculated | 68.76 | 6.26 | 3.41 |
| Found | 68.54 | 6.04 | 3.27 |

Example 16

Synthesis of Compound B25

Compound B25 was synthesized in accordance with the following synthesis scheme:

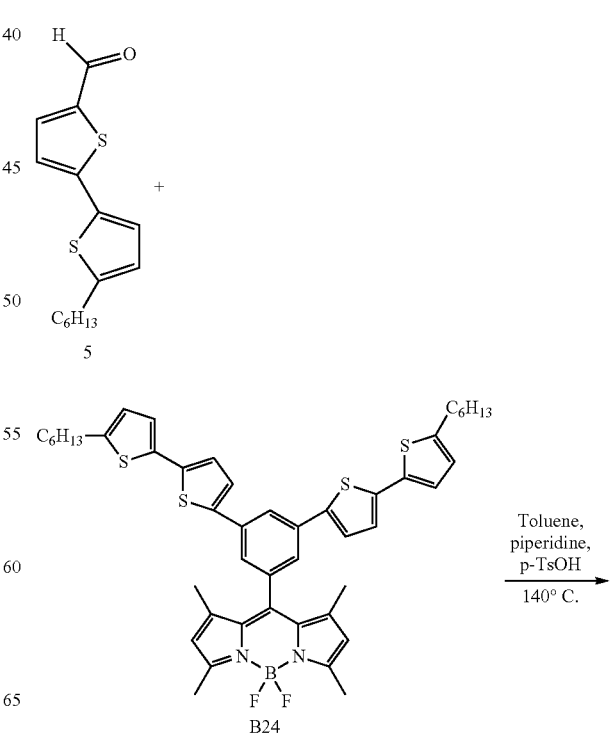

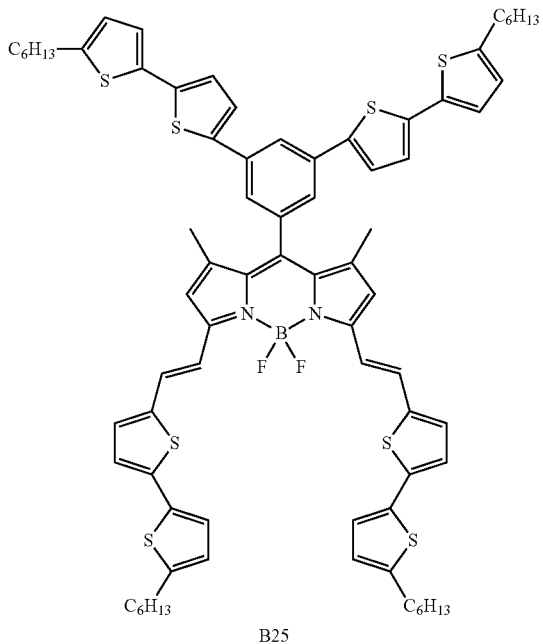

B25

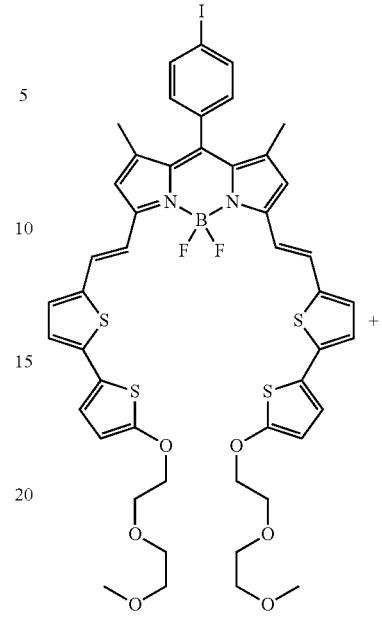

B2

Compound B25 was synthesized by following general procedure n°1, starting from 210 mg (0.25 mmol, 1 eq) of compound B24 obtained above in example 15, 160 mg (0.56 mmol, 2.2 eq) of compound 5 in a volume of 20 mL of toluene. A petroleum ether/toluene (70/30, v/v) mixture was used to purify the desired compound. 232 mg of compound B25 (0.173 mmol, yield: 68%) was obtained.

$^1$H NMR (200 MHz, CDCl$_3$): 0.87-0.93 (m, 12H): 1.25-1.35 (m, 24H); 1.55-1.69 (m, 14H); 2.80 (m, 8H); 6.62 (s, 2H); 6.69-6.73 (m, 4H); 7.02-7.14 (m, 10H): 7.27-7.35 (superimposed with the solvent m, 4H); 7.45-7.52 (m, 4H); 7.86-7.88 (m, 1H).

$^{13}$C NMR (CDCl$_3$, 50 MHz): 14.2; 15.4; 22.7; 28.9; 30.4; 31.7; 118.1; 118.3; 122.5; 123.9; 124.1; 124.3; 124.8; 125.3; 129.0; 129.8; 133.7; 134.9; 135.9; 136.2; 136.8; 138.6; 140.1; 140.7; 140.8; 141.7; 146.2; 146.6; 152.3.

ESI-MS: 1340.3 ([M], 100)

Elemental analysis for $C_{77}H_{83}BF_2N_2S_8$:

|  | C | H | N |
|---|---|---|---|
| Calculated | 68.92 | 6.23 | 2.09 |
| Found | 69.27 | 6.54 | 2.38 |

Example 17

Synthesis of Compound B26

Compound B26 was synthesized in accordance with the following synthesis scheme:

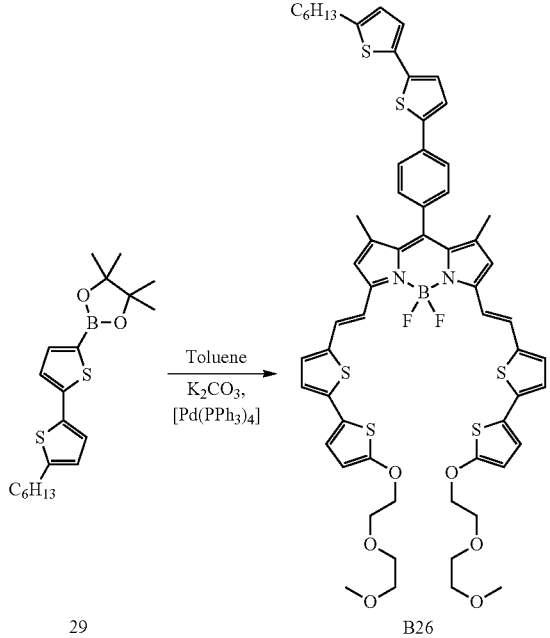

Compound B26 was synthesized by following general procedure n°3, starting from 102 mg (98.2 µmol, 1 eq) of compound B2 obtained above in example 1, 45 mg (0.118 mmol, 1.2 eq) of compound 29, 242 µL of a 2M solution of K$_2$CO$_3$ and 5 mg of [Pd(PPh$_3$)$_4$](10% molar) in a volume of 5 mL of toluene. A petroleum ether/ethyl acetate (70/30, v/v) mixture was used to purify the desired compound. 68 mg of compound B26 (58.9 µmol, yield 60%) was obtained.

$^1$H NMR (200 MHz, CDCl$_3$): 0.85-0.91 (m, 3H); 1.34-1.51 (m, 10H); 1.66-1.69 (m, 2H); 2.80 (t, 2H, $^3$J=7.5 Hz); 3.40 (s, 6H): 3.56-3.60 (m, 4H): 3.69-3.73 m, 4H); 3.83-3.87 (m, 4H); 4.21-4.25 (m, 4H); 6.19 (d, 2H, $^3$J=3.7 Hz); 6.58 (s, 2H); 6.70 (d, 1H, J=3.7 Hz); 6.90-6.94 (m, 5H); 7.02-7.09 (m, 4H); 7.24-7.48 (m, 8H); 7.70 (d, 2H, $^3$J=8.1 Hz).

$^{13}$C NMR (50 MHz, CDCl$_3$): 14.2; 15.1; 22.7; 28.9; 30.3; 31.7; 59.2; 69.4; 70.9; 72.1; 73.2; 106.4; 117.9; 118.1; 122.4;

123.1; 123.7; 124.1; 124.2; 124.4; 125.1; 125.8; 128.7; 129.4; 129.7; 133.7; 133.9; 134.2; 134.6; 136.8; 138.1; 140.1; 141.3; 141.6; 145.9; 152.1; 165.1.

ESI-MS: 1160.2 ([M], 100).

Elemental analysis for $C_{61}H_{63}BF_2N_2O_6S_6$:

|  | C | H | N |
|---|---|---|---|
| Calculated | 63.09 | 5.47 | 2.41 |
| Found | 63.22 | 5.54 | 2.74 |

Example 18

Synthesis of Compound B27

Compound B27 was synthesized in accordance with the following synthesis scheme:

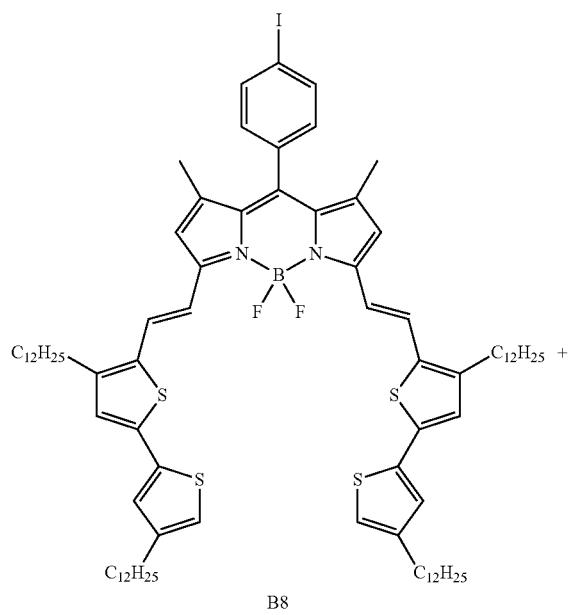

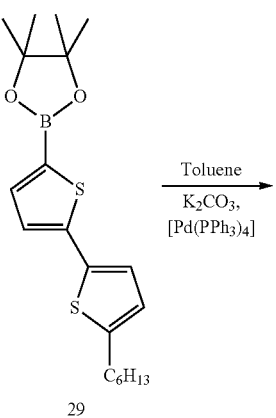

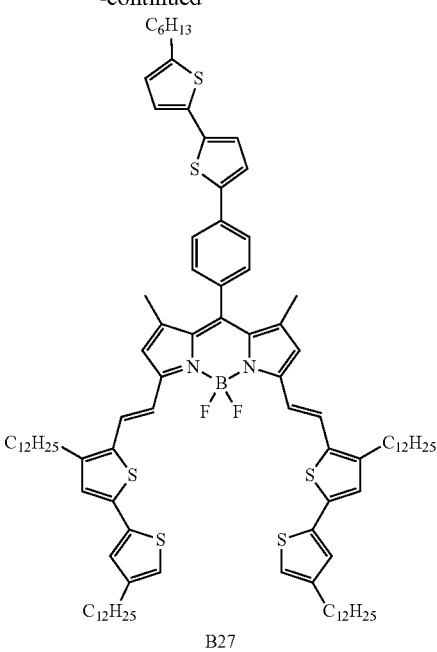

Compound B27 was synthesized by following general procedure n°3, starting from 55 mg (37.5 µmol, 1 eq) of compound B8 obtained above in example 5, 17 mg (45.1 µmol, 1.2 eq) of compound 29, 90 µL of a 2M solution of $K_2CO_3$ and 5 mg of $[Pd(PPh_3)_4]$ (10% molar) in a volume of 5 mL of toluene. A petroleum ether/$CH_2Cl_2$/toluene (75/5/20, v/v/v) mixture was used to purify the desired compound. 35 mg of compound B27 (21.9 µmol, yield 58%) was obtained.

$^1$H NMR (300 MHz, $CDCl_3$): 0.85-0.94 (m, 15H); 1.26-1.35 (m, 84H); 1.63-1.70 (m, 12H); 2.58-2.69 (m, 6H); 2.82 (t, 2H, $^3J$=7.5 Hz); 6.61 (s, 2H); 6.72 (d, 1H, $^3J$=3.4 Hz); 6.83 (s, 2H); 6.97 (s, 2H); 7.05 (d, 1H, $^3J$=3.4 Hz); 7.11-7.15 (m, 3H); 7.32-7.35 (superimposed with the solvent m, 4H); 7.41 (br, 3H); 7.74 (d, 2H, $^3J$=8.2 Hz).

$^{13}$C NMR (50 MHz, $CDCl_3$): 14.2; 15.1; 22.7; 22.8; 28.8; 29.5; 29.6; 29.7; 29.8; 30.3; 30.5; 30.7; 31.1; 31.8; 32.1; 117.6; 118.1; 119.8; 123.7; 124.1; 124.4; 125.1; 125.8; 125.9; 126.2; 127.1; 129.5; 134.5; 134.6; 134.8; 135.5; 137.1; 138.1; 141.3; 141.4; 144.4; 145.2; 146.1; 152.4.

ESI-MS: 1596.8 ([M], 100)

Elemental analysis for $C_{99}H_{139}BF_2N_2S_6$:

|  | C | H | N |
|---|---|---|---|
| Calculated | 74.39 | 8.77 | 1.75 |
| Found | 74.64 | 9.05 | 1.96 |

Example 19

Synthesis of Compound B28

Compound B28 was synthesized in accordance with the following synthesis scheme:

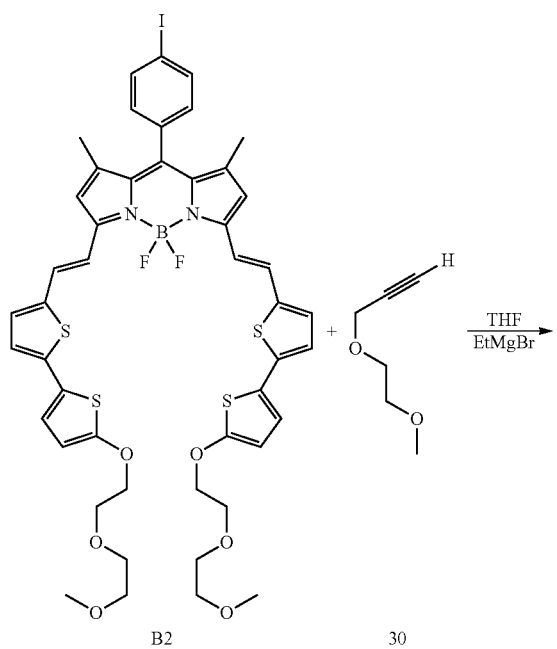

6.59 (s, 2H); 6.93-6.95 (m, 4H); 7.06-7.10 (m, 4H); 7.20 (d, 2H, $^3J=15.9$ Hz); 7.83 (d, 2H, $^3J=8.5$ Hz); 7.95 (d, 2H, $^3J=15.9$ Hz).

$^{13}C$ NMR (50 MHz, CDCl$_3$): 15.2; 58.8; 59.2; 59.4; 68.3; 69.4; 70.9; 71.8; 72.0; 73.2; 91.9; 94.6; 106.4; 118.5; 119.8; 122.4; 123.2; 124.1; 127.1; 129.2; 130.8; 131.9; 135.3; 136.1; 138.2; 139.7; 139.9; 140.8; 151.4; 165.0.

ESI-MS: 1226.1 ([M], 100)

Elemental analysis for $C_{59}H_{64}BIN_2O_{10}S_4$:

|  | C | H | N |
| --- | --- | --- | --- |
| Calculated | 57.75 | 5.26 | 2.28 |
| Found | 57.54 | 4.92 | 1.98 |

Example 20

Synthesis of Compound B29

Compound B29 was synthesized in accordance with the following synthesis scheme:

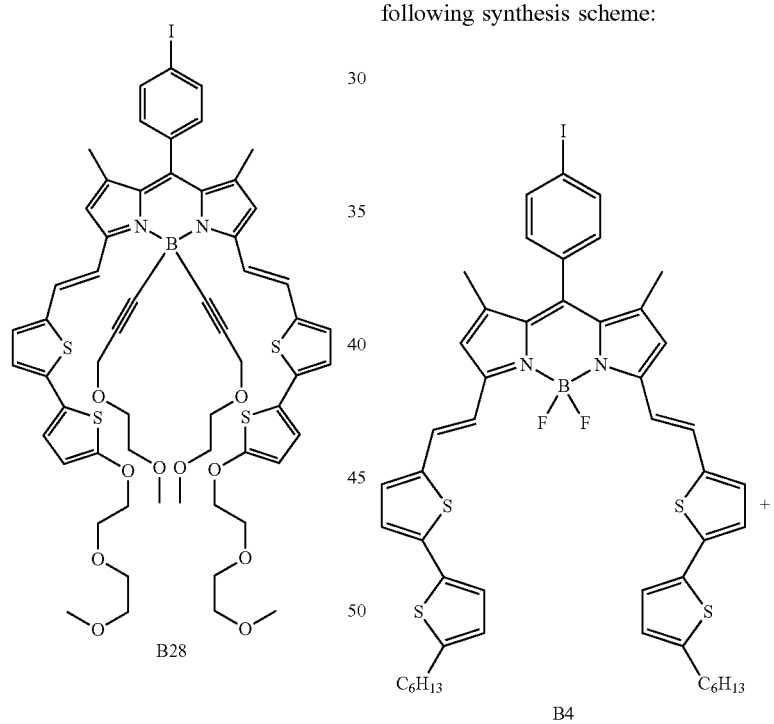

Compound B28 was synthesized by following general procedure n°2, starting from 230 mg (0.221 mmol, 1 eq) of compound B2 as prepared above in example 1, 88 mg (90 μL, 0.774 mmol, 3.5 eq) of compound 30 and 0.664 mL of a solution of ethylmagnesium bromide (0.664 mmol, 3 eq) in a volume of 10 mL of THF. A petroleum ether/ethyl acetate (60/40, v/v) mixture was used to purify the desired compound. 244 mg of compound B28 (0.2 mmol, Yield: 90%) was obtained.

$^1H$ NMR (200 MHz, CDCl$_3$): 1.43 (s, 6H); 3.21 (s, 6H); 3.32-3.36 (m, 4H); 3.40 (s, 6H); 3.57-3.74 (m, 12H); 3.84-3.89 (m, 4H); 4.23-4.27 (m, 8H); 6.21 (d, 2H, $^3J=3.6$ Hz);

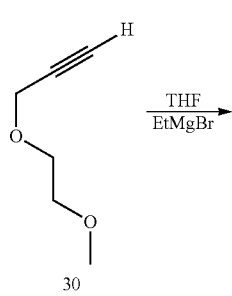

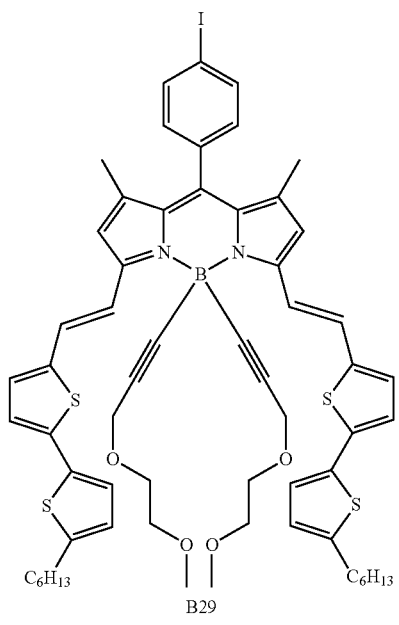

Compound B29 was synthesized by following general procedure n°2, starting from 120 mg (0.123 mmol, 1 eq) of compound B4 as prepared above in example 2, 56 mg (60 µL, 0.49 mmol, 4 eq) of compound 30 and 0.430 mL of a solution of ethylmagnesium bromide (EtMgBr) (0.430 mmol, 3.5 eq) in a volume of 10 mL of THF. A $CH_2Cl_2$/petroleum ether (70/30, v/v) mixture was used to purify the desired compound. 134 mg of compound B29 (0.115 mmol, Yield 94%) was obtained.

$^1$H NMR (300 MHz, $CDCl_3$): 0.91 (t, 6H, 6.9 Hz); 1.27-1.45 (m, 18H); 1.66-1.76 (m, 4H); 2.82 (t, 4H, 7.5 Hz); 3.22 (s, 6H); 3.34-3.37 (m, 4H); 3.68-3.71 (m, 4H); 4.25 (s, 4H); 6.60 (s, 2H); 6.73 (d, 2H, $^3J$=3.5 Hz); 7.05-7.26 (m, 10H); 7.84 (d, 2H, $^3J$=8.2 Hz); 7.99 (d, 2H, 15.9 Hz).

$^{13}$C NMR (50 MHz, $CDCl_3$): 14.2; 15.2; 22.7; 28.9; 30.4; 31.7; 58.9; 59.5; 68.3; 71.8; 94.7; 118.6; 120.0; 124.1; 124.4; 125.2; 127.1; 129.2; 130.8; 131.9; 134.7; 135.3; 138.2; 139.5; 140.0; 141.3; 146.5; 151.5.

ESI-MS: 1158.2 ([M], 100)

Elemental analysis for $C_{61}H_{68}BIN_2O_4S_4$:

|  | C | H | N |
|---|---|---|---|
| Calculated | 63.20 | 5.91 | 2.42 |
| Found | 63.04 | 5.77 | 2.09 |

Example 21

Synthesis of Compound B30

Compound B30 was synthesized in accordance with the following synthesis scheme:

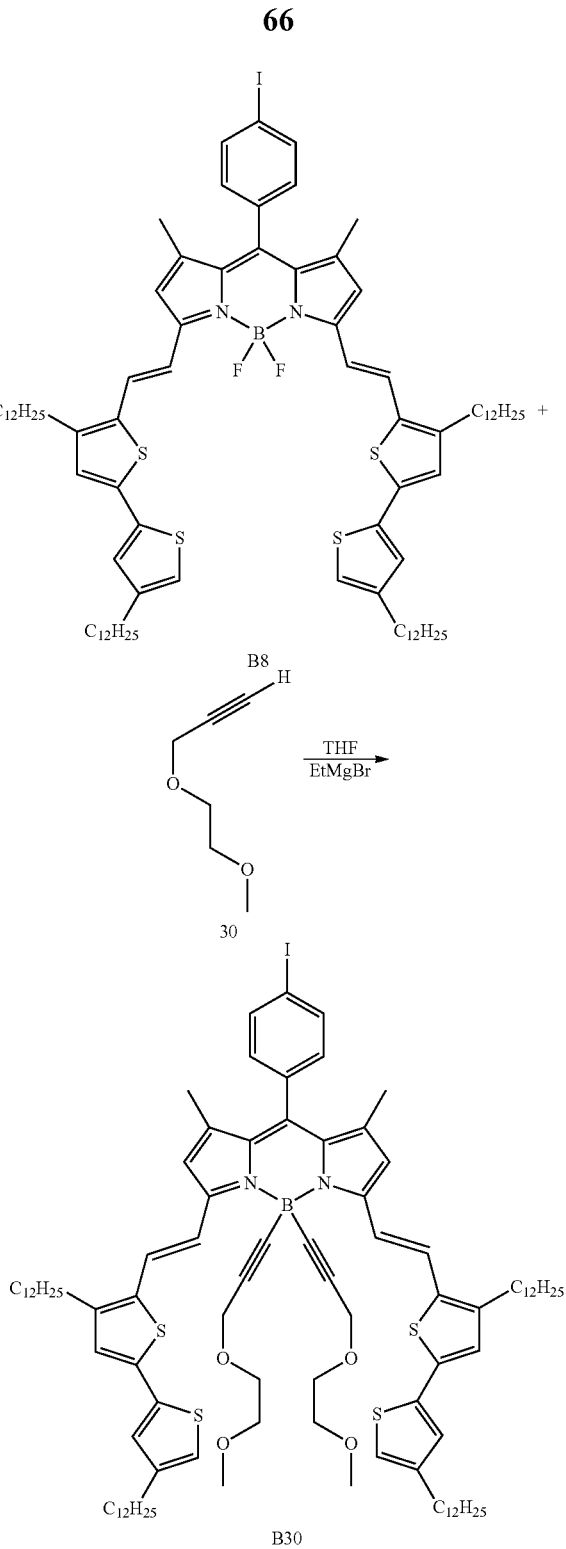

Compound B30 was synthesized by following general procedure n°2, starting from 190 mg (0.129 mmol, 1 eq) of compound B8 as prepared above in example 5, 52 mg (54 µL, 0.45 mmol, 3.5 eq) of compound 30 and 0.387 mL of a solution of ethylmagnesium bromide (0.387 mmol, 3 eq) in a volume of 10 mL of THF. A petroleum ether/ethyl acetate (90/10, v/v) mixture was used to purify the desired compound. 200 mg of compound B30 (0.120 mmol, Yield: 93%) was obtained.

¹H NMR (300 MHz, CDCl₁): 0.89 (m, 12H): 1.27-1.34 (m, 72H): 1.48 (s, 6H); 1.66 (br, 8H); 2.59-2.71 (m, 8H); 3.20 (s, 6H); 3.35-3.38 (m, 4H); 3.70-3.74 (m, 4H); 4.27 (s, 4H); 6.64 (s, 2H); 6.84 (s, 2H); 6.98 (s, 2H); 7.11-7.14 (m, 4H); 7.32 (d, 2H, ³J=15.8 Hz); 7.86 (d, 2H, ³J=8.20 Hz); 7.93 (d, 2H, ³J=15.8 Hz).

¹³C NMR (50 MHz, CDCl₃): 14.1; 15.1; 22.7; 28.7, 29.3; 29.5, 29.6; 29.7; 30.4; 30.5; 31; 31.9; 58.7; 59.4; 68.2; 71.7; 91.8; 94.5; 118.4; 119.1; 119.6; 125.2; 125.8; 126.3; 130.8; 135.3; 135.8; 136.9; 137.7; 138.1; 139.6; 144.4; 144.7; 151.7.

ESI-MS: 1662.1 ([M], 100).

Elemental analysis for C₉₇H₁₄₀BIN₂O₄S₄:

|  | C | H | N |
|---|---|---|---|
| Calculated | 70.01 | 8.48 | 1.68 |
| Found | 69.72 | 8.34 | 1.45 |

Example 22

Synthesis of Compound B31

Compound B31 was synthesized in accordance with the following synthesis scheme:

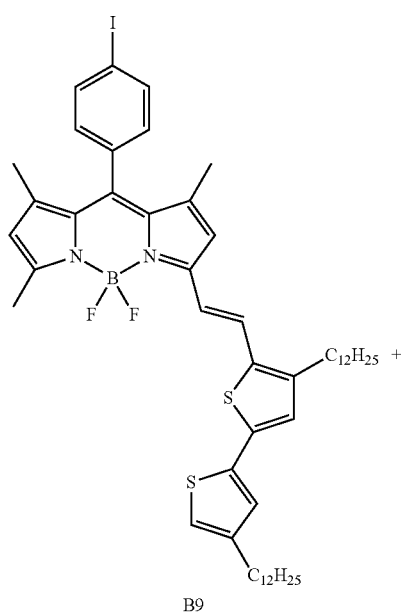

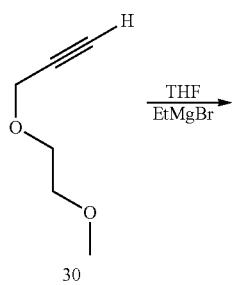

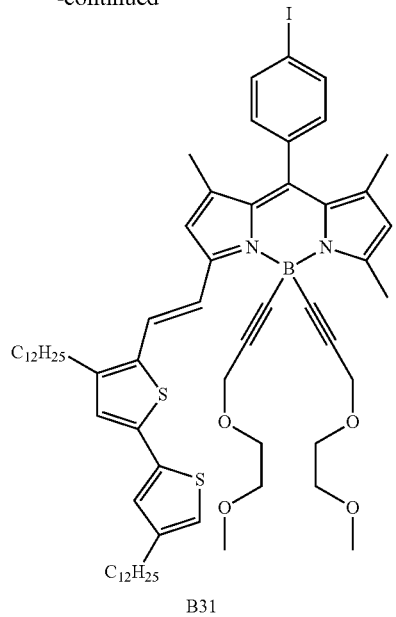

Compound B31 was synthesized by following general procedure n°2, starting from 130 mg (0.135 mmol, 1 eq) of compound B9 as prepared above in example 5, 54 mg (57 µL, 0.47 mmol, 3.5 eq) of compound 30 and 0.4 mL of a solution of ethylmagnesium bromide (0.4 mmol, 3 eq) in a volume of 10 mL of THF. A petroleum ether/ethyl acetate (90/10, v/v) mixture was used to purify the desired compound. 140 mg of compound B31 (0.121 mmol, Yield 90%) was obtained.

¹H NMR (300 MHz, CDCl₃): 0.86-0.90 (m, 6H); 1.27-1.34 (m, 36H); 1.43 (s, 3H); 1.46 (s, 3H); 1.61-1.67 (m, 4H); 2.57-2.77 (m, 4H); 2.77 (s, 3H); 3.26 (s, 6H); 3.39-3.43 (m, 4H); 3.60-3.71 (m, 4H); 4.24 (s, 4H); 6.05 (s, 1H); 6.60 (s, 1H); 6.83 (s, 1H); 6.95 (s, 1H); 7.07-7.12 (m, 3H); 7.25 (d, 1H, ³J=15.8 Hz); 7.85 (d, 2H, ³J=8.20 Hz); 7.92 (d, 1H, ³J=15.8 Hz).

¹³C NMR (50 MHz, CDCl₃): 14.2; 15.0; 15.2; 16.4; 22.8; 28.7; 29.4; 29.5; 29.6; 29.7; 29.8; 30.5; 30.6; 31.1; 32.1; 58.9; 59.6; 68.5; 71.8; 91.5; 94.6; 118.1; 119.3; 119.8; 121.9; 124.9; 125.7; 126.2; 130.2; 130.6; 130.9; 135.3; 135.8; 136.9; 137.6; 138.2; 138.3; 140.2; 140.7; 144.5; 151.7; 155.7.

ESI-MS: 1150.2 ([M], 100).

Elemental analysis for C₆₄H₈₈BIN₂O₄S₂:

|  | C | H | N |
|---|---|---|---|
| Calculated | 66.77 | 7.70 | 2.43 |
| Found | 66.42 | 7.38 | 2.09 |

Example 23

Synthesis of Compound B32

Compound B32 was synthesized in accordance with the following synthesis scheme:

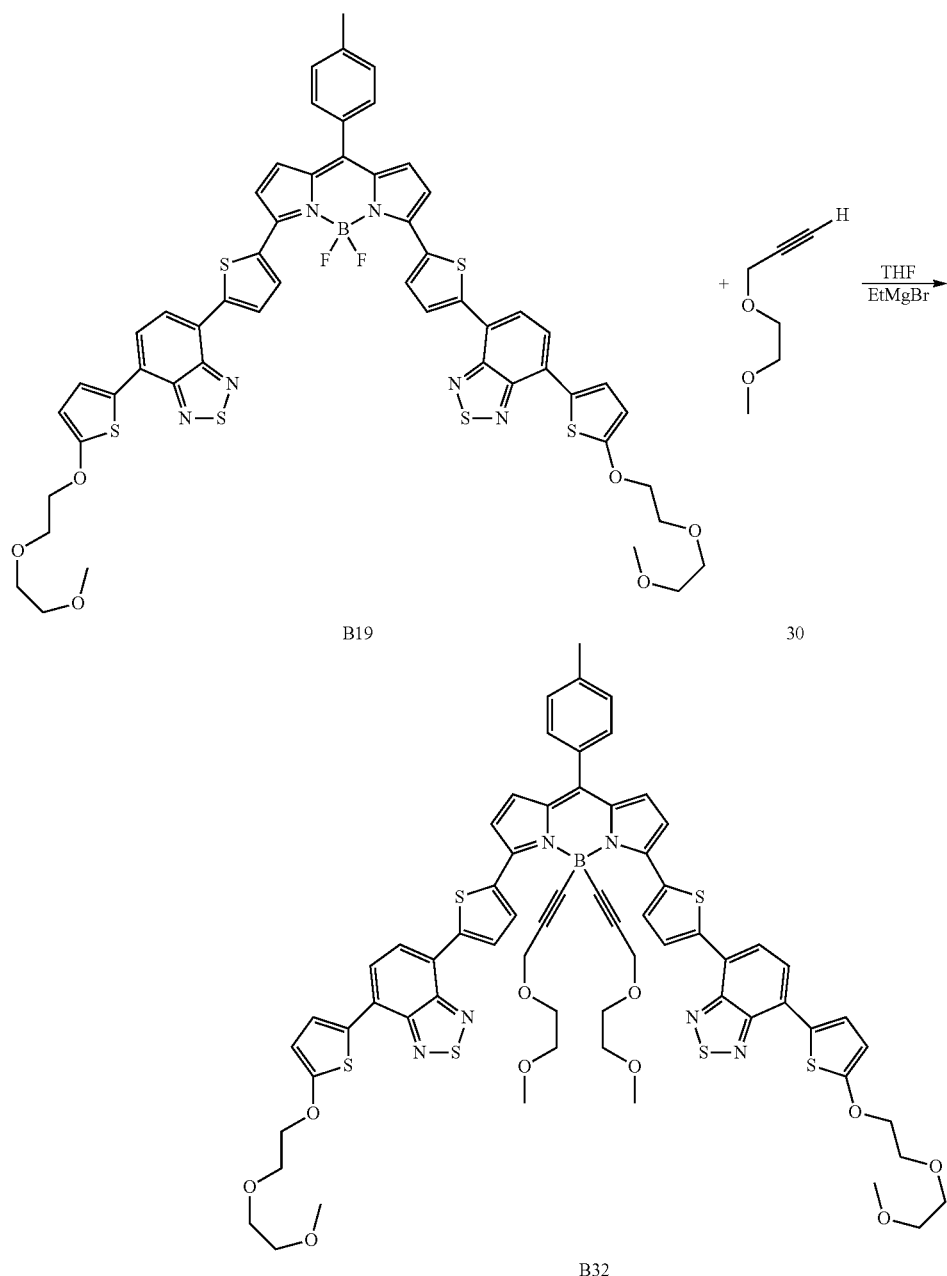

Compound B32 was synthesized by following general procedure n°2, starting from 60 mg (53.8 μmol, 1 eq) of compound B19 as prepared above in example 11, 25 mg (25 μL, 0.215 mmol, 4 eq) of compound 30 and 0.190 mL of a solution of ethylmagnesium bromide (0.190 mmol, 3.5 eq) in a volume of 5 mL of THF. A petroleum ether/ethyl acetate (70/30, v/v) mixture was used to purify the desired compound. 56 mg of compound B32 (43 μmol, Yield: 80%) was obtained.

$^1$H NMR (200 MHz, CDCl$_3$): 2.49 (s, 3H); 3.11 (s, 6H); 3.23-3.26 (m, 4H); 3.34-3.40 (m, 4H); 3.42 (s, 6H); 3.59-3.61 (m, 4H); 3.73-3.76 (m, 4H); 3.89-3.92 (m, 4H); 4.05 (s, 4H); 4.31-4.34 (m, 4H); 6.37 (d, 2H, $^3J$=4.02 Hz); 6.84 (d, 2H, $^3J$=4.35 Hz); 7.05 (s, broad 2H); 7.32 (d, 2H, $^3J$=7.8 Hz); 7.48 (d, 2H, $^3J$=7.8 Hz); 7.70 (d, 2H, $^3J$=7.4 Hz); 7.87 (broad s, 4H); 8.2 (broad s, 2H); 8.86-8.90 (m, 2H).

$^{13}$C NMR (50 MHz, CDCl$_3$): 21.5; 29.8; 58.9; 59.2; 59.4; 68.3; 69.5; 71; 71.8; 72.1; 73.1; 93.8; 106.7; 121.6; 123.9; 124.3; 126.1; 126.7; 127; 128.4; 128.6; 129; 130.7; 132.1; 134.5; 136; 140; 141.8; 149; 152.6; 152.7; 167.2.

ESI-MS: 1302.2 ([M], 100).

Elemental analysis for $C_{66}H_{63}BN_6O_{10}S_6$:

|  | C | H | N |
|---|---|---|---|
| Calculated | 60.82 | 4.87 | 6.45 |
| Found | 60.57 | 4.74 | 6.29 |

Example 24

Synthesis of Compound B33

Compound B33 was synthesized in accordance with the following synthesis scheme:

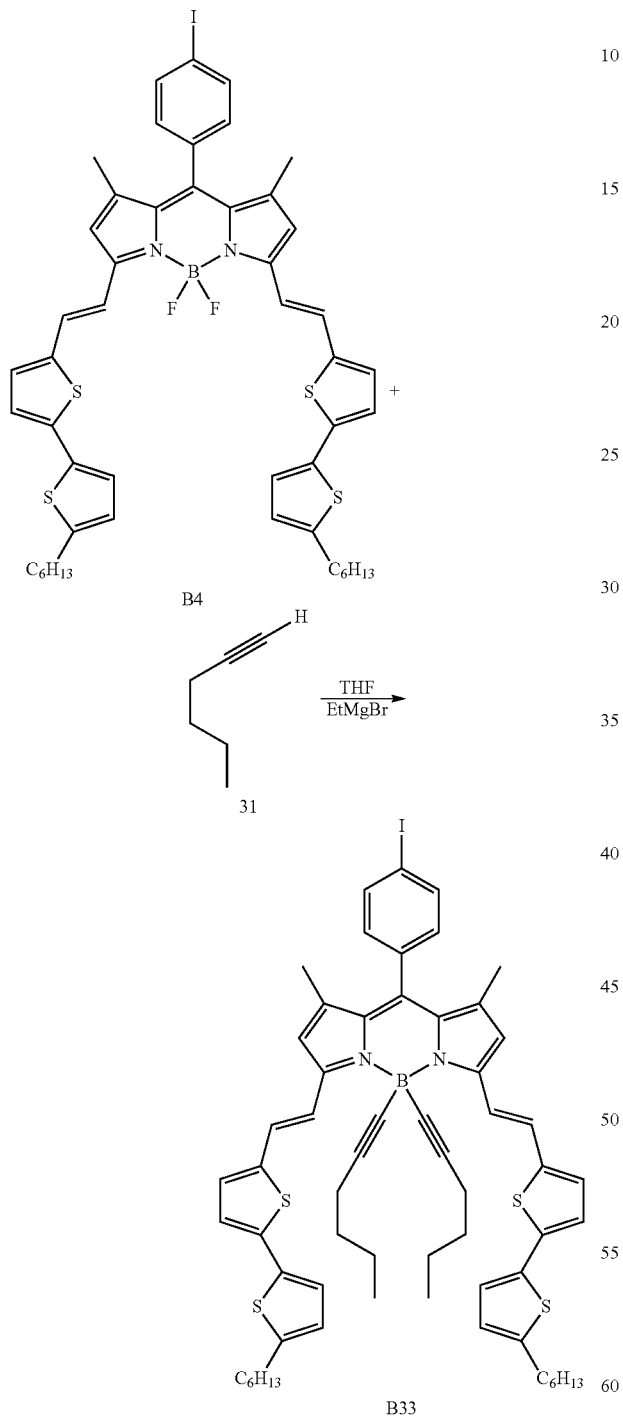

Compound B33 was synthesized by following general procedure n°2, starting from 130 mg (0.134 mmol, 1 eq) of compound B4 as prepared above in example 2, 33 mg (47 µL, 0.4 mmol, 3 eq) of compound 31 and 0.335 mL of a solution of ethylmagnesium bromide (0.335 mmol, 2.5 eq) in a volume of 10 mL of THF. A petroleum ether/toluene (90/10, v/v) mixture was used to purify the desired compound. 120 mg of compound B33 (0.109 mmol, Yield: 81%) was obtained.

$^1$H NMR (200 MHz, CDCl$_3$): 0.82-0.94 (m, 12H); 1.26-1.75 (m, 26H); 1.64-1.75 (m, 4H); 2.17-2.23 (m, 4H); 2.83 (t, 4H, $^3$J=7.5 Hz); 6.60 (s, 2H); 6.73 (d, 2H, $^3$J=3.8 Hz); 7.05-7.25 (m, 10H); 7.83 (d, 2H, $^3$J=8.1 Hz); 8.15 (d, 2H, $^3$J=15.9 Hz).

$^{13}$C NMR (50 MHz, CDCl$_3$): 13.6; 14.1; 15.2; 19.8; 22.4; 22.5; 22.7; 28.9; 30.4; 30.7; 31.7; 68.1; 94.5; 118.5; 121.0; 123.9; 124.1; 125.1; 126.5; 128.8; 131.0; 131.9; 135.1; 135.7; 136.3; 138.2; 139.1; 139.6; 141.9; 146.2; 151.5.

ESI-MS: 1094.2 ([M], 100).

Elemental analysis for C$_{61}$H$_{68}$BIN$_2$S$_4$:

|  | C | H | N |
|---|---|---|---|
| Calculated | 66.90 | 6.26 | 2.56 |
| Found | 66.69 | 6.09 | 2.28 |

Example 25

Synthesis of Compound B34

Compound B34 was synthesized in accordance with the following synthesis scheme:

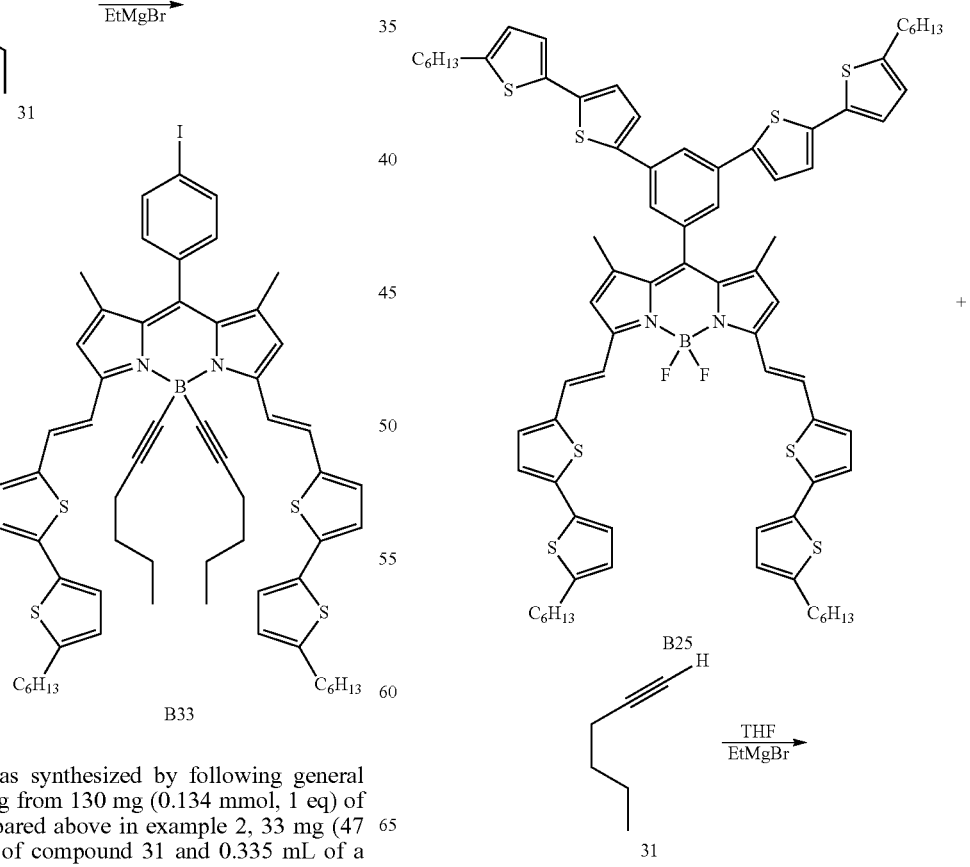

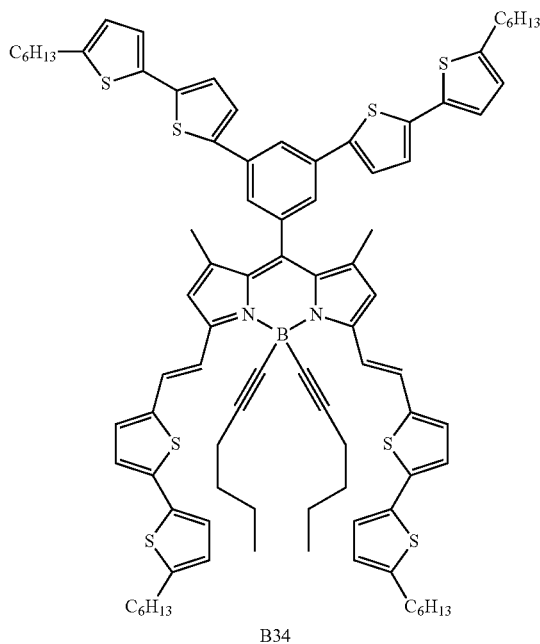

B34

Compound B34 was synthesized by following general procedure n°2, starting from 90 mg (67 µmol, 1 eq) of compound B25 as prepared above in example 16, 17 mg (24 µL, 0.2 mmol, 3 eq) of compound 31 (commercial) and 0.167 mL of a solution of ethylmagnesium bromide (0.167 mmol, 2.5 eq) in a volume of 5 mL of THF. A petroleum ether/toluene (90/10, v/v) mixture was used to purify the desired compound. 90 mg of compound B34 (61.4 µmol, Yield: 91%) was obtained.

$^1$H NMR (200 MHz, CDCl$_3$): 0.84-0.95 (m, 18H); 1.28-1.36 (m, 28H); 1.49-1.71 (m, 16H); 2.21-2.24 (m, 4H); 2.78-2.87 (m, 10H); 6.63 (s, 2H); 6.70-3.75 (m, 4H); 7.03-7.12 (m, 10H); 7.20 (s, 1H); 7.27-7.32 (m, 3H); 7.49-7.50 (m, 2H); 7.84-7.86 (m, 1H); 8.20 (d, 2H, $^3$J=15.9 Hz).

$^{13}$C NMR (50 MHz, CDCl$_3$): 14.1; 14.2; 15.6; 19.8; 22.4; 22.7; 28.9; 30.3; 30.4; 31.7; 31.8; 96.9; 118.5; 121.1; 122.3; 123.8; 124.1; 124.5; 125.1; 126.4; 128.8; 132.1; 134.6; 135.1; 135.6; 134.4; 138.3; 139.0; 139.7; 140.9; 142.0; 146.0; 146.2; 151.5.

ESI-MS: 1464.4 ([M], 100).

Elemental analysis for $C_{89}H_{101}BN_2S_8$:

|  | C | H | N |
| --- | --- | --- | --- |
| Calculated | 72.91 | 6.94 | 1.91 |
| Found | 73.28 | 7.17 | 2.18 |

Example 26

Synthesis of Compound B35

Compound B35 was synthesized in accordance with the following synthesis scheme:

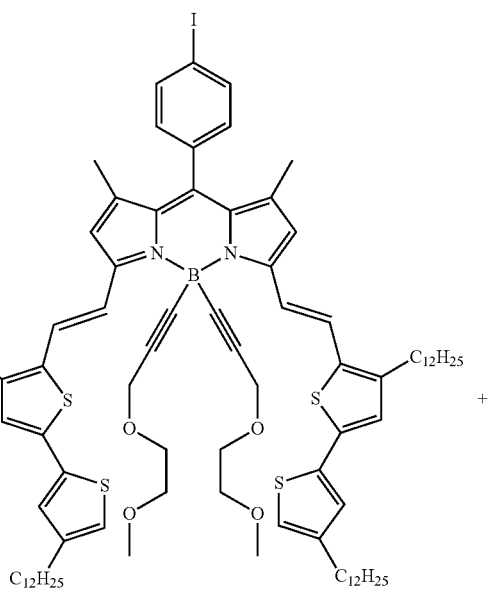

B30

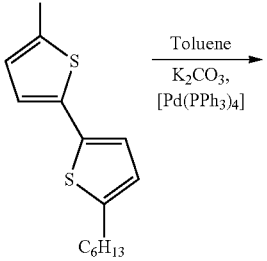

29

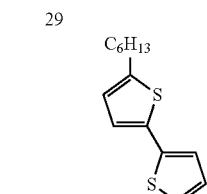

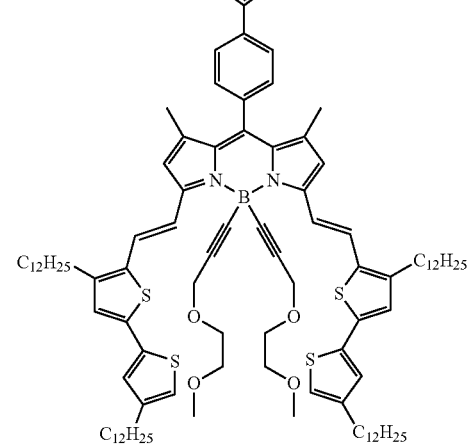

B35

Compound B35 was synthesized by following general procedure n°3, starting from 70 mg (42 µmol, 1 eq) of compound B30 as prepared above in example 21, 20 mg (50.5 µmol, 1.2 eq) of compound 29, 0.11 mL of a 2M solution of K$_2$CO$_3$ and 5 mg of [Pd(PPh$_3$)$_4$](10% molar) in a volume of 5 mL of toluene. A petroleum ether/ethyl acetate (90/10, v/v) mixture was used to purify the desired compound. 43 mg of compound B35 (24.3 µmol, Yield: 58%) was obtained.

$^1$H NMR (400 MHz, CDCl$_3$): 0.86-0.91 (m, 15H): 1.27-1.35 (m, 78H); 1.27-1.35 (m, 16H); 2.61 (t, 4H, $^3$J=7.8 Hz); 2.68 (t, 4H, $^3$J=7.8 Hz): 2.82 (t, 2H, $^3$J=7.4 Hz); 3.20 (s, 6H); 3.35-3.38 (m, 4H); 3.71-3.73 (m, 4H); 4.28 (s, 4H); 6.63 (s, 2H); 6.72 (d, 1H, $^3$J=3.7 Hz); 6.84 (s, 2H); 6.97 (s, 2H); 7.05 (d, 1H, $^3$J=3.3 Hz); 7.12 (d, 1H, $^3$J=3.7 Hz) 7.14 (s, 2H); 7.29-7.37 (m, 5H); 7.73 (d, 2H, $^3$J=8.2 Hz); 7.93 (d, 2H, $^3$J=15.6 Hz).

$^{13}$C NMR (50 MHz, CDCl$_3$): 14.2; 15.3; 22.8; 28.8; 28.9; 29.5; 29.6; 29.7; 29.8; 30.3; 30.5; 30.7; 31.1; 31.7; 32.1; 58.8; 59.6; 68.3; 71.9; 118.4; 119.4; 119.7; 123.7; 124.1; 124.3; 125.0; 125.2; 125.7; 125.9; 126.5; 128.9; 129.6; 132.2; 134.7; 136; 137.1; 137.7; 138.1; 140.1; 141.5; 144.5; 144.7; 146; 151.7.

ESI-MS: 1784.9 ([M], 100).

Elemental analysis for C$_{111}$H$_{157}$BN$_2$O$_4$S$_6$:

|  | C | H | N |
|---|---|---|---|
| Calculated | 74.62 | 8.86 | 1.57 |
| Found | 74.89 | 9.02 | 1.76 |

Example 27

Synthesis of Compound B36

Compound B36 was synthesized in accordance with the following synthesis scheme:

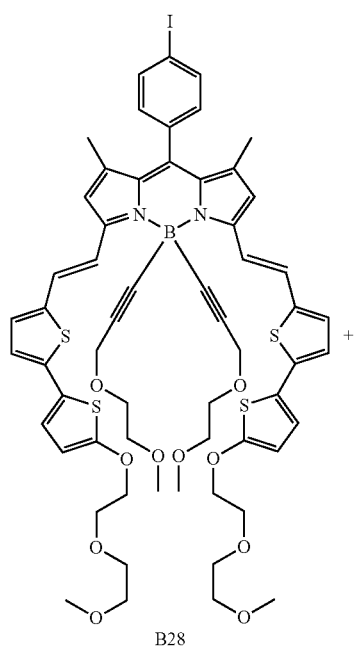

B28

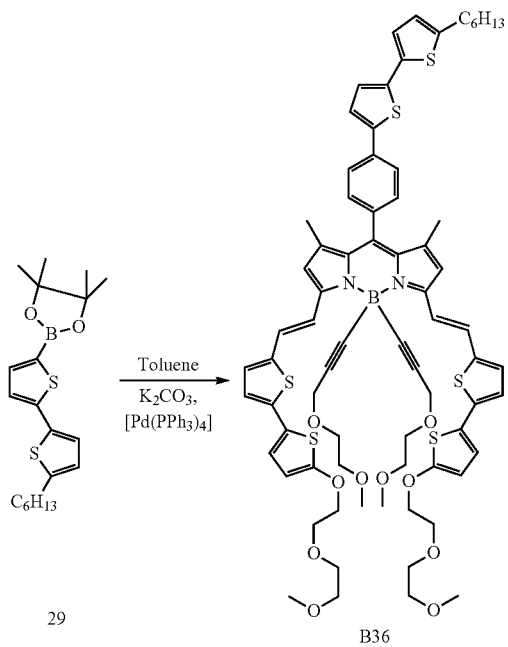

B36

Compound B36 was synthesized by following general procedure n°3, starting from (60/40, v/v) mixture was used to purify the desired compound. 71 mg of compound B36 (53 µmol, Yield: 65%) was obtained.

$^1$H NMR (200 MHz, CDCl$_3$): 0.85-0.91 (m, 3H): 1.26-1.41 (m, 12H); 1.63-1.71 (m, 2H); 2.80 (t, 2H, $^3$J=7.3 Hz): 3.23 (s, 6H); 3.32-3.37 (m, 4H); 3.42 (s, 6H); 3.58-3.3.76 (m, 12H); 3.86-3.90 (m, 4H); 4.24-4.29 (m, 8H); 6.22 (d, 2H, $^3$J=4.2 Hz); 6.61 (s, 2H); 6.72 (d, 1H, $^3$J=3.7 Hz); 6.94-6.96 (m, 4H); 7.03-7.12 (m, 4H); 7.20 (d, 2H, $^3$J=15.8 Hz); 7.32-7.36 (m, 3H); 7.72 (d, 2H, $^3$J=8.5 Hz); 7.96 (d, 2H, $^3$J=15.9 Hz).

$^{13}$C NMR (50 MHz, CDCl$_3$): 14.2; 15.3; 22.7; 28.9; 29.8; 30.3; 31.7; 58.9; 59.2; 59.5; 68.4; 69.5; 70.9; 71.8; 72.1; 73.3; 106.4; 118.4; 120.0; 122.5; 123.3; 123.7; 124.1; 124.2; 124.4; 125.1; 125.8; 126.9; 128.5; 128.8; 129.1; 129.5; 132.1; 134.7; 137.5; 138.1; 139.6; 140.2; 140.9; 141.4; 151.3; 165.1.

ESI-MS: 1348.2 ([M], 100).

Elemental analysis for C$_{73}$H$_{81}$BN$_2$O$_{10}$S$_6$:

|  | C | H | N |
|---|---|---|---|
| Calculated | 64.96 | 6.05 | 2.08 |
| Found | 64.77 | 5.72 | 1.83 |

Example 28

Synthesis of compound B39

Compound B39 was synthesized in accordance with the following synthesis scheme:

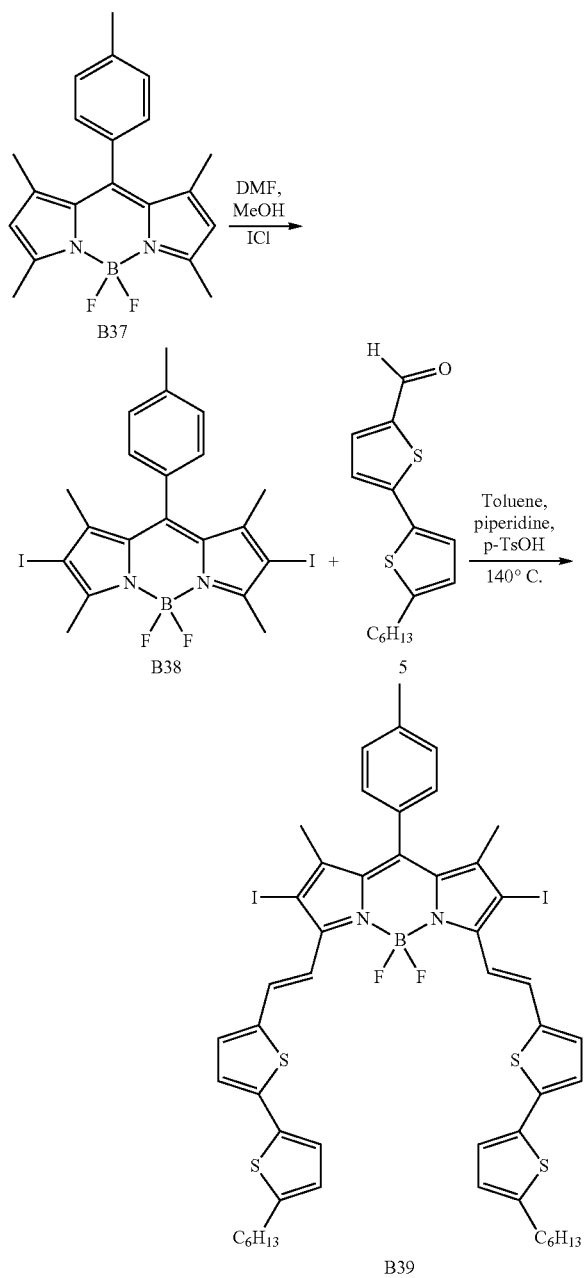

1) First Step: Synthesis of Compound B38

A solution of iodine chloride (3.25 mmol) in methanol was added to a solution of compound B37 (500.0 mg; 1.48 mmol) in a mixture of methanol (30 mL) and dimethylformamide (30 mL). The solution was stirred for 45 min. The organic phase was washed with the aid of an aqueous solution of sodium thiosulphate and water. The aqueous phase was extracted with ether. The expected compound B38 was obtained in a yield of 79% in the form of a red powder after purification by silica gel chromatography with a mixture of solvents as the eluent (petroleum ether/dichloromethane 7/3, v/v).

$^1$H NMR (200 MHz, (CDCl$_3$), δ (ppm): 1.40 (s, 6H); 2.46 (s, 3H); 6.64 (s, 6H); 7.21 (ABsyst, 4H, $^3$J=7.9 Hz).

$^{13}$C NMR (50 MHz, (CDCl$_3$), δ (ppm): 16.1; 17.1; 21.6; 127.7; 130.2; 131.5; 131.7; 131.8; 139.6; 141.9; 145.5; 156.7.

ESI-MS: 590.0 (100).

Elemental analysis for $C_{20}H_{19}BF_2I_2N_2$:

|  | C | H | N |
|---|---|---|---|
| Calculated | 40.71 | 3.25 | 4.75 |
| Found | 40.50 | 2.99 | 4.52 |

2) Second Step: Synthesis of Compound B39

Compound B39 was synthesized by following general procedure n°1, starting from 360 mg (0.8 mmol, 1 eq) of compound B38 obtained as above in the preceding step, and 395 mg (1.41 mmol, 1 eq) of compound 5 in a volume of 20 mL of toluene. A petroleum ether/CH$_2$Cl$_2$ (70/30, v/v) mixture was used to purify the desired compound. 330 mg of compound B39 (0.29 mmol, Yield: 48%) was obtained.

$^1$H NMR (400 MHz, (C$_6$D$_6$): 0.85-0.90 (m, 6H); 1.23-1.26 (m, 12H); 1.43 (s, 6H); 1.52-1.59 (m, 4H); 2.06 (s, 3H); 2.58 (t, 4H, $^3$J=7.7 Hz); 6.48 (d, 2H, $^3$J=3.3 Hz); 6.66 (d, 2H, $^3$J=7.8 Hz): 6.83-6.92 (m, 8H); 8.04 (d, 2H, $^3$J=16 Hz), 8.53 (d, 2H, $^3$J=16 Hz).

ESI-MS: 1110.1 ([M], 100).

Elemental analysis for $C_{50}H_{51}BF_2I_2N_2S_4$:

|  | C | H | N |
|---|---|---|---|
| Calculated | 33.97 | 2.96 | 2.22 |
| Found | 33.84 | 2.72 | 1.96 |

Example 29

Fabrication of Field Effect Transistors

In this example, the fabrication of field effect transistors using the compounds with formula (I) in accordance with the invention is illustrated.

1) Preparation of Field Effect Transistors

Field effect transistors in the bottom contact configuration were fabricated from commercial silicon substrates and as described in the brochure available from the following address: http://www.ipms.fraunhofer.de/content/dam/ipms/common/products/COMEDD/ofete.pdf). The gate contact was constituted by an n-type silicon substrate (doping 3×10$^{17}$/cm$^3$) onto which a 230 nm thick gate oxide (SiO$_2$) had been deposited. The source and drain contacts, which had been pre-lithographed, were constituted by a 10 nm ITO bilayer (indium and tin oxide) as a keying layer covered with 30 nm of gold.

The channel length and width used were respectively 20 μm and 10 mm.

These substrates were cleaned using successive baths of acetone and isopropanol then finally in a UV-ozone oven sold by Novascan under the trade name Novascan 4"UV/Ozone System for 15 minutes before being introduced into a glove box in a neutral atmosphere (N$_2$).

In order to passivate the SiO$_2$ surface, hexamethyldisilazane (HMDS) was deposited by spin-coating (500 rpm for 5 seconds then 4000 rpm for 50 seconds) before thermal annealing at 130° C. for 15 minutes.

The test compounds with formula (I), alone or as a mixture with methyl [6,6]-phenyl-C$_{61}$-butyrate (PC$_{61}$BM), were then deposited by spin-coating using chloroform or chlorobenzene as the solvent with concentrations of compounds with formula (I) of the order of 4 mg/mL and the following deposition parameters: 2000 rpm for 120 seconds then 2500 rpm for 120 seconds.

Once complete, the transistors were left overnight under a high vacuum (<10$^6$ mbar) in order to eliminate all traces of solvent.

2) Characterization of Field Effect Transistors

The characteristics of the transistors (transfer characteristic at constant gate voltage: $I_{ds}=f(V_{ds})$ in which $I_{ds}$ is the drain source intensity and $V_{ds}$ is the drain source voltage) as well as their transfer characteristic under fixed drain voltage ($I_{ds}=f(V_g)$ in which $V_g$ is the gate voltage) were measured at a probe station (controlled atmosphere of $N_2$) with the aid of a model 4200 parameter analyser from Keithley. In all cases, the mobility of the charge carriers was estimated from the transfer characteristics in saturation mode using the standard format.

FIG. 1 represents the characteristics of transistors with a channel constituted by compound B4 of the invention and shows the ambipolar nature of this molecule. FIG. 1a provides the output characteristics for (a) the holes ($I_{ds}$ in μA as a function of $V_{ds}$ in volts) and (b) the electrons ($I_{ds}$ in nA as a function of $V_{ds}$ in volts).

The mobilities extracted for the various molecules studied (independently of the solvent used) are summarized in Table 1 below. The mobilities of the electrons ($\mu_e$) and holes ($\mu_h$) were estimated from the transfer characteristics for the transistors. Only molecule B4 exhibited an ambipolar character.

TABLE 1

| Molecule | $\mu_h$ (cm$^2$/Vs) | $\mu_e$ (cm$^2$/Vs) |
|---|---|---|
| B10 | 1 × 10$^{-4}$ | / |
| B4 | 1 × 10$^{-3}$ | 1 × 10$^{-3}$ |
| B2 | 1 × 10$^{-8}$ | / |
| B12 | 6 × 10$^{-7}$ | / |
| B8 | 3 × 10$^{-4}$ | / |
| B9 | 9 × 10$^{-4}$ | / |
| B35 | 2 × 10$^{-7}$ | / |
| B28 | 4 × 10$^{-4}$ | / |

3) Fabrication of Photovoltaic Cells

The photovoltaic cells studied were produced in the following manner. Glass/ITO substrates (Lumtec®, $R_s$<15Ω/□) were cleaned in an ultrasound bath (15 minutes, 45° C.) successively in acetone, isopropanol then in deionized water. They were then treated in a UV-ozone oven sold under the trade name Novascan 4" UV/Ozone System by Novascan for 30 minutes before depositing a layer of poly(3,4-ethylenedioxythiophene:sodium poly(styrene sulphonate) (PEDOT:PSS). The PEDOT:PSS (Clevios, grade PH) was filtered through a 0.45 μm membrane then deposited by spin-coating (1550 rpm, 180 seconds) in order to obtain a homogeneous layer of approximately 40 nm. After deposition, the samples were placed in an oven under low vacuum for 30 minutes at 120° C. then introduced into a glove box under an inert atmosphere ($N_2$).

Solutions of compounds in accordance with the invention ($B_n$) mixed with PC$_{61}$BM (NanoC) with $B_n$:PC$_{61}$BM weight ratios from 1:0.5 to 1:3 were prepared in advance using chloroform (5 mg/mL of compound $B_n$) or chlorobenzene (40 mg/mL of $B_n$) as the solvent. The solutions were stirred for a minimum of 2 days at approximately 50° C. then at approximately 110° C. 30 minutes prior to deposition. The substrates were heated to 120° C. for 30 minutes inside the glove box before deposition.

The active layer of $B_n$:PC$_{61}$BM was deposited by spin-coating using a two-step programme: a first deposition step at 2200 rpm for 180 seconds then a second deposition step at 2500 rpm for 120 seconds.

The photovoltaic device was finished by depositing the metallic cathode using the Joule effect under high vacuum (<10$^{-6}$ mbar) through a planar mask. Two configurations were tested: either an aluminium cathode (120 nm) or a Ca/Al bilayer (20/120 nm). In this second configuration, any thermal annealing (post-production) was carried out before deposition of the cathode. Each substrate contained 4 independent photovoltaic cells (3×3 mm$^2$).

4) Characterization of Photovoltaic Cells

The current-voltage characteristics (I-V) of the photovoltaic cells prepared in this manner were measured using a source meter (Keithley® 2400 Source Meter). The standard illumination was provided by a solar radiation simulator equipped with a 150 W xenon lamp sold by Lot Oriel, equipped with a filter delivering an AM1.5G spectrum. The power received by the cell (100 mW/cm$^2$) was calibrated with the aid of a ThorLabs® Power Meter.

The photovoltaic parameters measured are summarized in Table 2 below. The thicknesses indicated (d) for the active layer were measured using a Dektak® Profilometer.

TABLE 2

Table 2: photovoltaic parameters measured on optimized instruments.

| Molecule | TB$_n$:PC$_{61}$BM ratio | $V_{oc}$ (V) | $J_{sc}$ (mA/cm$^2$) | FF (%) | η (%) | Anneal | d (nm) |
|---|---|---|---|---|---|---|---|
| B10 | 1:2 $^{a)}$ | 0.76 | 5.84 | 31 | 1.4 | 70° C., 20 min | 110 ± 10 |
| B4 | 1:0.8 $^{a)}$ | 0.60 | 7.7 | 45 | 2.1 | 100° C., 20 min | 110 ± 10 |
| B2 | 1:2 $^{a)}$ | 0.56 | 5.1 | 30 | 0.9 | — | 110 ± 10 |
| B12 | 1:1 $^{a)}$ | 0.55 | 8.5 | 32 | 1.5 | 80° C., 20 min | 110 ± 10 |
| B4 | 1:0.8 $^{b)}$ | 0.74 | 14.2 | 43 | 4.5 | 100° C., 10 min | 165 ± 10 |
| B2 | 1:1 $^{b)}$ | 0.51 | 3.3 | 33 | 0.6 | 80° C., 10 min | 165 ± 10 |
| B12 | 1:0.8 $^{b)}$ | 0.57 | 2.3 | 30 | 0.4 | — | 165 ± 10 |
| B4 | 1:0.5 $^{c)}$ | 0.7 | 14.3 | 47 | 4.7 $^{c)}$ | 120° C., 20 min | 165 ± 10 |
| B3 | 1:2 | 0.54 | 2.28 | 29 | 0.36 | — | 80 ± 10 |
| B28 | 1:1 | 0.4 | 9.57 | 42 | 1.58 | — | 80 ± 10 |
| B36 | 1:1 | 0.34 | 3.12 | 32 | 0.34 | — | 80 ± 10 |
| B33 | 1:1 | 0.63 | 3.99 | 30 | 0.76 | — | 80 ± 10 |
| B29 | 1:1 | 0.48 | 8.00 | 42 | 1.64 | 80° C., 20 min | 80 ± 10 |
| B12 | 1:1 | 0.68 | 8.83 | 31 | 1.87 | — | 80 ± 10 |
| B34 | 1:1 | 0.52 | 1.35 | 28 | 0.20 | — | 80 ± 10 |
| B27 | 1:2 | 0.68 | 3.40 | 31 | 0.71 | — | 110 ± 10 |

TABLE 2-continued

Table 2: photovoltaic parameters measured on optimized instruments.

| Molecule | $TB_n:PC_{61}BM$ ratio | $V_{oc}$ (V) | $J_{sc}$ (mA/cm$^2$) | FF (%) | η (%) | Anneal | d (nm) |
|---|---|---|---|---|---|---|---|
| B35 | 1:1 | 0.52 | 1.99 | 28 | 0.30 | — | 110 ± 10 |
| B31 | 1:2 | 0.58 | 2.25 | 27 | 0.35 | — | 110 ± 10 |
| B9 | 1:2 | 0.49 | 1.5 | 19 | 0.20 | — | 110 ± 10 |
| B30 | 1:2 | 0.56 | 2.50 | 29 | 0.42 | — | 110 ± 10 |
| B8 | 1:2 | 0.52 | 1.77 | 28 | 0.29 | — | 110 ± 10 |
| B19 | 1:1 | 0.66 | 7.63 | 31 | 1.55 | — | 80 ± 10 |
| B20 | 1:1 | 0.80 | 3.33 | 27 | 0.72 | 100° C., 10 min | 80 ± 10 |
| B35 | 1:2 | 0.498 | 2.16 | 28 | 0.30 | — | 110 ± 10 |
| B6 | 1:0.8 | 0.67 | 1.96 | 33 | 0.43 | 10 min, 80° C. | 80 ± 10 |
| B7 | 1:0.8 | 0.57 | 2.15 | 28 | 0.35 | 10 min, 80° C. | 80 ± 10 |

$V_{oc}$: open circuit voltage, $J_{sc}$: short-circuit current density, FF: form factor and η: photovoltaic conversion efficiency.
The production conditions were respectively as follows:
$^{a)}$ chloroform solvent with a concentration of 5 mg/mL of $B_n$;
$^{b)}$ chlorobenzene solvent with a concentration of 40 mg/mL of $B_n$ and an Al cathode;
$^{c)}$ chlorobenzene solvent with a concentration of 40 mg/mL of $B_n$ and a Ca/Al cathode.

The form factor (FF) was calculated using the following formula:

$$FF = \frac{Pmax}{Pmax_{abs}} = \frac{Ipm \times Vpm}{Isc \times Voc}$$

in which:
Pmax=maximum electrical power measured
Pmax$_{abs}$=absolute maximum electrical power
$I_{pm}$=current intensity at maximum electrical power
$V_{pm}$=voltage at maximum electrical power
$I_{sc}$=short-circuit intensity
$V_{oc}$=short circuit voltage.
The efficiency (η) for each of the cells was calculated using the following formula:

$$\eta = \frac{Pmax}{Pi} = \frac{Ipm \times Vpm}{Pis \times S} = \frac{FF \times Isc \times Voc}{Pis \times S}$$

in which:
Pi=incident luminous power density
Pis=incident surface luminous power density (fixed at 100 mW/cm$^2$)
S=Surface area of the photovoltaic cell
These results show that the photovoltaic conversion cells have a $V_{oc}$ which may reach 0.74 V for the cell prepared using the compound B10, or even 0.76 V for the cell prepared with the compound B4, which is higher than that obtained with the best performing cells contained in the current literature (Konarka P3HT/PCBM cell: $V_{oc}$<0.65 V; C. J. Brabec et al., Adv. Mater., 2009, 21, 1323-1338).

Figure 2:
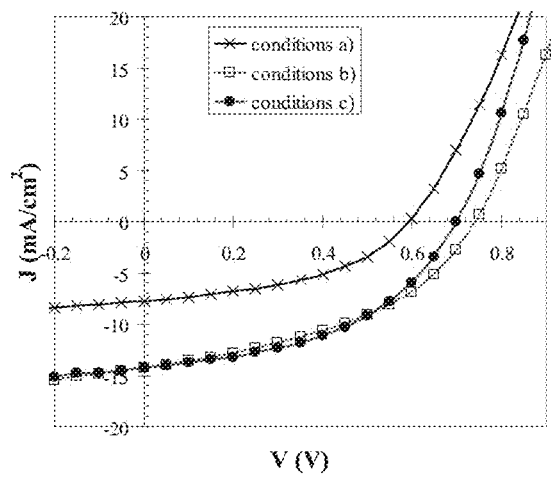

The (J-V) curves obtained with the molecule B4 are represented in the accompanying FIG. 2 in which the current density (J) in mA/cm$^2$ is a function of the voltage (V) in volts. In this figure, the curve a) (symbol X) corresponds to the solvent chloroform production conditions with a concentration of 5 mg/mL of $B_n$; the curve b) (symbol □) corresponds to the chlorobenzene solvent production conditions with a concentration of 40 mg/mL of $B_n$ and an Al cathode; and the curve c) (symbol ●) corresponds to the chlorobenzene solvent production conditions with a concentration of 40 mg/mL of $B_n$ and a Ca/Al cathode.

Figure 3:
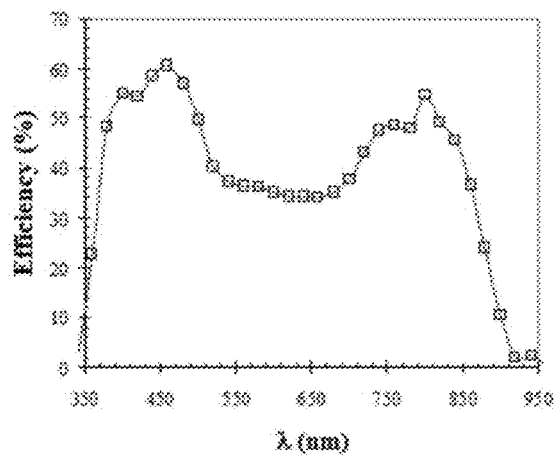

The high short-circuit current density (approximately 14.2 mA/cm$^2$) measured under conditions b) and c) for the molecule B4 is compatible with the broad spectral response measured for a cell produced in accordance with conditions b) illustrated in the accompanying FIG. 3 on which the yield of the photovoltaic cell produced from B4 under the conditions: b) chlorobenzene solvent with a concentration of 40 mg/mL of $B_n$ and an Al cathode (in %) is a function of the wavelength λ (in nm). This spectral response was measured on a dedicated bench with a 250 W Oriel halogen lamp as the source passing through a band pass optical wheel filter.

Figure 4:
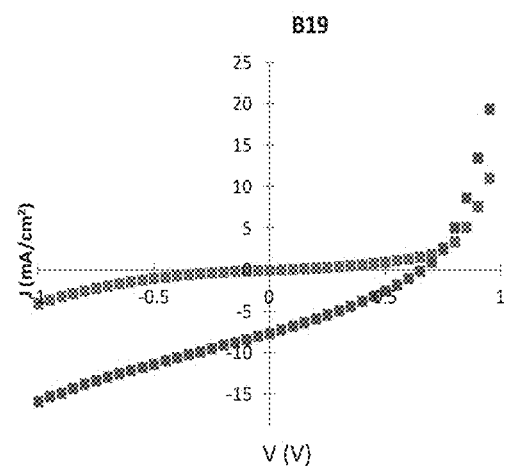
Figure 5:
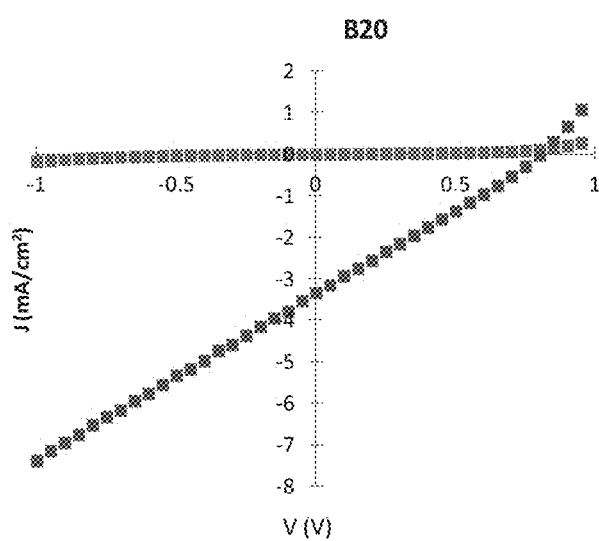

The accompanying FIGS. 4 and 5 respectively provide the (J-V) curves obtained with the molecules B19 (no heat treatment; $V_{oc}$=0.66 V; $J_{cc}$=7.63 mA/cm$^2$; FF=0.31; PCE=1.55%) and B20 (after heat treatment at 100° C. for 10 min.: $V_{oc}$=0.80 V; $J_{oc}$=3.33 mA/cm$^2$; FF=0.27; PCE=0.72%). In these figures, the current density (J) in mA/cm$^2$ is a function of the voltage (V) in volts, without illumination (high, nearly flat curve) and under standard illumination (100 mW/cm$^2$).

The invention claimed is:
1. Boron dipyrromethene derivative having the following formula (I):

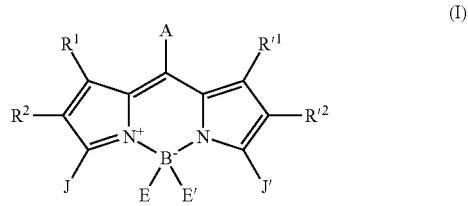

in which:
A is selected from the group consisting of a hydrogen atom; a $C_1$-$C_6$ alkyl chain; a phenyl ring; a phenyl ring substituted with one or more W groups selected from a halogen atom, a linear or branched $C_2$-$C_{20}$ carbon chain which may contain one or more heteroatoms selected from S, O and N, a formyl, carboxyl, thiophene, bis-thiophene or ter-thiophene group, a phenyl ring, and a phenyl ring substituted with a linear or branched $C_2$-$C_{20}$ carbon chain which may contain one or more heteroatoms selected from S, O, Si and N, the or said W groups being in the 3, 4 and/or 5 position of said phenyl ring; and an aromatic ring containing a heteroatom selected from S, O, N and Si, said aromatic ring optionally being substituted with a halogen atom or a linear or branched $C_2$-$C_{20}$ carbon chain which may contain one or more heteroatoms selected from S, O and N;

$R^1$, $R^2$, $R'^1$, $R'^2$, which may be identical or different, is selected from the group consisting of a hydrogen atom, a halogen atom and a $C^1$-$C^6$ alkyl radical; the substituents $R^1$ and $R^2$ together, and $R'^1$ and $R'^2$ together may also form a saturated or unsaturated carbon cycle containing 5 or 6 atoms, said cycle optionally containing a heteroatom selected from S, Si, O, N and P;

E and E', which may be identical or different, are selected from the group consisting of a fluorine atom and a group with the following formula (II): —C≡C-L, in which L is selected from a single bond; a $C_1$-$C_{10}$ alkenylene and a saturated, linear or branched, $C_1$-$C_{20}$ carbon chain interrupted by 1 to 10 oxygen atoms and in which case L is terminated by a group selected from a $C_1$-$C_4$ alkyl radical, a phosphate group and a silyl group; L may also represent a polyaromatic motif which may be substituted or comprising the heteroatoms S, O or N such as a thiophene, polythiophene, pyrene, perylene, arylene, triazatruxene or truxene group;

J represents a group with the following formula (III):

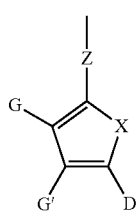
(III)

in which:
Z is a linker providing the connection with the boron dipyrromethene group with formula (I) and is selected from —CH=CH—, —C≡C— and a C—C bond connected directly to the boron dipyrromethene group with formula (I);
X is selected from the heteroatoms N, O, Si and S;
D represents a group selected from the groups consisting of a thiophene, a furan, a pyridine, a naphthalene, an anthracene, a pyrene, a perylene and a benzothiadiazole group, substituted with one or more linear or branched chains containing 2 to 20 carbon atoms which may contain one or more heteroatoms selected from S, O, Si and N;

G and G', which may be identical or different, are selected from the group consisting of a hydrogen atom and a linear or branched $C_2$-$C_{20}$ carbon chain which may contain one or more heteroatoms selected from S, O, Si and N, it being understood that G and G' together, as well as G' and D together, may also form, together with the atoms of the carbon cycle to which they are connected, a fused cycle selected from thienothiophenes and thienopyrroles;

J' represents a methyl group or a group identical to the group J with formula (III) as defined above.

2. Boron dipyrromethene derivative according to claim 1, wherein A is selected from a hydrogen atom, an unsubstituted phenyl group, a substituted phenyl group, a thiophene group and a substituted thiophene group.

3. Boron dipyrromethene derivative according to claim 2, wherein A is selected from the groups methylphenyl, iodophenyl and iodothiophene.

4. Boron dipyrromethene derivative according to claim 1, wherein $R^1$ and $R'^1$ are identical and represent a methyl radical and $R^2$ and $R'^2$ are identical and represent a hydrogen atom.

5. Boron dipyrromethene derivative according to claim 1, wherein said Boron dipyrromethene is selected from the groups consisting of the compounds B2, B3, B4, B5, B6, B8, B9, B12, B13, B16, B17, B22, B25, B26, B27, B28, B29, B30, B31, B33, B34, B35, B36 and B39 with the following formulae:

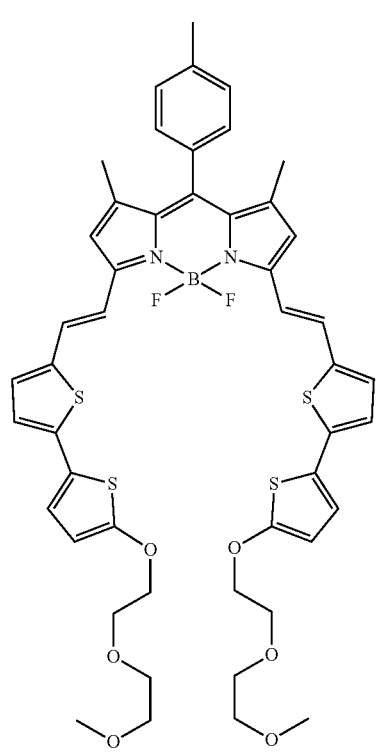
B2

B3
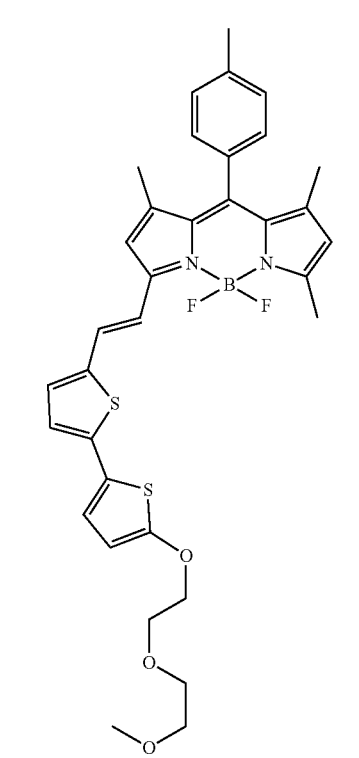
B4
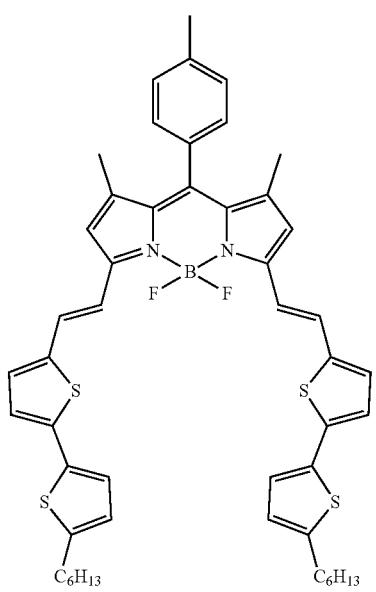
B5
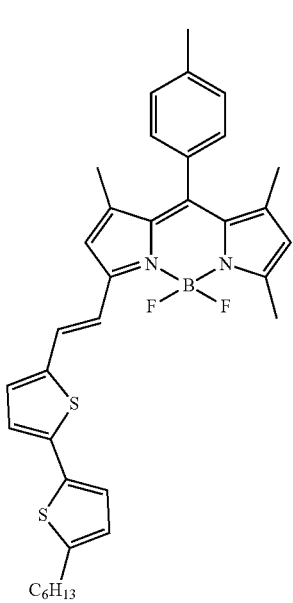
B6
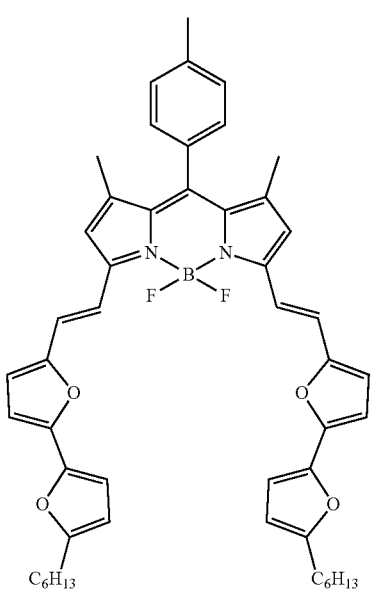

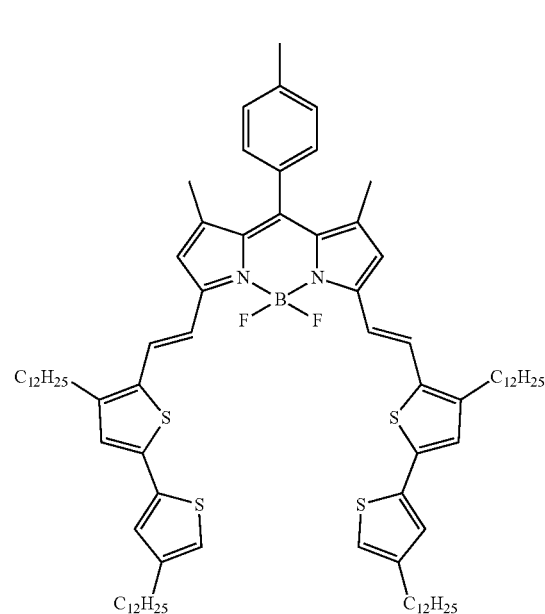
B8
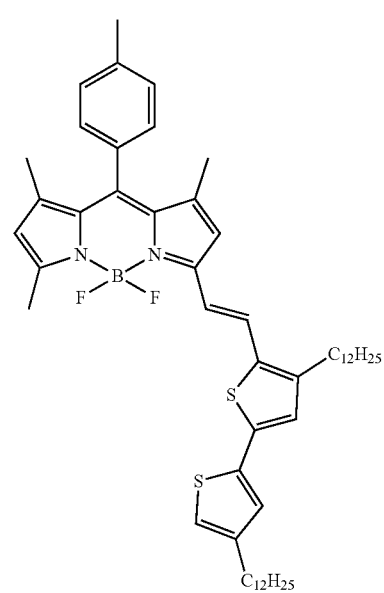
B9
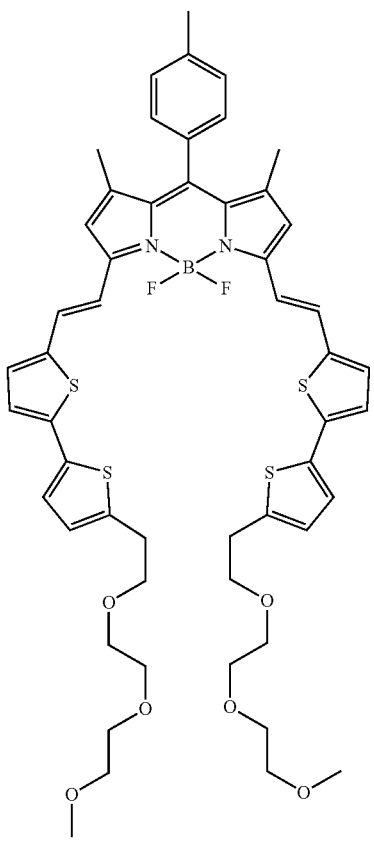
B12
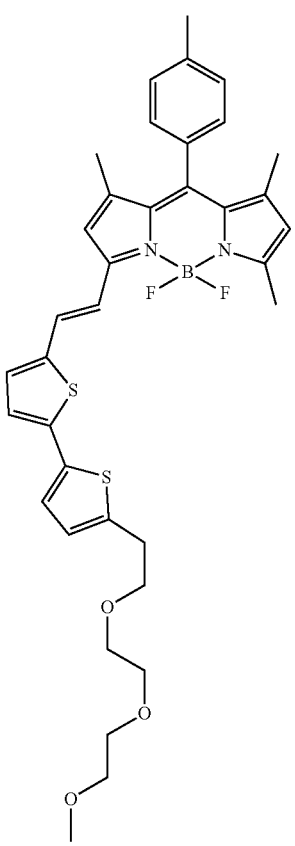
B13

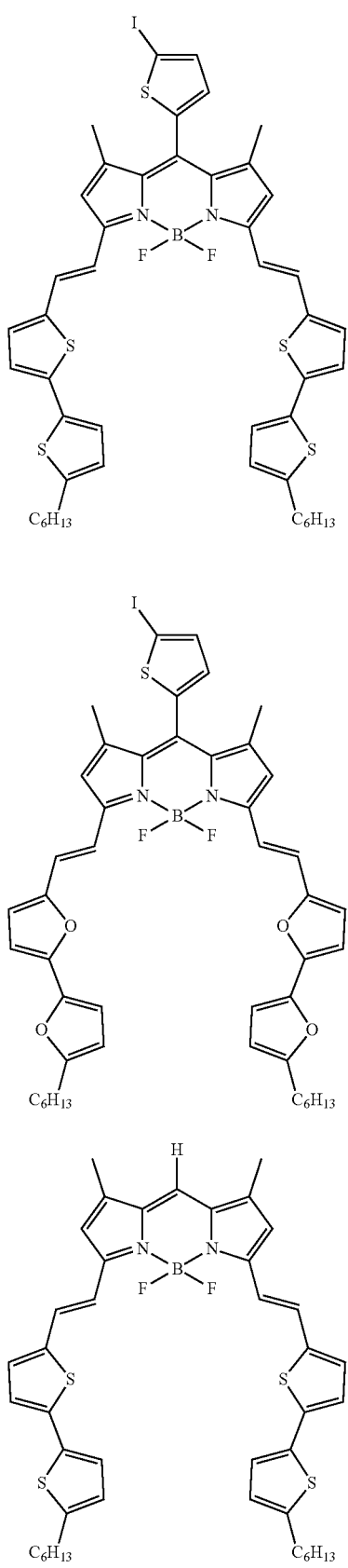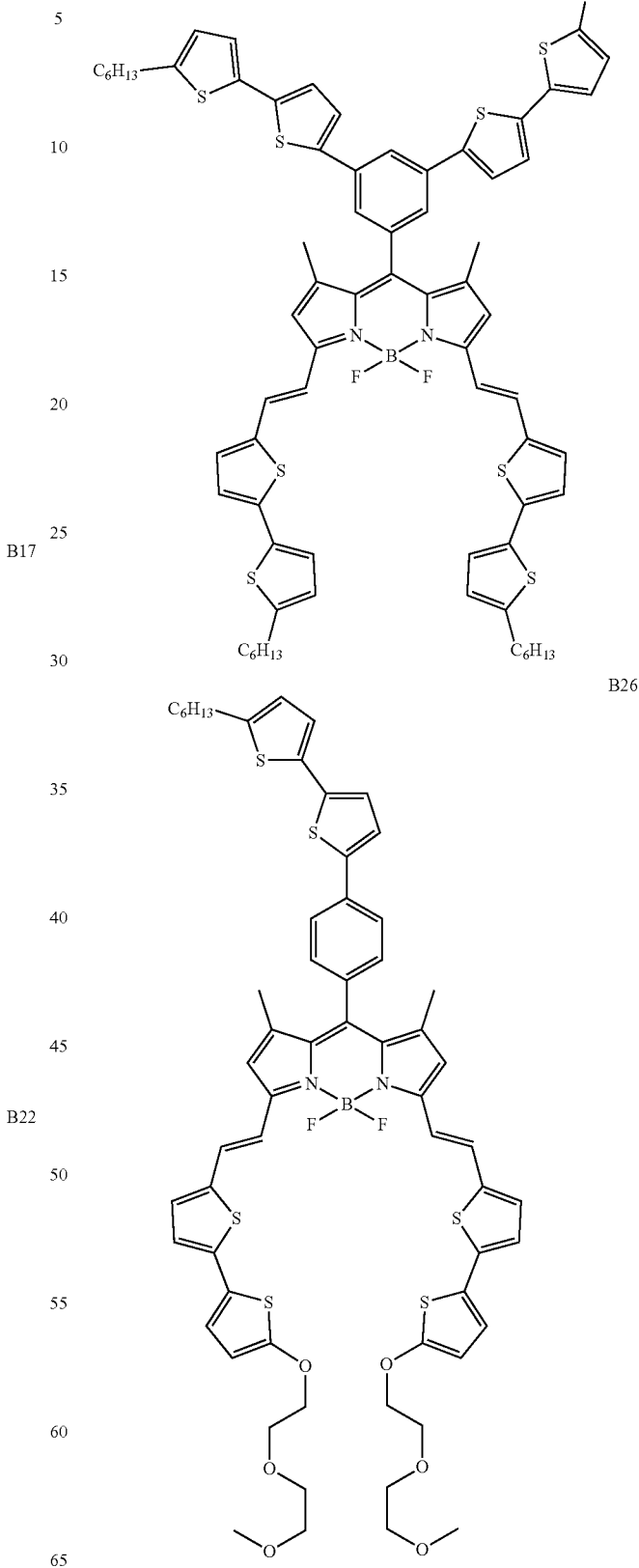

B27
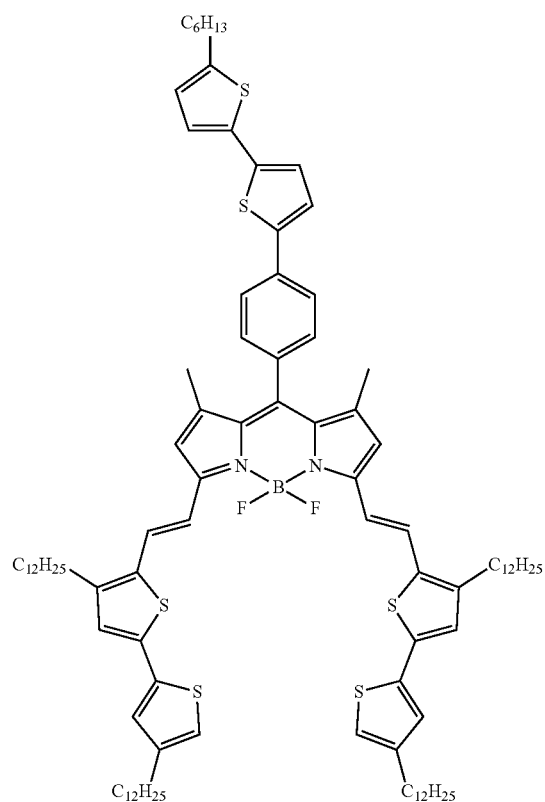
B29
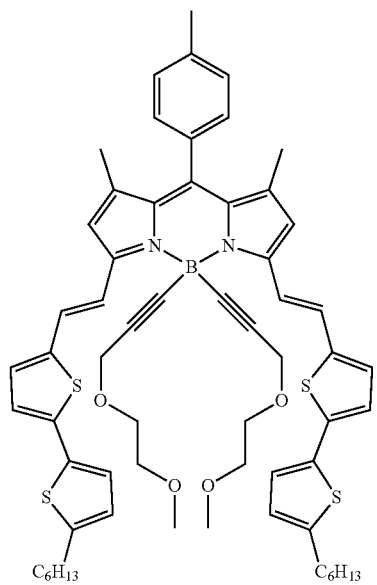
B28
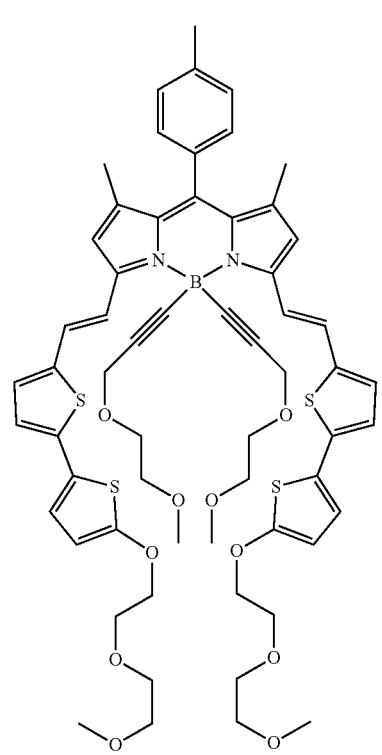
B30
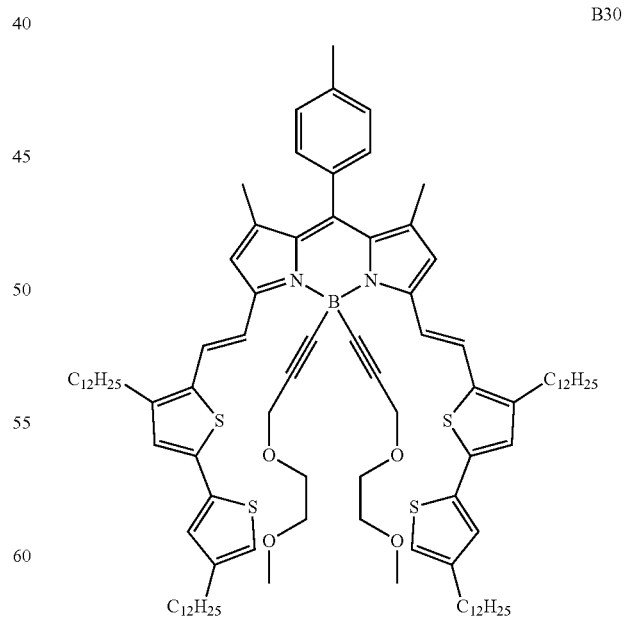

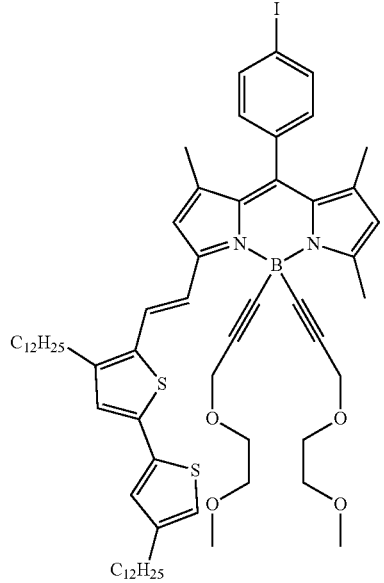
B31
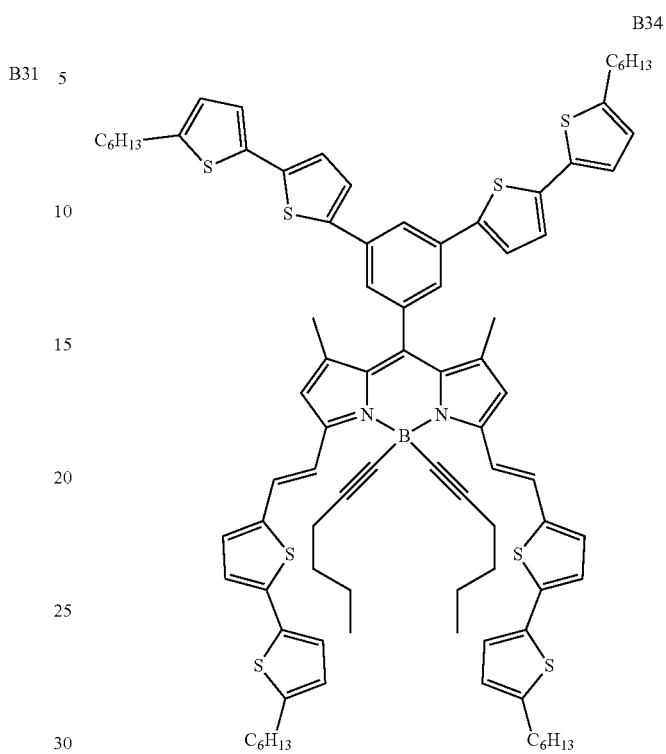
B34
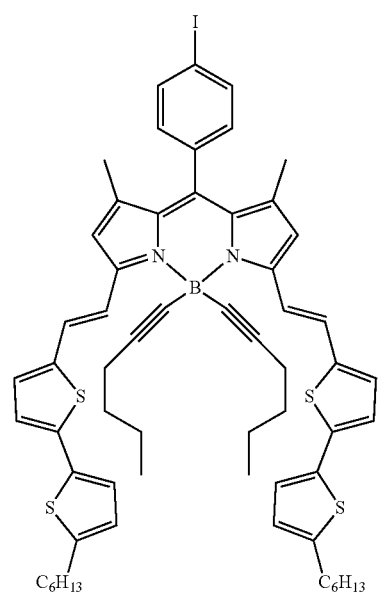
B33
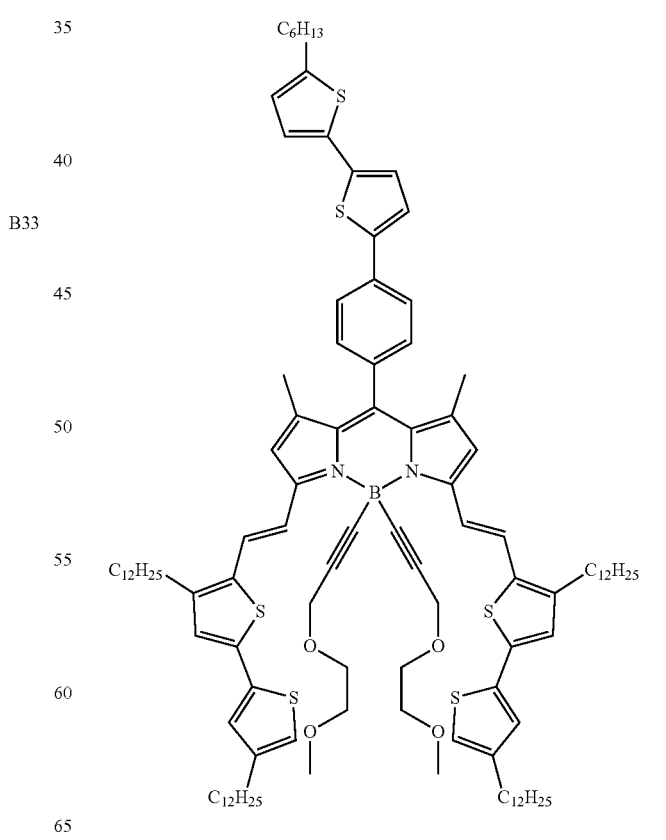
B35

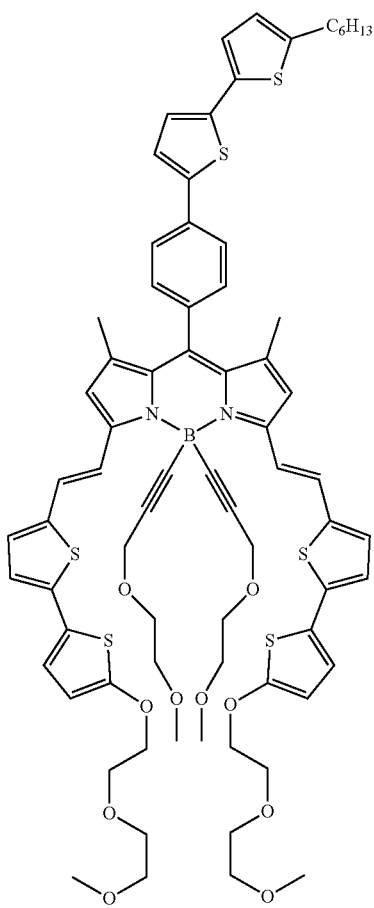

B36

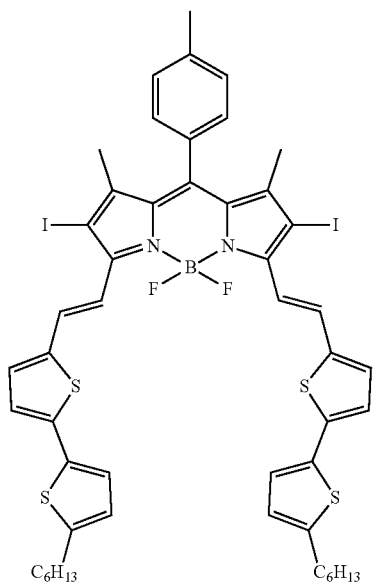

B39

6. Boron dipyrromethene derivative according to claim 5, wherein said Boron dipyrromethene is selected from the group consisting of B2, B4, and B28.

7. A bulk heterojunction in a photovoltaic cell comprising an electron donor is at least one compound with formula (I) as defined in claim 1.

8. A semiconductor material for the production of an ambipolar field effect transistor, said material comprising at least one compound with formula B4 as defined in claim 6.

9. Photovoltaic cell comprising at least one support, a positive electrode, an active layer (heterojunction) comprising at least one electron donor and at least one electron acceptor, a negative electrode, wherein the electron donor is selected from compounds with formula (I) as defined in claim 1.

10. Photovoltaic cell according to claim 9, wherein the electron acceptor is selected from the group consisting of fullerene derivatives, carbon nanotubes, perylene derivatives and tetracyanoquinodimethane derivatives.

11. Cell according to claim 9, wherein the compound with formula (I)/electron acceptor weight ratio varies from 10/1 to 1/3.

12. Cell according to claim 9, wherein the negative electrode is an aluminium electrode.

13. Cell according to claim 9, a buffer layer is interposed between the active layer and the positive electrode, said buffer layer being constituted by a blend of two polymers: poly(3,4-ethylenedioxythiophene) and sodium poly(styrene sulphonate).

14. Cell according to claim 9, wherein a buffer layer is interposed between the active layer and the negative electrode, said buffer layer being constituted by a layer of lithium fluoride.

15. Ambipolar field effect transistor comprising a source, a drain, a gate to which a control voltage is applied, as well as a channel constituted by an organic semiconductor, said channel being in contact with the insulator or the gate oxide, said transistor being wherein the organic semiconductor is a compound with formula B4 as defined in claim 6.

16. Boron dipyrromethene derivative having the following formula (I):

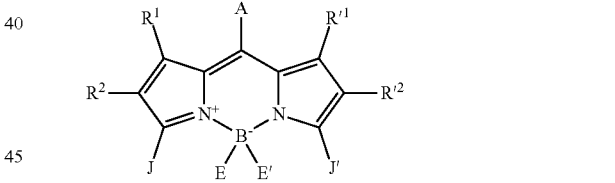

in which:
A is selected from the group consisting of
  a hydrogen atom;
  a $C_1$-$C_6$ alkyl chain;
  a phenyl ring;
  a phenyl ring substituted with one or more W groups selected from a halogen atom, a linear or branched $C_2$-$C_{20}$ carbon chain which may contain one or more heteroatoms selected from S, O and N, a formyl, carboxyl, thiophene, bis-thiophene or ter-thiophene group, a phenyl ring, a phenyl ring substituted with a linear or branched $C_2$-$C_{20}$ carbon chain which may contain one or more heteroatoms selected from S, O, Si and N, the or said W groups being in the 3, 4 and/or 5 position of said phenyl ring; and
  an aromatic ring containing a heteroatom selected from S, O, N and Si, said aromatic ring optionally being substituted with a halogen atom or a linear or branched $C_2$-$C_{20}$ carbon chain which may contain one or more heteroatoms selected from S, O and N;

$R^1$, $R^2$, $R'^1$, and $R'^2$, are each a hydrogen atom;

E and E', which may be identical or different, are selected from the group consisting of a fluorine atom and a group with the following formula (II): —C≡C-L, in which L is selected from a single bond, a $C_1$-$C_{10}$ alkenylene; and a saturated, linear or branched, $C_1$-$C_{20}$ carbon chain interrupted by 1 to 10 oxygen atoms and in which case L is terminated by a group selected from a $C_1$-$C_4$ alkyl radical, a phosphate group and a silyl group; L may also represent a polyaromatic motif which may be substituted or comprising the heteroatoms S, O or N such as a thiophene, polythiophene, pyrene, perylene, arylene, triazatruxene or truxene group;

J represents a group with the following formula (III):

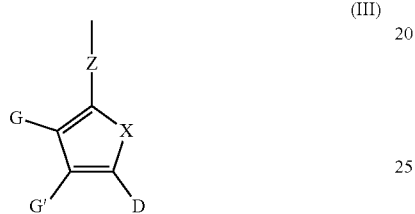

(III)

in which:

Z is a linker providing the connection with the boron dipyrromethene group with formula (I) and is selected from —CH═CH—, —C≡C— and a C—C bond connected directly to the boron dipyrromethene group with formula (I);

X is selected from the heteroatoms N, O, Si and S;

D represents a group selected from the group consisting of arylene, heteroarylene, benzothiadiazole, and $C_2$-$C_{20}$ carbon chains, which may be linear or branched which may contain one or more heteroatoms selected from S, O, Si and N;

G and G', which may be identical or different, are selected from the group consisting of a hydrogen atom, a linear or branched $C_2$-$C_{20}$ carbon chain which may contain one or more heteroatoms selected from S, O, Si and N, wherein G and G' together, as well as G' and D together, may also form, together with the atoms of the carbon cycle to which they are connected, a fused cycle selected from thienothiophenes and thienopyrroles; and J' represents a methyl group or a group identical to the group J with formula (III) as defined above.

17. Boron dipyrromethene derivative according to claim 16, wherein said Boron dipyrromethene is selected from the groups consisting of the compounds B19, B20, B21, and B32 with the following formulae:

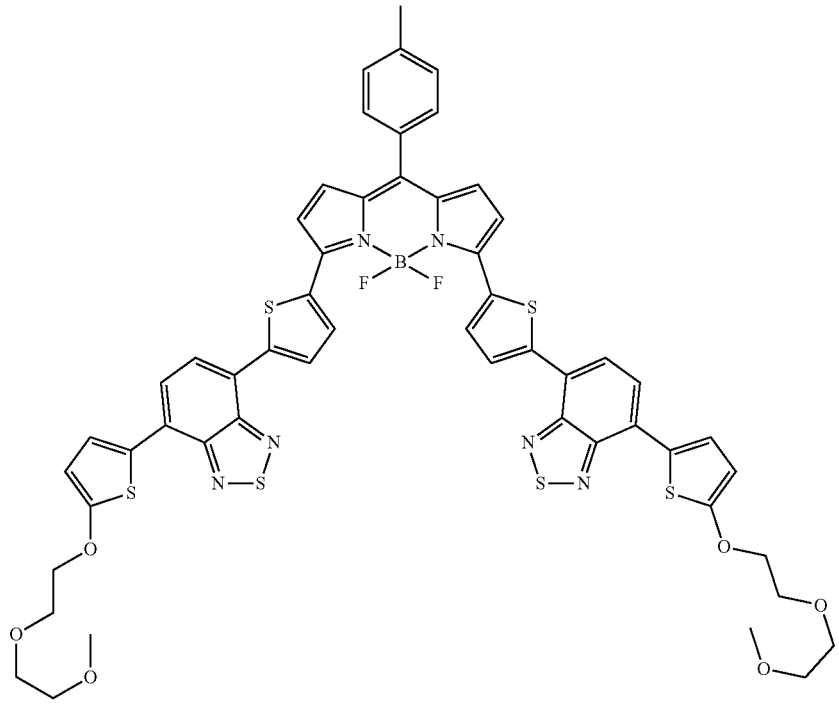

B19

B20
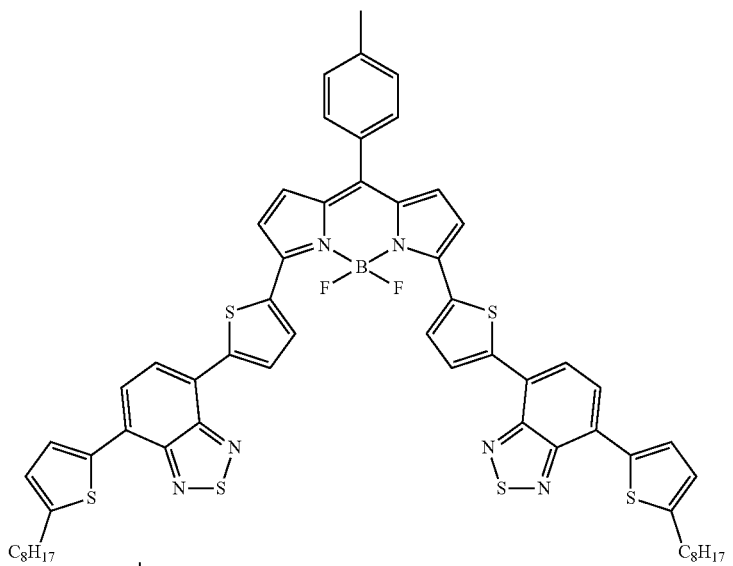
B21
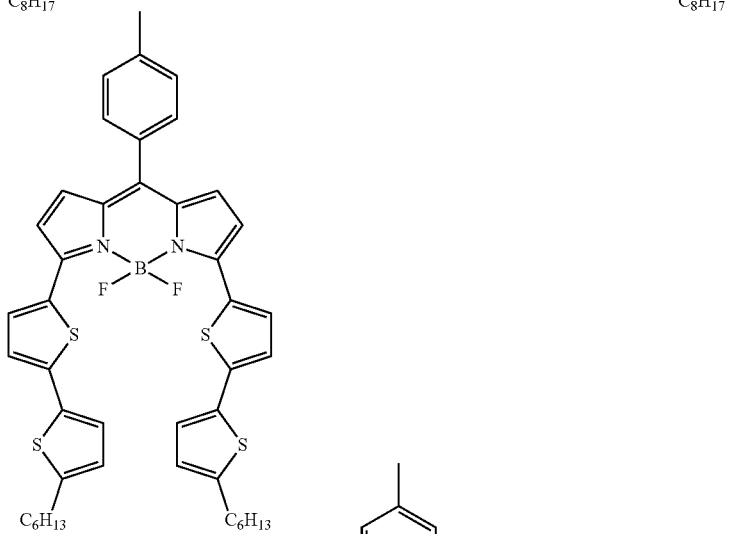
B32
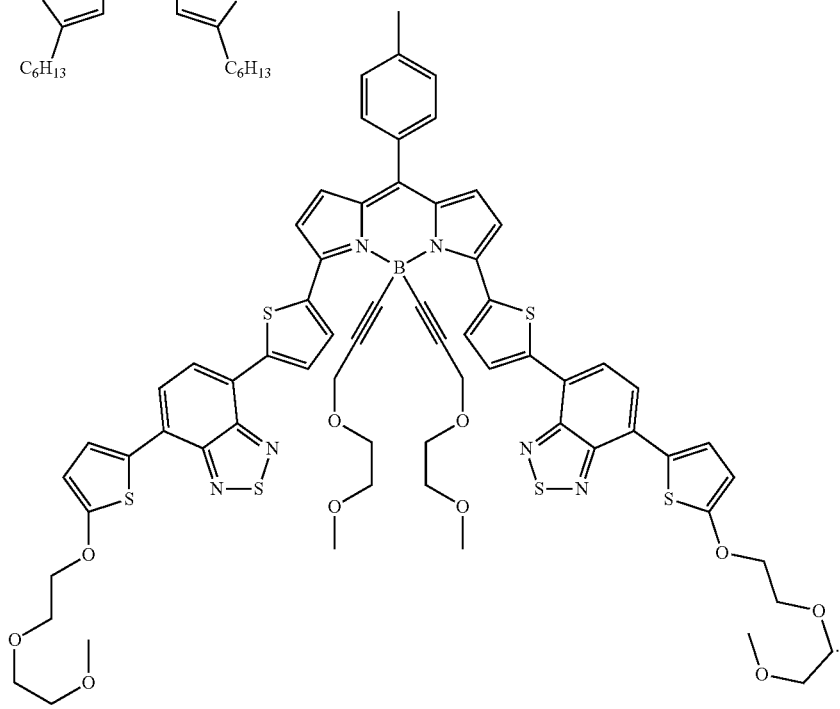

18. Boron dipyrromethene derivative according to claim 16, wherein D represents a group selected from the groups consisting of a thiophene, a furan, a pyridine, a naphthalene, an anthracene, a pyrene, a perylene and a benzothiadiazole group, substituted with one or more thiophene or furan groups and further substituted with one or more linear or branched chains containing 2 to 20 carbon atoms which may contain one or more heteroatoms selected from S, O, Si and N.

* * * * *